(12) United States Patent
Nakao et al.

(10) Patent No.: US 6,251,628 B1
(45) Date of Patent: Jun. 26, 2001

(54) ISOLATED NUCLEIC ACID MOLECULES ENCODING SMAD7

(75) Inventors: Atsuhito Nakao, Chiba (JP); Carl-Henrik Heldin; Peter Ten Dijke, both of Uppsala (SE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/082,092

(22) Filed: May 20, 1998

Related U.S. Application Data

(60) Provisional application No. 60/077,033, filed on Mar. 6, 1998, provisional application No. 60/075,940, filed on Feb. 25, 1998, provisional application No. 60/060,465, filed on Sep. 30, 1997, and provisional application No. 60/047,221, filed on May 20, 1997.

(51) Int. Cl.[7] .......................... C12P 21/02; C07H 21/04; C12N 1/00; C12N 5/10; C12N 15/63
(52) U.S. Cl. .................. 435/69.1; 435/243; 435/320.1; 435/325; 435/410; 536/23.5
(58) Field of Search .................. 536/23.1, 23.5, 536/24.31; 435/320.1, 325, 243, 410, 69.1

(56) References Cited

U.S. PATENT DOCUMENTS 6,048,709 * 4/2000 Falb ...................... 435/69.1

OTHER PUBLICATIONS

Roberts et al., *Growth Factors* 8:1–9, 1993.
Lin and Lodish, *Trends Cell Biol.* 11:972–978, 1993.
Dervnck, *Trends Biochem. Sci.* 19:548–553, 1994.
Massague and Weis–Garcia, *Cancer Surv.*, 27:41–64, 1996.
Ten Dijke et al., *Curr. Opin. Cell. Biol.* 8:139–145, 1996.
Wrana et al., *Nature* 370:341–347, 1994.
Weiser et al., *EMBO J.* 14:2199–2208, 1995.
Graff et al., *Cell* 85:479–487, 1996.
Sekelsky et al., *Genetics* 139:1347–1358, 1995.
Savage et al., *Proc. Nat. Acad. Sci. USA* 93:790–794, 1996.
Wiersdorff et al., *Development* 122:2153–2163, 1996.
Newfeld et al., *Development* 122:2099–2108, 1996.
Hoodless et al., *Cell* 85:489–500, 1996.
Deryck et al., *Cell* 87:173, 1996.
Wrana and Attisano, *Trends Genet.* 12:493–496, 1996.
Hahn et al., *Science* 271:350–353, 1996.
Riggins et al., *Nature Genet.* 13:347–349, 1996.
Eppert et al., *Cell* 86:543–552, 1996.
Massague, *Cell* 86:947–950, 1996.
Derynck and Zhang, *Curr. Biol.* 6:1226–1229, 1996.
Liu et al., *Nature* 381:620–623, 1996.
Meersseman et al., *Mech Dev.* 61:127–1400, 1997.
Baker and Harland, *Genes & Dev.* 10:1880–1889, 1996.
Thomsen, *Development* 122:2359–2366, 1996.
Lechleider et al., *J. Biol. Chem.* 271:17617–17620, 1996.
Yingling et al., *Proc. Nat'l Acad. Sci. USA* 93:8940–8944, 1996.
Zhang et al., *Nature* 383:168–172, 1996.
Macias–Silva et al., *Cell* 87:1215–1224, 1996.
Nakao et al., *J. Biol. Chem.* 272:2896–2900, 1996.
Lagna et al., *Nature* 383:832–836, 1996.
Zhang et al., *Curr. Biol.* 7:270–276, 1997.
de Winter et al., *Oncogene* 14:1891–1900, 1997.
Chen et al., *Nature* 383:691–696, 1996.
Imamura et al., *Nature* 389:622–626, 1997.
Topper et al., *Proc. Nat'l Acad. Sci USA* 94:9314–9319, 1997.
Nakayama et al., *Development* 125:857–867, 1998.
Hemmati–Brivanlou et al., *Nature* 359:606–614, 1992
Chang et al., *Development* 124:827–837, 1997.
Kretzschmar et al., *Genes Dev.* 11:984–995, 1997.

* cited by examiner

*Primary Examiner*—Terry McKelvey
(74) *Attorney, Agent, or Firm*—Wolf, Greenfield & Sacks, P.C.

(57) ABSTRACT

The invention describes nucleic acids encoding the Smad7 protein, including fragments and biologically functional variants thereof. Also included are polypeptides and fragments thereof encoded by such nucleic acids, and antibodies relating thereto. Methods and products for using such nucleic acids and polypeptides also are provided.

18 Claims, 42 Drawing Sheets

```
hSmad7  MFRTKRSALVRRLWRSRAPGGEDEEEGAGG
mSmad7  MFRTKRSALVRRLWRSRAPGGEDEEEGVGG hSmad7  GGGGGELRGEGATDSRAHGAGGGGPGRAGC
mSmad7  GGGGGELRGEGATDGRAYGAGGGGAGRAGC hSmad7  CLGKAVRCAKGHHHPHPPAAGAGAAGGAEA
mSmad7  CLGKAVRGAKGHHHPHPPTSGAGAAGGAEA hSmad7  DLKALTHSVLKKLKERQLELLLQAVESRGG
mSmad7  DLKALTHSVLKKLKERQLELLLQAVESRGG hSmad7  TRTACLLLPGRLDCRLGPGAPAGAQPAQPP
mSmad7  TRTACLLLPGRLDCRLGPGAPASAQPAQPP hSmad7  SSYSLPLLLCKVFRWPDLRHSSEVKRLCCC
mSmad7  SSYSLPLLLCKVFRWPDLRHSSEVKRLCCC hSmad7  ESYGKINPELVCCNPHHLSRLCELESPPPP
mSmad7  ESYGKINPELVCCNPHHLSRLCELESPPPP hSmad7  YSRYPMDFLKPTADCPDAVPSSAETGGTNY
mSmad7  YSRYPMDFLKPTAGCPDAVPSSAETGGTNY hSmad7  LAPGGLSDSQLLLEPGDRSHWCVVAYWEEK
mSmad7  LAPGGLSDSQLLLEPGDRSHWCVVAYWEEK hSmad7  TRVGRLYCVQEPSLDIFYDLPQGNGFCLGQ
mSmad7  TRVGRLYCVQEPSLDIFYDLPQGNGFCLGQ hSmad7  LNSDNKSQLVQKVRSKIGCGIQLTREVDGV
mSmad7  LNSDNKSQLVQKVRSKIGCGIQLTREVDGV hSmad7  WVYNRSSYPIFIKSATLDNPDSRTLLVHKV
mSmad7  WVYNRSSYPIFIKSATLDNPDSRTLLVHKV hSmad7  FPGFSIKAFDYEKAYSLQRPNDHEFMQQPW
mSmad7  FPGFSIKAFDYEKAYSLQRPNDHEFMQQPW hSmad7  TGFTVQISFVKGWGQCYTRQFISSCPCWLE
mSmad7  TGFTVQISFVKGWGQCYTRQFISSCPCWLE hSmad7  VIFNSR (426)
mSmad7  VIFNSR (426)
```

Fig. 1a

| | |
|---|---|
| MFRSKRSGLVRRLWRSRVVPDREEGGSGGGGGGDEDGSLG | hSmad6 |
| MFRSKRSGLVRRLWRSRVVPDREEG-SGGGGGVDEDGSLG | mSmad6 |
| MFRTKRSALVRRLWRSRAPGGEDEEEGAGGGG--GGELR | hSmad7 |
| SRAEPAPRAREGGGCGRSEVRPVAPRRPRDAVGQRGAQGA | hSmad6 |
| SRAEPAPRAREGGGCSRSEVRSVAPRRPRDAVGPRGAAIA | mSmad6 |
| GEGATDSRAHGAGG------------------------- | hSmad7 |
| GRRRRAGGPPRPMSEPGAGAGSSLLDVAEPGGPGWLPESD | hSmad6 |
| GRRRRTGGLPRPVSESGAGAGGSPLDVAEPGGPGWLPESD | mSmad6 |
| ------------------------GGPGR---------- | hSmad7 |
| CETVTCCLFSERDAAGAPRDASDPLAGAALEPAGGG--RS | hSmad6 |
| CETVTCCLFSERDAAGAPRDSGDPQARQSPEPEEGGGPRS | mSmad6 |
| ----AGCCLGKAVRGAKCHHHPHPPAAG----AGAAGGA-- | hSmad7 |
| REARSRLLLLEQELKTVTYSLLKRLKERSLDTLLEAVESR | hSmad6 |
| REARSRLLLLEQELKTVTYSLLKRLKERSLDTLLEAVESR | mSmad6 |
| ----------EADLKALTHSVLKKLKERQLELLLQAVESR | hSmad7 |
| GGVPGGCVLVP-RADLRLG-----GQPAPPQ-----LL | hSmad6 |
| GGVPGGCVLVP-RADLRLG-----GQPAPPQ-----LL | mSmad6 |
| GGTRTACLLLPGRLDCRLGPGAPAGAQPAQPPSSYSLPLL | hSmad7 |
| LGRLFRWPDLQHAVELKPLCGCHSFAAAADGPTVCCNPYH | hSmad6 |
| LGRLFRWPDLQHAVELKPLCGCHSFTAAADGPTVCCNPYH | mSmad6 |
| LCKVFRWPDLRHSSEVKRLCCCESYGKI-NPELVCCNPHH | hSmad7 |
| FSRLCGPESPPPPYSRLSPRDEYKPL-DLSDSTLSYTETE | hSmad6 |
| FSRLCGPESPPPPYSRLSPPDQYKPL-DLSDSTLSYTETE | mSmad6 |
| LSRLCELESPPPPYSRY-PMDFLKPTADCPDAVPSSAETG | hSmad7 |
| ATNSLITAPGEFSDASMSPDATKPSHWCSVAYWEHRTRVG | hSmad6 |
| ATNSLITAPGEFSDASMSPDATKPSHWCSVAYWEHRTRVG | mSmad6 |
| GTNYL--APGGLSDSQLLLEPGDRSHWCVVAYWEEKTRVG | hSmad7 |
| RLYAVYDQAVSIFYDLPQGSGFCLGQLNLEQRSESVRRTR | hSmad6 |
| RLYAVYDQAVSIFYDLPQGSGFCLGQLNLEQRSESVRRTR | mSmad6 |
| RLYCVQEPSLDIFYDLPQGNGFCLGQLNSDNKSQLVQKVR | hSmad7 |
| SKIGFGILLSKEPDGVWAYNREHPIFVNSPTLDAPGGRA | hSmad6 |
| SKIGFGILLSKEPDGVWAYNREHPIFVNSPTLDAPGGRA | mSmad6 |
| SKIGCGIQLTREVDGVWVYNRSSYPIFIKSATLDNPDSRT | hSmad7 |
| LVVRKVPPGYSIKVFDFERS-GLQHAPEPDAADGPYDPNS | hSmad6 |
| LVVRKVPPGYSIKVFDFERS-GLLQ--HADAAHGPYDPHS | mSmad6 |
| LLVHKVFPGFSIKAFDYEKAYSLQRPNDHEFMQQPWTGFT | hSmad7 |
| VRISFAKGWGPCYSRQFITSCPCWLEILLNNPR | hSmad6 |
| VRISFAKGWGPCYSRQFITSCPCWLEILLNNHR | mSmad6 |
| VQISFVKGWGQCYTRQFISSCPCWLEVIFNS-R | hSmad7 |

Fig. 9a

ISOLATED NUCLEIC ACID MOLECULES ENCODING SMAD7

RELATED APPLICATIONS

This application claims priority under 35 U.S.C. §119 from U.S. provisional application serial No. 60/047,221, filed May 20, 1997, from U.S. provisional application serial No. 60/060,465, filed Sep. 30, 1997, from U.S. provisional application serial No. 60/075,940, filed Feb. 25, 1998, and from U.S. provisional application serial No. 60/077,033, filed Mar. 6, 1998.

FIELD OF THE INVENTION

This invention relates to nucleic acids and encoded polypeptides which interact with TGF-β superfamily receptors and which are negative regulators of signaling by those receptors. The invention also relates to agents which bind the nucleic acids or polypeptides. The invention further relates to methods of using such nucleic acids and polypeptides in the treatment and/or diagnosis of disease.

BACKGROUND OF THE INVENTION

During mammalian embryogenesis and adult tissue homeostasis transforming growth factor β (TGF-β) performs pivotal tasks in intercellular communication (Roberts et al., 1993). The cellular effects of this pleiotropic factor are exerted by ligand-induced hetero-oligomerization of two distantly related type I and type II serine/threonine kinase receptors, TβR-I and TβR-II, respectively (Lin and Lodish, 1993; Derynck, 1994; Massague and Weis-Garcia, 1996; ten Dijke et al., 1996). The two receptors, which both are required for signaling, act in sequence; TβR-I is a substrate for the constitutively active TβR-II kinase (Wrana et al., 1994; Weiser et al., 1995). TGF-β forms part of a large family of structurally related proteins which include activins and bone morphogenetic proteins (BMPs) that signal in a similar fashion, each employing distinct complexes of type I and type II serine/threonine kinase receptors (Lin and Lodish, 1993; Derynck, 1994; Massague and Weis-Garcia, 1996; ten Dijke et al., 1996).

Genetic studies of TGF-β-like signalling pathways in Drosophila and *Caenorhabditis elegans* have led to the identification of mothers against dpp (Mad) (Sekelsky et al., 1995) and sma (Savage et al., 1996) genes, respectively. The products of these related genes perform essential functions downstream of TGF-β-like ligands acting via serine/threonine kinase receptors in these organisms (Wiersdorf et al, 1996; Newfeld et al., 1996; Hoodless et al., 1996). Vertebrate homologs of Mad and sma have been termed Smads (Derynck et al., 1996) or MADR genes (Wrana and Attisano, 1996). Genetic alterations in Smad2 and Smad4/DPC4 have been found in specific tumor subsets, and thus Smads may function as tumor suppressor genes (Hahn et al., 1996; Riggins et al., 1996; Eppert et al., 1996). Smad proteins share two regions of high similarity, termed MH1 and MH2 domains, connected with a variable proline-rich sequence (Massague, 1996; Derynck and Zhang, 1996). The C-terminal part of Smad2, when fused to a heterologous DNA-binding domain, was found to have transcriptional activity (Liu et al., 1996; Meersseman et al., 1997). The intact Smad2 protein when fused to a DNA-binding domain, was latent, but transcriptional activity was unmasked after stimulation with ligand (Liu et al., 1996).

Different Smads specify different responses using functional assays in Xenopus. Whereas, Smad1 induces ventral mesoderm, a BMP-like response, Smad2 induces dorsal mesoderm, an activin/TGF-β-like response (Graff et al., 1996; Baker and Harland, 1996; Thomsen, 1996). Upon ligand stimulation Smads become phosphorylated on serine and threonine residues; BMP stimulates Smad1 phosphorylation, whereas TGF-β induces Smad2 and Smad3 phosphorylation (Hoodless et al., 1996; Liu et al., 1996; Eppert et al., 1996; Lechleider et al., 1996; Yingling et al., 1996; Zhang et al., 1996; Macías-Silva et al., 1996; Nakao et al., 1996). Thus certain Smads are pathway specific. Pathway specific Smads include Smad1, Smad2, Smad3 and Smad5.

Smad4 is a common component of TGF-β, activin and BMP signaling (Lagna et al., 1996; Zhang et al., 1997; de Winter et al., 1997). Smad4 phosphorylation has thus far been reported only after activin stimulation of transfected cells (Lagna et al., 1996). After stimulation with TGF-β or activin Smad4 interacts with Smad2 or Smad3, and upon BMP challenge a heteromeric complex of Smad4 and Smad1 has been observed (Lagna et al., 1996). Upon ligand stimulation, Smad complexes translocate from the cytoplasm to the nucleus (Hoodless et al., 1996; Liu et al., 1996; Baker and Harland, 1996; Macías-Silva et al., 1996), where they, in combination with DNA-binding proteins, may regulate gene transcription (Chen et al., 1996).

SUMMARY OF THE INVENTION

The invention provides isolated Smad7 nucleic acid molecules, unique fragments of those molecules, expression vectors containing the foregoing, and host cells transfected with those molecules. The invention also provides isolated polypeptides encoded by the Smad7 nucleic acids and agents which bind such polypeptides, including antibodies. The foregoing can be used in the diagnosis or treatment of conditions characterized by the expression of a Smad7 nucleic acid or polypeptide, or lack thereof. The invention also provides methods for identifying pharmacological agents usefuil in the diagnosis or treatment of such conditions. Here, we present the identification of Smad7, which opposes pathway specific Smads including Smad1, Smad2 and Smad3 and thus is an inhibitor of the TGF-β superfamily signalling pathways.

According to one aspect of the invention, an isolated nucleic acid molecule is provided. The molecule hybridizes under stringent conditions to a molecule consisting of the nucleic acid sequence of SEQ ID NOs:3 or 5. The isolated nucleic acid molecule codes for a polypeptide which inhibits TGF-β superfamily signaling. The invention further embraces nucleic acid lo molecules that differ from the foregoing isolated nucleic acid molecules in codon sequence due to the degeneracy of the genetic code. The invention also embraces complements of the foregoing nucleic acids.

In certain embodiments, the isolated nucleic acid molecule comprises a molecule consisting of the nucleic acid sequence of SEQ ID NO:7 or 8. Preferably, the isolated nucleic acid molecule consists of the nucleic acid sequence of SEQ ID NO:7 or 8, or consists essentially of the nucleic acid sequence of SEQ ID NO:3 or 5.

According to another aspect of the invention, an isolated nucleic acid molecule is provided. The isolated nucleic acid molecule comprises a molecule consisting of a unique fragment of SEQ ID NO:3 between 12 and 1944 nucleotides in length and complements thereof, or a unique fragment of SEQ ID NO:5 between 12 and 1875 nucleotides in length and complements thereof, provided that the isolated nucleic acid molecule excludes sequences consisting only of SEQ ID NO:1 and SEQ ID NO:2. Preferably the isolated nucleic acid molecule excludes molecules consisting solely of nucleotide sequences selected from the group consisting of accession numbers AA061644 (SEQ ID NO: 1), AA022262 (SEQ ID NO:2), AA347307, AA348247, 321995, W78627, W40869, AA033426, AA397050, AA016891, and C85115. In one embodiment, the isolated nucleic acid molecule consists of between 12 and 32 contiguous nucleotides of SEQ ID NO:3, SEQ ID NO:5, or complements of such nucleic acid molecules. In preferred embodiments, the unique fragment is at least 14, 15, 16, 17, 18, 20 or 22 contiguous nucleotides of the nucleic acid sequence of SEQ ID NO:3, SEQ ID NO:5, SEQ ID NO:7, SEQ ID NO:8, or complements thereof.

According to another aspect of the invention, the invention involves expression vectors, and host cells transformed or transfected with such expression vectors, comprising the nucleic acid molecules described above.

According to still other aspects of the invention, transgenic non-human animals are provided. The animals include in certain embodiments the foregoing expression vectors. In certain preferred embodiments, the transgenic non-human animal includes a conditional Smad7 expression vector, such as an expression vector that increases expression of Smad7 in a tissue specific, development stage specific, or inducible manner. In other embodiments, the transgenic non-human animal has reduced expression of Smad7 nucleic acid molecules. In some embodiments, the transgenic non-human animal includes a Smad7 gene disrupted by homologous recombination. The disruption can be homozygous or heterozygous. In other embodiments, the transgenic non-human animal includes a conditional Smad7 gene disruption, such as one mediated by e.g. tissue specific, development stage specific, or inducible, expression of a recombinase. In yet other embodiments, the transgenic non-human animal includes a transacting negative regulator of Smad7 expression, such as antisense Smad7 nucleic acid molecules, nucleic acid molecules which encode dominant negative Smad7 proteins, Smad7 directed ribozymes, etc.

According to another aspect of the invention, an isolated polypeptide is provided. The isolated polypeptide is encoded by the isolated nucleic acid molecule of any of claims 1, 2, 3, 4, 5 or 6, and the polypeptide inhibits TGF-β superfamily signaling activity.

In other embodiments, the isolated polypeptide consists of a fragment or variant of the foregoing which retains the activity of the foregoing. In preferred embodiments, the fragment is a C-terminal fragment of Smad7, preferably amino acids 204–426 of SEQ ID NO:4 or SEQ ID NO:6, or a N-terminal fragment of Smad7, preferably amino acids 2–261 of SEQ ID NO:4 or SEQ ID NO:6.

According to another aspect of the invention, there are provided isolated polypeptides which selectively bind a Smad7 protein or fragment thereof, provided that the isolated polypeptide is not a TGF-β superfamily type I receptor (e.g., a TGF-β, activin or BMP receptor). The isolated polypeptide in certain embodiments binds to a polypeptide encoded by the isolated. nucleic acid molecule of any of claims 1, 2, 3, 4, 5 or 6. In preferred embodiments, isolated binding polypeptides include antibodies and fragments of antibodies (e.g., Fab, F(ab)$_2$, Fd and antibody fragments which include a CDR3 region which binds selectively to an epitope defined by the Smad7 polypeptides of the invention, such as SEQ ID NOs:4 or 6). In other preferred embodiments, the polypeptide is an antibody or fragment thereof which selectively binds an epitope defined by a polypeptide selected from the group consisting of SEQ ID NO: 11, SEQ ID NO:12, SEQ ID NO:13, and SEQ ID NO:14. In still other preferred embodiments, the isolated polypeptide is a monoclonal antibody, a humanized antibody or a chimeric antibody.

The invention provides in another aspect an isolated complex of polypeptides. The isolated complex includes a TGF-β superfamily receptor selected from the group consisting of activated TGFβ superfamily type I receptors and complexes of TGFβ superfamily type I receptors and TGFβ superfamily type II receptors (e.g. a TGF-β, activin, Vg1 or BMP receptors) bound to a polypeptide as claimed in claim 1. Preferably the isolated complex includes a polypeptide having the amino acid sequence of SEQ ID NO:4 or SEQ ID NO:6. In other preferred embodiments, the receptor is selected from the group consisting of TβRI, BMPR-IA, BMPR-IB, ActR-IA, a complex of TβRI and TβRII, a complex of BMPR-IA and BMPR-II, a complex of BMPR-IB and BMPR-II, a complex of ActR-IA and BMPR-II and a complex of ActR-IA and ActR-II.

According to still another aspect of the invention, methods for reducing TGF-β superfamily signal transduction in a mammalian cell are provided. The methods involve contacting a mammalian cell with an amount of an inhibitor of TGF-β superfamily signal transduction effective to reduce such signal transduction in the mammalian cell. Preferably the TGF-β superfamily signal transduction is mediated by a TGFβ superfamily ligand, particularly TGF-β1, activin, VG1, BMP-4 and/or BMP-7. Other methods are provided for reducing phosphorylation of pathway specific Smads (e.g. Smad1, Smad2, Smad3 and/or Smad5) by contacting a mammalian cell with the inhibitor disclosed above. In certain embodiments of the foregoing methods, the inhibitor is an isolated Smad7 polypeptide or a fragment thereof, such as a polypeptide encoded by a nucleic acid which hybridizes under stringent conditions to SEQ ID NO:3 or 5, nucleic acids which encode the polypeptide of SEQ ID NO:4 or SEQ ID NO:6 or degenerates or complements thereof. In some embodiments the nucleic acid encodes amino acids 204–426 of SEQ ID NO:4 or SEQ ID NO:6 or amino acids 2–261 of SEQ ID NO:4 or SEQ ID NO:6. In still other embodiments, the inhibitor is an isolated Smad8 polypeptide or a fragment thereof.

According to still another aspect of the invention, methods for modulating proliferation and/or differentiation of a cell are provided. The methods involve contacting a cell with an amount of an isolated Smad7 polypeptide,or a nucleic acid encoding and expressing such a polypeptide, as described above, effective to modulate the proliferation and/or differentiation of the cell.

The invention in a flrher aspect provides methods for increasing TGF-β superfamily signal transduction in a mammalian cell. The mammalian cell is contacted with an agent that selectively binds to an isolated nucleic acid molecule of the invention or an expression product thereof in an amount effective to increase TGF-β superfamily signal transduction. Preferably the TGF-β superfamily signal transduction is mediated by a TGFβ superfamily ligand selected from the group consisting of TGF-β1, activin, VG1, BMP-4 and BMP-7. Preferred agents are antisense nucleic acids, including modified nucleic acids, and polypeptides including antibodies which bind to the polypeptide including the amino acids of SEQ ID NO:4, the polypeptide including the amino acids of SEQ ID NO:6, the polypeptide including the amino acids of SEQ ID NO: 13, the polypeptide including the amino acids of SEQ ID NO: 14, a N-terninal fragment of Smad7 or a C-terninal fragment of Smad7, and dominant negative variants of the polypeptide of SEQ ID NO:4 or SEQ ID NO:6.

The invention in still another aspect provides compositions comprising a Smad7 polypeptide and a pharmaceutically acceptable carrier.

The invention in a further aspect involves methods for decreasing Smad7 TGF-β superfamily inhibitory activity in a subject. An agent that selectively binds to an isolated nucleic acid molecule of the invention or an expression product thereof is administered to a subject in need of such treatment, in an amount effective to decrease TGFβ superfamily signal transduction inhibitory activity of Smad7 in the subject. Preferably the TGFβ superfamily signal transduction. is mediated by a TGFβ superfamily ligand selected from the group consisting of TGF-β1, activin, VG1, BMP-4 and BMP-7. Preferred agents are antisense nucleic acids, including modified nucleic acids, and polypeptides including antibodies which bind to the polypeptide including the amino acids of SEQ ID NO:4, the polypeptide including the amino acids of SEQ ID NO:6, the polypeptide including the amino acids of SEQ ID NO:13, the polypeptide including the amino acids of SEQ ID NO:14, a N-terminal fragment of Smad7 or a C-terminal fragment of Smad7, and dominant negative variants of the polypeptide of SEQ ID NO:4 or SEQ ID NO:6.

In another aspect the invention provides methods for diagnosing induction of a TGF-β superfamily ligand in a cell. The methods include the steps of (a) measuring the amount of Smad7 RNA or polypeptide in the cell and comparing the result of step (a) with a control.

According to still another aspect of the invention, methods are provided for determining the presence of a functional TGFβ superfamily receptor in a cell. The methods include contacting the cell with an amount of TGFβ superfamily ligand effective to increase the amount of Smad7 in the cell, measuring the amount of Smad7 RNA or polypeptide in the cell, and comparing the result of the measurement with a control, wherein an increased amount of Smad7 RNA or polypeptide in the cell indicates the presence of a finctional TGFβ superfamily receptor. Preferably the TGFβ superfamily receptor is selected from the group consisting of TGFβ superfamily type I receptors, TGFβ superfamily type II receptors, and complexes of TGFβ superfamily type I receptors and TGFβ superfamily type II receptors.

According to another aspect of the invention, methods are provided for identifying lead compounds for a pharmacological agent useful in the diagnosis or treatment of disease associated with TGFβ superfamily signal transduction inhibitory activity of Smad7. One set of methods involves forming a mixture of a Smad7 polypeptide, a TGF-β superfamily receptor complex or an activated TGFβ superfamily type I receptor, and a candidate pharmacological agent. The mixture is incubated under conditions which, in the absence of the candidate pharmacological agent, permit a first amount of specific binding of the TGF-β superfamily receptor complex or activated TGFβ superfamily type I receptor by the Smad7 polypeptide. A test amount of the specific binding of the TGF-β superfamily receptor complex or activated type I receptor by the Smad7 polypeptide then is detected. Detection of an increase in the foregoing activity in the presence of the candidate pharmacological agent indicates that the candidate pharmacological agent is a lead compound for a pharmacological agent which increases the TGF-β superfamily signal transduction inhibitory activity of Smad7. Detection of a decrease in the foregoing activities in the presence of the candidate pharmacological agent indicates that the candidate pharmacological agent is a lead compound for a pharmacological agent which decreases the TGF-β superfamily signal transduction inhibitory activity of Smad7. Another set of methods involves forming a mixture as above, adding further a pathway specific Smad polypeptide, and detecting first and test amounts of TGF-β superfamily induced phosphorylation of the pathway specific Smad polypeptide. Detection of an increase in the phosphorylation in the presence of the candidate pharmacological agent indicates that the candidate pharmacological agent is a lead compound for a pharmacological agent which decreases the TGF-β, superfamily signal transduction inhibitory activity of Smad7. Detection of a decrease in the foregoing activities in the presence of the candidate pharmacological agent indicates that the candidate pharmacological agent is a lead compound for a pharmacological agent which increases the TGF-β, superfamily signal transduction inhibitory activity of Smad7. Preferred Smad7 polypeptides include the polypeptides of claim 18.

In the foregoing compositions and methods, preferred members of the TGF-β superfamily are TGF-β1, activin, VG1, BMP-4 and BMP-7, and the preferred pathway specific Smad polypeptides are Smad1, Smad2, Smad3 and Smad5.

According to yet another aspect of the invention, a method for reducing expression of a Smad6 or Smad7 nucleic acid or expression product thereof in a cell is provided. The method includes contacting the cell with an amount of an agent which binds selectively to Smad4 effective to reduce the expression of the Smad6 or Smad7 nucleic acid or expression product thereof in the cell. In certain embodiments, the agent is an antisense Smad4 molecule, or an antibody that selectively binds to Smad4.

In another aspect, the invention provides a method for increasing Smad6 or Smad7 expression in a cell. The method includes contacting the cell with an agent selected from the group consisting of activin, epidermal growth factor and phorbol esters in an amount effective to increase Smad6 or Smad7 expression in the cell.

According to another aspect of the invention, a method for treating a subject having lung cancer characterized by elevated expression of a Smad6 gene or a Smad7 gene is provided. The method includes administering to the subject an amount of an antisense nucleic acid which binds to the expression product of the Smad 6 or Smad7 gene effective to reduce the expression of the Smad 6 or Smad7 gene. In other embodiments, the method includes administering a polypeptide, such as an antibody or fragment thereof which binds a polypeptide selected from the group consisting of a polypeptide comprising the amino acid sequence of SEQ ID NO:4, a polypeptide comprising the amino acid sequence of SEQ ID NO:6, a N-terminal fragment of Smad7 and a C-terminal fragment of Smad7, a polypeptide comprising the amino acid sequence of SEQ ID NO:10, a polypeptide comprising the amino acid sequence of SEQ ID NO:11, a polypeptide comprising the amino acid sequence of SEQ ID NO:12, a polypeptide comprising the amino acid sequence of SEQ ID NO:13, and a polypeptide comprising the amino acid sequence of SEQ ID NO:14. In still other embodiments, the agent is a dominant negative variant of Smad6 or Smad7.

According to yet another aspect of the invention, methods for reducing eye defects in a developing mammalian embryo are provided. The methods include contacting the cells of the embryo with an agent which reduces the expression or activity of a Smad7 nucleic acid molecule or an expression product thereof. In certain embodiments, the agent selectively binds the Smad7 nucleic acid molecule or an expression product thereof. In preferred embodiments, the agent is an antisense nucleic acid molecule or a polypeptide, and preferably the polypeptide is an antibody or fragment thereof which binds a polypeptide selected from the group consisting of a polypeptide comprising the amino acid sequence of SEQ ID NO:4, a polypeptide comprising the amino acid sequence of SEQ ID NO:6, a polypeptide comprising the amino acid sequence of SEQ ID NO:13, a polypeptide comprising the amino acid sequence of SEQ ID NO:14, a N-terminal fragment of Smad7 and a C-terminal fragment of Smad7. The agent also can be a dominant negative variant of Smad7.

According to another aspect of the invention, an isolated polypeptide is provided. The polypeptide includes a first polypeptide or fragment thereof linked to a second polypeptide or fragment thereof, wherein the second polypeptide or fragment thereof comprises a MH2 domain of Smad7. The polypeptide is localized in the nucleus of a cell and is exported from the nucleus to the cytoplasm of the cell upon TGFβ superfamily receptor-mediated signal transduction in cells having a TGFβ superfamily receptor.

According to another aspect of the invention, a fision protein is provided which includes a Smad7 MH2 domain or a nuclear localization fragment thereof. In other aspects of the invention, a fusion protein is provided which includes a Smad7 MH2 domain or a transcriptional activation fragment thereof.

According to still another aspect of the invention, methods for modulating transcription of Smad7-regulated gene transcription are provided. The methods include contacting a mammalian cell with an agent which modulates TGFβ superfamily receptor-mediated signal transduction in an amount effective to modulate Smad7-regulated gene transcription. In some embodiments the agent is a TGFβ superfamily ligand or an inhibitor of TGFβ superfamily receptor-mediated signal transduction.

In another aspect of the invention, an isolated nucleic acid molecule is provided. The nucleic acid molecule includes the nucleotide sequence of SEQ ID NO:15, an allelic variant thereof, or a functional fragment thereof which confers TGFβ regulation. Nucleic acid molecules which include the nucleotide sequences which hybridize under stringent conditions to SEQ ID NO:15 also are provided. In still other aspects of the invention, isolated nucleic acid molecules which include a unique fragment of SEQ ID NO:15 are provided. Expression vector.s, which include the foregoing isolated nucleic acid molecules including or related to SEQ ID NO:15 also are provided According to another aspect of the invention, method for regulating transcription of a first nucleic acid molecule are provided. The methods include preparing a construct comprising the first nucleic acid molecule operably linked to the foregoing isolated nucleic acid molecules including or related to SEQ ID NO:15, and introducing the construct into an expression system. In some embodiments the expression system is a cell. In preferred embodiments, the cell expresses a TGFβ superfamily receptor, and the method includes contacting the cell with a TGFβ superfamily ligand to increase expression of the first nucleic acid molecule.

In still other aspects of the invention, methods for identifying modulators of TGFβ-regulated transcriptional activity are provided. The methods include providing an expression system with a reporter construct including SEQ ID NO:15 or a TGFβ-regulated fragment thereof operably linked to a nucleic acid encoding a detectable expression product, and contacting the expression system with a candidate modulator compound. The expression system is incubated under conditions which, in the absence of the candidate modulator, permit a first amount of expression of the detectable expression product. A test amount of the expression the detectable expression product then is detected. Detection of an increase in the foregoing activity in the presence of the candidate modulator compound indicates that the candidate modulator compound is a compound which increases TGFβ-regulated transcriptional activity. Detection of a decrease in the foregoing activities in the presence of the candidate modulator compound indicates that the candidate modulator compound is a compound which decreases TGFβ-regulated transcriptional activity. In preferred embodiments the expression system is a cell or an in vitro transcription system. Other other preferred embodiments, the detectable expression product is a reporter protein, such as an enzyme, e.g., luciferase, or a green fluorescent protein.

The use of the foregoing compositions in the preparation of a medicament is also contemplated.

These and other aspects of the invention will be described in further detail in connection with the detailed description of the invention.

BRIEF DESCRIPTION OF THE FIGURES

FIGS. 1A–1B depict the cloning (human Smad7, SEQ ID NO:6; mouse Smad7, SEQ ID NO:4) and tissue distribution of Smad7.

FIGS. 9A–9C show a comparison of Smad6 and Smad7. A: comparison of the amino acid sequences. B: Pairwise alignment relationship between hSmad1 through hSmad7 and hSmad9. C: Expression of Smad6 and Smad7 MnRNA in lung carcinoma cell lines.

FIGS. 10A1, 10A2, 10B, and 10C show that TGF-B superfamily members induce Smad6 and Smad7 mRNA levels.

BRIEF DESCRIPTION OF THE SEQUENCES

Figure 1B:
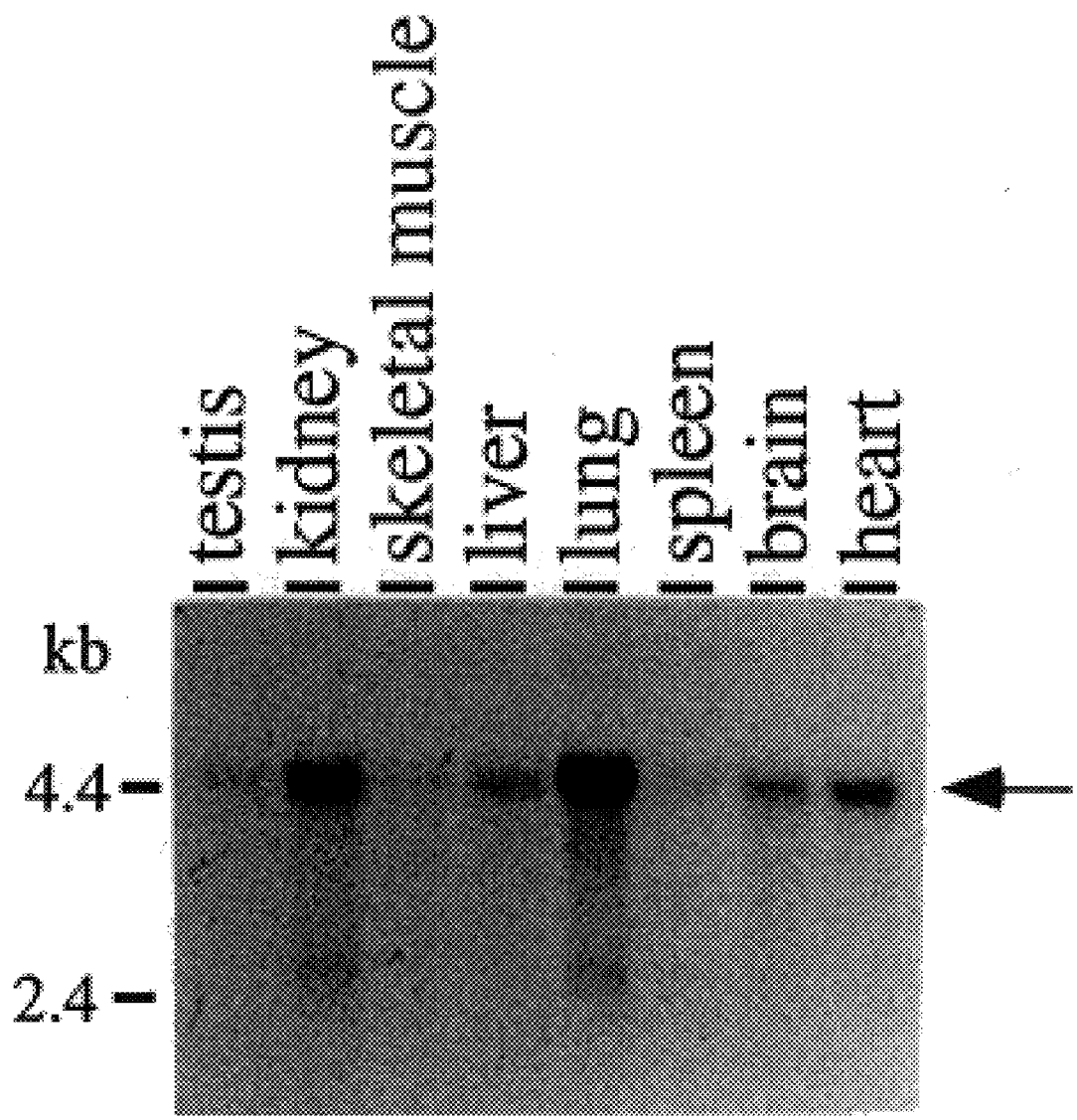

SEQ ID NO:1 is the nucleotide sequence of the mouse EST (accession number A061644) which has sequence similarity to N-terminal Smad domains.

SEQ ID NO:2 is the nucleotide sequence of the mouse EST (accession number A022262) which has sequence similarity to C-terminal Smad domains.

SEQ ID NO:3 is the nucleotide sequence of the mouse Smad7 cDNA.

SEQ ID NO:4 is the amino acid sequence of the mouse Smad7 protein.

SEQ ID NO:5 is the nucleotide sequence of the human Smad7 cDNA.

SEQ ID NO:6 is the amino acid sequence of the human Smad7 protein.

SEQ ID NO:7 is the nucleotide sequence of the coding region of the mouse Smad7 cDNA.

SEQ ID NO:8 is the nucleotide sequence of the coding region of the human Smad7 cDNA.

SEQ ID NO:9 is the nucleotide sequence of the human Smad6 cDNA.

SEQ ID NO:10 is the amino acid sequence of the human Smad6 protein.

SEQ ID NO:11 is the amino acid sequence of a Smad7 preferred peptide to which an antibody can be raised.

SEQ ID NO:12 is the amino acid sequence of a Smad7 preferred peptide to which an antibody can be raised.

SEQ ID NO:13 is the amino acid sequence of a Smad7 preferred peptide to which an antibody can be raised.

SEQ ID NO:14 is the amino acid sequence of a Smad7 preferred peptide to which an antibody can be raised.

SEQ ID NO:15 is the 725 nucleotide Bam HI-Xho I Smad7 minimal promoter fragment.

DETAILED DESCRIPTION OF THE INVENTION

The present invention in one aspect involves the cloning of a cDNA encoding a Smad7 TβR-I receptor-interacting protein. The sequence of the mouse gene is presented as SEQ ID NO:3, and the predicted amino acid sequence of this gene's protein product is presented as SEQ ID NO:4. The sequence of the human gene is presented as SEQ ID NO:5, and the predicted amino acid sequence of this gene's protein product is presented as SEQ ID NO:6. Analysis of the sequence by comparison to nucleic acid and protein databases determined that Smad7 has a C-terminal domain (the MH2 domain) which is related to other Smad proteins. The Smad7 C-terminal domain is most related to Smad6 (48% identity).

The invention thus involves in one aspect Smad7 polypeptides, genes encoding those polypeptides, finctional modifications and variants of the foregoing, useful fragments of the foregoing, as well as therapeutics relating thereto. The expression of these genes affects and is affected by TGF-β superfamily expression and signal transduction. The TGF-β superfamily members are well known to those of ordinary skill in the art and include TGF-βs, activins, bone morphogenetic proteins (BMPs), VG1, Mullerian inhibitory substance (MIS) and growth/differentiation factors (GDFs).

Homologs and alleles of the Smad7 nucleic acids of the invention can be identified by conventional techniques. Thus, an aspect of the invention is those nucleic acid sequences which code for Smad7 polypeptides and which hybridize to a nucleic acid molecule consisting of the coding region of SEQ ID NO:3 or SEQ ID NO:5, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 65° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of Smad7 nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NOs:3 or 5 and SEQ ID NOs:4 or 6, respectively, in some instances will share at least 50% nucleotide identity and/or at least 65% amino acid identity and in still other instances will share at least 60% nucleotide identity and/or at least 75% amino acid identity. Watson-Crick complements of the foregoing nucleic acids also are embraced by the invention.

In screening for Smad7 proteins, a Southern blot may be performed using the foregoing conditions, together with a radioactive probe. After washing the membrane to which the DNA is finally transferred, the membrane can be placed against X-ray film to detect the radioactive signal.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating Smad7 polypeptide. Similarly, nucleotide sequence triplets which encode other amino acid residues include, but are not limited to: CCA, CCC, CCG and CCT (proline codons); CGA, CGC, CGG, COT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NOs:3 or 5 or complements of SEQ ID NOs:3 or 5. A unique fragment is one that is a 'signature' for the larger nucleic acid. It, for example, is long enough to assure that its precise sequence is not found in molecules outside of the Smad7 nucleic acids defined above. A unique fragment excludes, by definition, sequences consisting solely of EST sequences such as those described by SEQ ID NOs:1 and 2. Unique fragments can be used as probes in Southern blot assays to identify such nucleic acids, or can be used in amplification assays such as those employing PCR. As known to those skilled in the art, large probes such as 200 nucleotides or more are preferred for certain uses such as Southern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the Smad7 polypeptides such as the N-terminal and C-terminal fragments disclosed herein, useful, for example, in the preparation of antibodies, in immunoassays, and as a competitive binding partner of the TGF-β, activin, BMP receptors and/or other polypeptides which bind to the Smad7 polypeptides, for example, in therapeutic applications. Unique fragments further can be used as antisense molecules to inhibit the expression of Smad7 nucleic acids and polypeptides, particularly for therapeutic purposes as described in greater detail below.

As will be recognized by those skilled in the art, the size of the unique fragment will depend upon its conservancy in the genetic code. Thus, some regions of SEQ ID NO:3 and/or SEQ ID NO:5 and its complement will require longer segments to be unique while others will require only short segments, typically between 12 and 32 nucleotides (e.g. 12, 13, 14, 15, 16, 17, 18, 19, 20, 21, 22, 23, 24, 25, 26, 27, 28, 29, 30, 31 and 32 bases long). Virtually any segment of SEQ ID NO:7 or SEQ ID NO:8, or complements thereof, that is 18 or more nucleotides in length will be unique. Those skilled in the art are well versed in methods for selecting such sequences, typically on the basis of the ability of the unique fragment to selectively distinguish the sequence of interest from non-Smad7 nucleic acids. A comparison of the sequence of the fragment to those on known data bases typically is all that is necessary, although in vitro confirmatory hybridization and sequencing analysis may be performed.

A unique fragment can be a functional fragment. A functional fragment of a nucleic acid molecule of the invention is a fragment which retains some functional property of the larger nucleic acid molecule, such as coding for a finctional polypeptide, binding to proteins, regulating transcription of operably linked nucleic acids, and the like. One of ordinary skill in the art can readily determine using the assays described herein and those well known in the art tc determine whether a fragment is a functional fragment of a nucleic acid molecule using no more than routine experimentation.

As mentioned above, the invention embraces antisense oligonucleotides that selectively bind to a nucleic acid molecule encoding a Smad7 polypeptide, to increase TGF-β, activin and/or BMP signaling by reducing the amount of Smad7. This is desirable in virtually any medical condition wherein a reduction of Smad7 is desirable, e.g., to increase TGF-β signaling.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NOs:3, 5 or 9, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although SEQ ID Nos:3, 5 and 9 disclose cDNA sequences, one of ordinary skill in the art may easily derive the genomic DNA corresponding to the cDNA of SEQ ID Nos:3, 5 or 9. Thus, the present invention also provides for antisense oligonucleotides which are complementary to the genomic DNA corresponding to SEQ ID Nos:3, 5 and 9. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisens,e molecules that are complementary to and hybridizable with, under physiological conditions, nucleic acids encoding Smad7 polypeptides, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like.

Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding Smad7 polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J Cancer*, 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also permits the construction of Smad7 gene "knock-outs" in cells and in animals, providing materials for studying certain aspects of TGF-β, activin and/or BMP signal transduction.

The invention also provides isolated polypeptides, which include the polypeptides of SEQ ID NOs:4 and 6 and unique fragments of SEQ ID NOs:4 and 6 including fragments comprising amino acids 2–261 of SEQ ID NOs:4 and 6 and amino acids 204–426 of SEQ ID NOs:4 and 6. Such polypeptides are useful, for example, alone or as fusion proteins to generate antibodies, as a components of an immunoassay.

A unique fragment of an Smad7 polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of amino acids 2–261 of SEQ ID NOs:4 and 6 and amino acids 204–426 of SEQ ID NOs:4 and 6 will require longer segments to be unique while others will require only short segments, typically between 5 and 12 amino acids (e.g. 5, 6, 7, 8, 9, 10, 11 and 12 amino acids long). Virtually any segment of amino acids 2–261 of SEQ ID NOs:4 and 6 and amino acids 204–426 of SEQ ID NOs:4 and 6, that is 10 or more amino acids in length will be unique.

Unique fragments of a polypeptide preferably are those fragments which retain a distinct functional capability of the polypeptide. Functional capabilities which can be retained in a unique fragment of a polypeptide include interaction with antibodies, interaction with other polypeptides (such as TβR-I) or fragments thereof, selective binding of nucleic acids or proteins, and enzymatic activity. For example, as exemplified herein, N-terminal and C-terminal Smad7 fragments such as those which includes amino acids 2–261 or 204–426 of SEQ ID NO:4 or SEQ ID NO:6 can be used as a finctional equivalent of full length Smad7 in the methods of the invention, including e.g., inhibition of TGF-β signal transduction. Other Smad polypeptide fragments, e.g., other N-terminal or C-terminal fragments, can be selected according to their functional properties. For example, one of ordinary skill in the art can prepare Smad7 fragments recombinantly and test those fragments according to the methods exemplified below, such as binding to a TGFβ superfamily receptor, or inhibition of pathway specific Smad polypeptide phosphorylation. Those skilled in the art also are well versed in methods for selecting unique amino acid sequences, typically on the basis of the ability of the unique fragment to selectively distinguish the sequence of interest from non-family members. A comparison of the sequence of the fragment to those on known data bases typically is all that is necessary.

The invention embraces variants of the Smad7 polypeptides described above. As used herein, a "variant" of a Smad7 polypeptide is a polypeptide which contains one or more modifications to the primary amino acid sequence of a Smad7 polypeptide. Modifications which create a Smad7 variant can be made to a Smad7 polypeptide 1) to reduce or eliminate an activity of a Smad7 polypeptide, such as binding to TβR-I; 2) to enhance a property of a Smad7 polypeptide, such as protein stability in an expression system or the stability of protein-protein binding; or 3) to provide a novel activity or property to a Smad7 polypeptide, such as addition of an antigenic epitope or addition of a detectable moiety. Modifications to a Smad7 polypeptide are typically made to the nucleic acid which encodes the Smad7 polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the Smad7 amino acid sequence.

In general, variants include Smad7 polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a Smad7 polypeptide by eliminating proteolysis by proteases in an expression system (e.g., dibasic amino acid residues in yeast expression systems in which KEX2 protease activity is present).

Mutations of a nucleic acid which encode a Smad7 polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant Smad7 polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a Smad7 gene or cDNA clone to enhance expression of the polypeptide. The activity of variants of Smad7 polypeptides can be tested by cloning the gene encoding the variant Smad7 polypeptide into a bacterial or mammalian expression vector, introducing the vector into an appropriate host cell, expressing the variant Smad7 polypeptide, and testing for a functional capability of the Smad7 polypeptides as disclosed herein. For example, the variant Smad7 polypeptide can be tested for inhibition of TβR-I, activin and/or BMP receptor signaling activity as disclosed in the Examples, or for inhibition of Smad1, Smad2, Smad3 and/or Smad5 phosphorylation as is also disclosed herein. Preparation of other variant polypeptides may favor testing of other activities, as will be known to one of ordinary skill in the art.

The skilled artisan will also realize that conservative amino acid substitutions may be made in Smad7 polypeptides to provide functionally equivalent variants of the foregoing polypeptides, i.e, the variants retain the functional capabilities of the Smad7 polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the Smad7 polypeptides include conservative amino acid substitutions of SEQ ID NOs:4 or 6. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of Smad7 polypeptides to produce functionally equivalent variants of Smad7 polypeptides typically are made by alteration of a nucleic acid encoding a Smad7 polypeptide (SEQ ID NOs:3 and 5). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a Smad7 polypeptide. Where amino acid substitutions are made to a small unique fragment of a Smad7 polypeptide, such as a TβR-I binding site peptide, the substitutions can be made by directly synthesizing the peptide. The activity of functionally equivalent fragments of Smad7 polypeptides can be tested by cloning the gene encoding the altered Smad7 polypeptide into a bacterial or mammalian expression vector, introducing the vector into an appropriate host cell, expressing the altered Smad7 polypeptide, and testing for a functional capability of the Smad7 polypeptides as disclosed herein. Peptides which are chemically synthesized can be tested directly for function, e.g., for binding to TβR-I, ActR-IB and/or BMPR-IB.

The invention as described herein has a number of uses, some of which are described elsewhere herein. First, the invention permits isolation of the Smad7 protein molecules (SEQ ID NOs:4 and 6). A variety of methodologies well-known to the skilled practitioner can be utilized to obtain isolated Smad7 molecules. The polypeptide may be purified from cells which naturally produce the polypeptide by chromatographic means or imununological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating Smad7 polypeptides. These include, but are not limited to, immunochromatography, HPLC, size-exclusion chromatography, ion-exchange chromatography and immune-affinity chromatography.

The isolation of the Smad7 gene also makes it possible for the artisan to diagnose a disorder characterized by expression of Smad7. These methods involve determining expression of the Smad7 gene, and/or Smad7 polypeptides derived therefrom. In the former situation, such determinations can be carried out via any standard nucleic acid determination assay, including the polymerase chain reaction as exemplified in the examples below, or assaying with labeled hybridization probes.

The invention also makes it possible isolate proteins such as TβR-I, ActR-IB and BMPR-IB by the binding of such proteins to Smad7 as disclosed herein. The identification of this binding also permits one of skill in the art to block the binding of Smad7 to other proteins, such as TβR-I, as well as blocking the binding of other Smads, such as Smad2 or Smad3 to TβR-I receptors. Binding of the proteins can be effected by introducing into a biological system in which the proteins bind (e.g., a cell) a polypeptide including a Smad7 TβR-I binding site in an amount sufficient to block the binding. The identification of a TβR-I domain binding site in Smad7 also enables one of skill in the art to prepare modified proteins, using standard recombinant DNA techniques, which can bind to proteins such as TβR-I, ActR-IB and as BMPR-IB. For example, when one desires to target a certain protein to a TGF-β receptor complex, one can prepare a fusion polypeptide of the protein and the Smad7 TβR-I binding site. Additional uses are described further herein.

The invention further provides methods for reducing or increasing TGF-β family signal transduction in a cell. Such methods are useful in vitro for altering the TGF-β signal transduction, for example, in testing compounds for potential to block aberrant TGF-β signal transduction or increase deficient TGF-β signal transduction. In vivo, such methods are useful for modulating growth, e.g., to treat cancer and fibrosis. Increasing TGF-β signal transduction in a cell by, e.g., introducing a dominant negative Smad7 polypeptide or Smad7 antisense oligonucleotides in the cell, can be used to provide a model system for testing the effects of putative inhibitors of TGF-β signal transduction. Such methods also are useful in the treatment of conditions which result from excessive or deficient TGF-β signal transduction. TGF-β signal transduction can be measured by a variety of ways known to one of ordinary skill in the art, such as the reporter systems described in the Examples. Various modulators of Smad7 activity can be screened for effects on TGF-β signal transduction using the methods disclosed herein. The skilled artisan can first determine the modulation of a Smad7 activity, such as TGF-β signaling activity, and then apply such a modulator to a target cell or subject and assess the effect on the target cell or subject. For example, in screening for modulators of Smad7 useful in the treatment of cancer, cells in culture can be contacted with Smad7 modulators and the increase or decrease of growth or focus formation of the cells can be determined according to standard procedures. Smad7 activity modulators can be assessed for their effects on other TGF-β signal transduction downstream effects by similar methods in many cell types. The foregoing also applies to signalling via activin and BMP complexes.

The invention also provides, in certain embodiments, "dominant negative" polypeptides derived from SEQ ID NOs:4 and/or 6. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein of a Smad7 polypeptide, one of ordinary skill in the art can modify the sequence of the Smad7 polypeptide by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected activity (e.g., Smad7 reduction of TGF-β signalling activity) and/or for retention of such an activity. Other similar methods for creating and testing dominant negative variants of a protein will be apparent to one of ordinary skill in the art.

Dominant negative Smad7 proteins include variants in which a portion of the TβR-I, activin receptor or BMP receptor binding site has been mutated or deleted to reduce or eliminate Smad7 interaction with the TGF-β, activin, or BMP receptor complex respectively. Other examples include Smad7 variants in which the ability to inhibit phosphorylation of Smad2 and/or Smad3 is reduced. One of ordinary skill in the art can readily prepare and test Smad7 variants bearing mutations or deletions in the C-terminal domain (e.g., in the MH2 domain) or in the N-terminal domain (e.g., in the glycine/glutamic acid residue rich region).

The invention also involves agents such as polypeptides which bind to Smad7 polypeptides and to complexes of Smad7 polypeptides and binding partners such as TβR-I, ActR-IB and BMPR-IB. Such binding agents can be used, for example, in screening assays to detect the presence or absence of Smad7 polypeptides and complexes of Smad7 polypeptides and their binding partners and in purification protocols to isolate Smad7 polypeptides and complexes of Smad7 polypeptides and their binding partners. Such agents also can be used to inhibit the native activity of the Smad7 polypeptides or their binding partners, for example, by binding to such polypeptides, or their binding partners or both.

The invention, therefore, embraces peptide binding agents which, for example, can be antibodies or fragments of antibodies having the ability to selectively bind to Smad7 polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')₂ fragment, retains both of the antigen binding sites of an intact antibody. Similarly, an antibody from whictL the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to Smad7 polypeptides, and complexes of both Smad7 polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the Smad7 polypeptide. This process can be repeated through several cycles of reselection of phage that bind to the Smad7 polypeptide. Repeated rounds lead to enrichment of phage bearing particular sequences. DNA sequence analysis can be conducted to identify the sequences of the expressed polypeptides. The minimal linear portion of the sequence that binds to the Smad7 polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the Smad7 polypeptides. Thus, the Smad7 polypeptides of the invention, or a fragment thereof, can be used to screen peptide libraries, including phage display libraries, to identify and select peptide binding partners of the Smad7 polypeptides of the invention. Such molecules can be used, as described, for screening assays, for purification protocols, for interfering directly with the functioning of Smad7 and for other purposes that will be apparent to those of ordinary skill in the art.

A Smad7 polypeptide, or a fragment thereof, also can be used to isolate their native binding partners, including, e.g., the TGF-$\beta$, activin, or BMP receptor complexes. Isolation of such binding partners may be performed according to well-known methods. For example, isolated Smad7 polypeptides can be attached to a substrate (e.g., chromatographic media, such as polystyrene beads, or a filter), and then a solution suspected of containing the TGF-$\beta$ receptor complex may be applied to the substrate. If a TGF-$\beta$ receptor complex which can interact with Smad7 polypeptides is present in the solution, then it will bind to the substrate-bound Smad7 polypeptide. The TGF-$\beta$ receptor complex then may be isolated. Other proteins which are binding partners for Smad7, such as other Smads, activin receptor complexes, and BMP receptor complexes may be isolated by similar methods without undue experimentation.

It will also be recognized that the invention embraces the use of the Smad7 cDNA sequences in expression vectors, as well as to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as human, mouse, hamster, pig, goat, primate, etc. They may be of a wide variety of tissue types, and include primary cells and cell lines. Specific examples include keratinocytes, peripheral blood leukocytes, bone marrow stem cells and embryonic stem cells. The expression vectors require that the pertinent sequence, i.e., those nucleic acids described supra, be operably linked to a promoter.

The invention also includes transgenic non-human animals. As used herein, "transgenic non-human animals" includes non-human animals having one or more exogenous nucleic acid molecules incorporated in germ line cells and/or somatic cells. Thus the transgenic animal include "knock-out" animals having a homozygous or heterozygous gene disruption by homologous recombination, animals having episomal or chromosomally incorporated expression vectors, etc. Knockout animals can be prepared by homologous recombination using embryonic stem cells as is well known in the art. The recombination can be facilitated by the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to Smad7 nucleic acid molecules to increase expression of Smad7 in a regulated or conditional manner. Trans-acting negative regulators of Smad7 activity or expression also can be operably linked to a conditional promoter as described above. Such trans-acting regulators include antisense Smad7 nucleic acids molecules, nucleic acid molecules which encode dominant negative Smad7 molecules, ribozyme molecules specific for Smad7 nucleic acids, and the like. The transgenic non-human animals are useful in experiments directed toward testing biochemical or physiological effects of diagnostics or therapeutics for conditions characterized by increased or decreased Smad7 expression. Other uses will be apparent to one of ordinary skill in the art.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

The invention further provides efficient methods of identifying pharmacological agents or lead compounds for agents active at the level of a Smad7 or Smad7 fragment modulatable cellular function. In particular, such flnctions include TGF-β, activin and/or BMP signal transduction and formation of a TGF-β, activin and/or BMP receptor-Smad7 protein complex. Generally, the screening methods involve assaying for compounds which interfere with a Smad7 activity such as TGF-β receptor-Smad7 binding, etc, although compounds which enhance Smad7 activity also can be assayed using the screening methods. Such methods are adaptable to automated, high throughput screening of compounds. The target therapeutic indications for pharmacological agents detected by the screening methods are limited only in that the target cellular function be subject to modulation by alteration of the formation of a complex comprising a Smad7 polypeptide or fragment thereof and one or more natural Smad7 intracellular binding targets, such as TGF-β receptor. Target indications include cellular processes modulated by TGF-β, activin and/or BMP signal transduction following receptor-ligand binding.

A wide variety of assays for pharmacological agents are provided, including, labeled in vitro protein-protein binding assays, electrophoretic mobility shift assays, immunoassays, cell-based assays such as two- or three-hybrid screens, expression assays, etc. For example, three-hybrid screens are used to rapidly examine the effect of transfected nucleic acids on the intracellular binding of Smad7 or Smad7 fragments to specific intracellular targets. The transfected nucleic acids can encode, for example, combinatorial peptide libraries or antisense molecules. Convenient reagents for such assays, e.g., GAL4 fusion proteins, are known in the art. An exemplary cell-based assay involves transfecting a cell with a nucleic acid encoding a Smad7 polypeptide fused to a GAL4 DNA binding domain and a nucleic acid encoding a TGF-β receptor domain which interacts with Smad7 fused to a transcription activation domain such as VP16. The cell also contains a reporter gene operably linked to a gene expression regulatory region, such as one or more GAL4 binding sites. Activation of reporter gene transcription occurs when the Smad7 and TGF-β receptor fusion polypeptides bind such that the GAL4 DNA binding domain and the VP16 transcriptional activation domain are brought into proximity to enable transcription of the reporter gene. Agents which modulate a Smad7 polypeptide mediated cell function are then detected through a change in the expression of reporter gene. Methods for determining changes in the expression of a reporter gene are known in the art.

Smad7 fragments used in the methods, when not produced by a transfected nucleic acid are added to an assay mixture as an isolated polypeptide. Smad7 polypeptides preferably are produced recombinantly, although such polypeptides may be isolated from biological extracts. Recombinantly produced Smad7 polypeptides include chimeric proteins comprising a fusion of a Smad7 protein with another polypeptide, e.g., a polypeptide capable of providing or enhancing protein-protein binding, sequence specific nucleic acid binding (such as GAL4), enhancing stability of the Smad7 polypeptide under assay conditions, or providing a detectable moiety, such as green fluorescent protein or Flag epitope as provided in the examples below.

The assay mixture is comprised of a natural intracellular Smad7 binding target such as a TGF-β receptor or fragment thereof capable of interacting with Smad7. While natural Smad7 binding targets may be used, it is frequently preferred to use portions (e.g., peptides or nucleic acid fragments) or analogs (i.e., agents which mimic the Smad7 binding properties of the natural binding target for purposes of the assay) of the Smad7 binding target so long as the portion or analog provides binding affinity and avidity to the Smad7 fragment measurable in the assay.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the finctional chemical groups. The candidate agents can comprise cyclic carbon or heterocyclic structure and/or aromatic or polyaromatic structures substituted with one or more of the above-identified finctional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, but for the presence of the candidate pharmacological agent, the Smad7 polypeptide specifically binds the cellular binding target, a portion thereof or analog thereof. The order of addition of components, incubation temperature, time of incubation, and other perimeters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the Smad7 polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromotograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of Smad7 polypeptide interacting with a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseseradish peroxidase, etc.). The label may be bound to a Smad7 binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention provides Smad7-specific binding agents, methods of identifying and making such agents, and their use in diagnosis, therapy and pharmaceutical development. For example, Smad7-specific pharmacological agents are useful in a variety of diagnostic and therapeutic applications, especially where disease or disease prognosis is associated with improper utilization of a pathway involving Smad7, e.g., TGF-β induced phosphorylation of Smad2 or Smad3, TGF-β receptor-Smad7 complex formation, activin or BMP signalling, etc. Novel Smad7-specific binding agents include Smad7-specific antibodies and other natural intracellular binding agents identified with assays such as two hybrid screens, and non-natural intracellular binding agents identified in screens of chemical libraries and the like.

In general, the specificity of Smad7 binding to a binding agent is shown by binding equilibrium constants. Targets which are capable of selectively binding a Smad7 polypeptide preferably have binding equilibrium constants of at least about $10^7$ $M^{-1}$, more preferably at least about $10^8$ $M^{-1}$, and most preferably at least about $10^9$ $M^{-1}$. The wide variety of cell based and cell free assays may be used to demonstrate Smad7-specific binding. Cell based assays include one, two and three hybrid screens, assays in which Smad7-mediated transcription is inhibited or increased, etc. Cell free assays include Smad7-protein binding assays, immunoassays, etc. Other assays useful for screening agents which bind Smad7 polypeptides include fluorescence resonance energy transfer (FRET), and electrophoretic mobility shift analysis (EMSA).

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694–1712; incorporated by reference). Those of skill in the art can readily determine the various parameters and conditions for producing antibody aerosols without resort to undue experimentation. When using antisense preparations of the invention, slow intravenous administration is preferred.

The compositions of the invention are administered in effective amounts. An "effective amount" is that amount of a composition that alone, or together with further doses, produces the desired response, e.g. alters favorably the signal transduction resulting from binding of TGF-β, activin, BMP and/or Vg1 (Vgr-1) to specific receptors. In the case of treating a particular disease, such as cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of Smad7 or nucleic acid encoding Smad7 for producing the desired response in a unit of weight or volume suitable for administration to a patient. The response can, for example, be measured by determining the signal transduction enhanced or inhibited by the Smad7 composition via a reporter system as described herein, by measuring downstream effects such as gene expression, or by measuring the physiological effects of the Smad7 composition, such as regression of a tumor or decrease of disease symptoms. Likewise, the effects of antisense Smad6 and Smad7 can be readily determined by measuring expression of the individual genes in cells to which an antisense composition is added. Other assays will be known to one of ordinary skill in the art and can be employed for measuring the level of the response.

The doses of Smad7 polypeptide or nucleic acid administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses of Smad7 are formulated and administered in doses between 1 ng and 1 mg, and preferably between 10 ng and 100 $\mu$g, according to any standard procedure in the art. Where nucleic acids encoding Smad7 of variants thereof are employed, doses of between 1 ng and 0.1 mg generally will be formulated and administered according to standard procedures. Other protocols for the administration of Smad7 compositions will be known to one of ordinary skill in the art, in which the dose amount, schedule of injections, sites of injections, mode of administration (e.g., intra-tumoral) and the like vary from the foregoing. Administration of Smad7 compositions to mammals other than humans, e.g. for testing purposes or veterinary therapeutic purposes, is carried out under substantially the same conditions as described above.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Smad7 may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous or non-aqueous preparation of Smad7 polypeptides or nucleic acids, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

In another aspect of the invention, Smad7 polypeptides or nucleic acid are used in the manufacture of a medicament for modulating a TGF-β, activin, BMP or Vg1 response. The medicament can be placed in a vial and be incorporated into a kit to be used for increasing a subject's response to one or more of the above TGF-β family members. In certain embodiments, other medicaments which modulate the same responses or which favorably affect the Smad7 compositions can also be included in the same kit. The kits can include instructions or other printed material on how to administer the Smad7 compositions and any other components of the kit.

EXAMPLES

Methods

Isolation of mSmad7 and hSmad7 cDNA and Northern Blot Analysis.

cDNA encoding the complete mSmad7 was made by fusing mouse EST cDNA (AA061644) with a partial cDNA isolated from a mouse placenta library. The cDNA for hSmad7 was isolated by screening a human brain cDNA library. cDNAs were sequenced on both strands using an ABI310 Genetic Analyzer. Isolation of total RNA, Northern blot analysis was performed as described before (Afrakhte, M. et al., *Int. J. Cancer* 68, 802–809 (1996) using QUIKHYB® hybridization solution from Stratagene (La Jolla, Calif.).

Expression Plasmids.

Expression constructs for TβR-I, TβR-II, BMPR-IA, BMPR-IB, ActR-I, ActR-IB, Smad1, Smad2, Smad3 and Smad5 have been described previously (Nakao et al., *EMBO J.* 16:5353–5362, 1997). Other Smad or receptor plasmids have been previously described or were prepared according to standard protocols. F-Smad7 and F-Smad8 were made by a PCR-directed approach and subcloning into pcDNA-Flag.

N-terminal and C-termninal Smad7 expression vectors were prepared using PCR amplification with specific primers and Smad7 cDNA as template. Expression constructs for the C-terminal domain of F-Smad7 (7C; amino acids 204–426), F-Smad7C with C-tail deletion (7CΔ; amino acids 204–207), Smad7 with deletion of C-tail (7Δ; amino acids 1–407), the N-terminal domain of Smad7 (7N; amino acids 1–203), mouse F-Smad6 "long version" (F-Smad6L) (Imamura et al., 1997) and human F-Smad6 "short version" (F-Smad6S) (Topper et al., 1997), were made by a PCR-directed approach and were subcloned into pcDNA3-Flag. The resulting expression plasmids expressed N-terminal and C-terminal Smad domains tagged at their N-termini with the Flag epitope. Alternatively, the Smads and Smad fragments were subcloned into pMEP4 for inducible expression of the proteins. Anti-sense expression constructs for Smad molecules including mSmad7 and hSmad3 were prepared by cloning the complete Smad coding regions in reverse direction in pcDNA3 expression vector (Invitrogen, Carlsbad, Calif.).

Cell Assays.

Transient transfection, metabolic labeling, immunoprecipitation, [$^{32}$P]orthophosphate labeling of cells, and SDS-PAGE were performed as described previously (Nakao et al., 1997).

Iodination of Ligand and Affinity Cross-linking.

Iodination of TGF-β1 and affinity cross-linking followed by immunoprecipitation were performed as previously described (Nakao et al., 1997). TGF-β1 and BMP-7 were iodinated using the chloramine-T method according to Frolik et al (*J. Biol. Chem.* 259:10995–11000, 1984). Cross-linking was performed as previously described (Nakao et al., 1997). In some cases, incubation with $^{125}$I-TGF-β1 was performed at room temperature for 2 h (Souchelnytskyi et al., *J. Biol. Chem.* 272:27678–27685, 1997) and the transfected cells lines were stimulated for 24 h with 100 μM/ml zinc chloride to induce the expression of Smad7. Complexes of Smads and affinity-labeled receptors were immunoprecipitated with antiserum directed against epitope tags in Smads. To determine expression levels of receptors, aliquots of cell lysates were immunoprecipitated with antisera against type I receptors. Expression of Smads was determined by Western blotting on aliquots of cell lysates.

Transcriptional Response Assay.

Mv1Lu wild-type and R mutant cells were transiently transfected with p3TPLux using DEAE-dextran transfection method, as described before (Nakao et al., 1997). HaCat cells were transiently transfected with p21 reporter plasmid (Datto et al., *J. Biol. Chem.* 270: 28623–28628, 1995) using Transfectam reagent from Promega (Madison, Wis.). In each experiment, equal total amounts of DNA were transfected. In other experiments, Mv1Lu cells were transfected with p3TPLux and anti-sense expression constructs using Lipofectin; after incubation overnight in Optimum medium, the medium was changed to serum-containing medium. After another 24 h or incubation the cells were stimulated with TGF-β1 and luciferase activity was measured. Luciferase activity was measured as previously described (Nakao et al., 1997). The values were normalized for transfection efficiency using the β-gal reporter gene under transcriptional control of CMV promoter (pCMV5 vector). Results shown are representative of at least three or four independent experiments.

Transient transfections of COS cells were performed using the DEAE-dextran protocol. Stable transfection of Mv1Lu cells with pMEP4 expression vector (Invitrogen) was done using calcium phosphate precipitation method, as previously described (Souchelnytskyi et al., 1997); selection was performed with 420 units/ml hygromycin. Induction with zinc chloride was done with 100 µM zinc chloride for 20 h, unless indicated otherwise. Metabolic labeling of cells, [$^{32}$P]orthophosphate labeling, and immunoprecipitation, and SDS-PAGE were performed as earlier described (Souchelnyskyi et al., 1997 or Nakao et al., 1997).

Xenopus Embryo Culture and Manipulation.

Xenopus eggs were obtained and embryos microinjected and cultured as described (Moon and Christian, *Technique* 1: 76–89, 1989). For animal cap assays, 200 pg of RNA encoding activin-β or a bone morphogenetic protein-Vg1 chimera (Dale et al., *EMBO J*. 12: 4471–4480, 1993) was injected either alone, or together with 400 pg of Smad7 RNA. For Smad7/Smad8 experiments, RNA was synthesized by in vitro transcription (Moon and Christian, 1989) of pCS2+Smad8 and pCS2+Smad7 (Nakayama et al., *Development* 125:857–867, 1998). The latter construct was generated by subcloning the coding region of F-Smad7 into pCS2+ (Turner and Weintraub, *Genes Dev*. 8:1434–1447, 1994). Embryonic stages are according to Nieuwkoop and Faber (*Normal table of Xenopus laevis*, Garland Publishing, Amsterdam, North Holland, 1967). Immunostaining of whole embryos (12/101 antibody was obtained from the Developmental Studies Hybridoma Bank under contract N01-HD-2-3144 from the NICHD, Tor 70 was obtained from R. Harland), whole mount in situ hybridization, RT-PCR analysis of RNA extracted from cultured animal caps, and quantitation of brachyury expression relative to that of EF-la were performed as described (Lagna et al., *Nature* 383: 832–836, 1996; Cui et al., *Dev. Biol.* 180: 22–34, 1996; Moon and Christian, 1989).

Cell Lines.

COS cells and Mv1Lu mink lung epithelial cells and HaCat cells (human keratinocytes) were obtained from American Type Culture Collection. Cells were cultured in Dulbecco's modified Eagle's medium (Life Technologies, Inc., Gaithersburg, Md.) supplemented with 10% fetal bovine serum (FBS) and antibiotics (100 units of penicillin and 50 µg of streptomycin per ml). All the 10 different human lung carcinomas used [small cell lung carcinoma (SCLC), U-1285, U-1690, H-69 and H-92; non-SCLC, U-1752; squamous cell carcinoma (SQC); U-1810; large-cell carcinoma (LCC), H-157, H-661; adenocarcinoma (ADC) H-23 and H-125 (Histological typing of lung tumors, according to WHO, Geneva)] were grown in RPMI 1640 medium with 10% FBS and antibiotics. (Heldin et al., *Br. J. Cancer*, 68: 708–711, 1993).

RNA Isolation and Northern Blot Analysis.

Cells were kept in 0.5% FBS 12–24 h prior to stimulation with various factors followed by RNA extraction. Lung carcinoma cells used for RNA extraction were grown in the presence of 10% FCS. Isolation of total RNA and Northern blotting was performed essentially as described (Afrakhte et al., *Int. J. Cancer*, 68:802–809, 1996). The RNA extracted from the lung carcinomas cell lines was poly(A)$^+$-enriched. Hybridizations were performed using QuickHyb buffer from Stratagene. The intactness and total amount of RNA (12 µg or total RNA or 5 µg of poly(A)$^+$ RNA per lane) were checked by staining the gel with ethidium bromide and by hybridization with a glyceraldehyde 3-phosphate dehydrogenase (GAPDH) probe. The cDNA probes used in the hybridizations were a 1.8 kb Eco/Xho I human Smad7 fragment, a 2.0 kb EcoRI fragment of the human Smad6, a 3 kb Eco RI fragment of the human PAI-1, and a 1.5 kb mouse JunB fragment. For the GAPDH hybridizations the entire human GAPDH cDNA plasmid was labeled.

Antibodies

Antibodies against Smad2, termed DQQ, have been previously described (Nakao et al., 1997). Anti-Flag antibody was purchased from Kodak (New Haven). Specific antisera for Smad6, termed ESP and SRQ were raised against ESP-PPPYSRLSPRDEYKPLD (SEQ ID NO:11) and SRQFITSCPCWLEILNPR (SEQ ID NO:12), respectively. Specific antisera raised against Smad7, termed KER and KAV, were raised against the synthetic peptides KER-QLELLLQAVESRGGTRTA (SEQ ID NO:13) and KAVR-GAKGHHHPHPP (SEQ ID NO:14), respectively. The peptides were coupled to keyhole limpet haEmocyanin (Calbiochem-Behring) with glutaraldehyde, mixed with Freund's adjuvant, and used to immunize rabbits according to standard procedures.

Growth Inhibition Assay

Mv1Lu cells were seeded at 1×10$^4$ cells/well in 24-well plates. Prior to addition of TGF-β1 the Mv1Lu cells were simultaneously treated (or not) with 100 µM zinc chloride and indicated concentrations of TGF-β1 for 20 h to induce Smad7 expression. Before harvesting, the cells were pulsed with 0.2 µCi of [$^3$H] thymidine (6.7 Ci/mmol, Amersham, UK) for 2h. The cells were fixed with ice-cold 5% trichloroacetic acid (TCA) for more than 20 min, washed twice with 5% TCA and once with water. Solubilization of the cells was done with 400 µl of 0.1 M NaOH for 20 min at room temperature. The $^3$H-radioactivity incorporated into DNA was determined by liquid scintillation counting.

Cells were grown in LAB TEK chambers (Nunc, Naperville, Ill.), and incubated with DMEM containing 0.3% FCS in the absence or presence of TGF-β1 for 2 h. The slides were washed once with phosphate buffered saline (PBS), fixed for 10 min with 4% paraformaldehyde, followed by three washes with PBS, subsequently permeabilized with 0.1% Triton X-100 in PBS for 5 min, and again washed three times with PBS. Slides were blocked by 10% goat serum for 1 h in room temperature, then incubated with 10% goat serum with anti-FLAG antibody (20 µg/ml) for 15 h at 4° C. The slides were subsequently washed 3 times, incubated with TRITC-conjugated goat anti-mouse IgG antibody (diluted 1:40) and washed again 4 times. Nuclei were stained with DAPI (1 µg/ml) for 10 min in room temperature followed by three washes. In order to visualize the fluorescence, a Zeiss microscope, or laser confocal microscope was used. For cell counting a square lattice mounted in one of the eyepieces was used. In the COS cell experiments 200 cells were counted in 5 different field and the nuclear localization was checked by DAPI staining.

Example 1

Cloning and Characterization of Smad7

A database search for mammalian sequences related to Smads revealed the existence of two mouse expression sequence tags (ESTs), i.e. AA022262 and AA061644, with sequence similarity to N- and C-terminal Smad domains, respectively. Polymerase chain reaction (PCR) using kidney cDNA as a template with a PCR primer pair derived from both ESTs resulted in a specific product. A cDNA encoding the complete mouse protein was made by fusing mouse EST cDNA with a cDNA isolated from a mouse placenta library, and was termed mouse Smad7 (mSmad7). Human Smad7 cDNA (hSmad7) was isolated from a human brain cDNA library. The cDNA sequences predict that mSmad7 and hSmad7 have 426 amino acid residues with 98% identity (FIG. 1a).

All differences between hSmad7 and mSmad7 are found in the N-terminal domain. The borders of the Mad homology 2 (MH2) domain are indicated by arrows. The nucleotide sequences are deposited in European Molecular Biology Laboratory/GenBank data library (mouse and human Smad7 accession numbers are AF0152260 and AF015261, respectively). Smad7 is most related to Smad6 (Imamura et al., *Nature*, 389:622–626, 1997) with 36% and 56% sequence identities in the N-terminal domain and the C-terminal MH2 domain, respectively. The Smad7 N-terminal domain, which contains a glycine/glutamic acid residue-rich region, shows only weak similarity (approximately 15%) to the MH1 domains found in Smad1 through Smad5.

RNA blot analysis of various tissues with a probe from the region coding for the N-terminal domain of Smad7 revealed one major transcript of approximately 4.4 kb (FIG. 1b). Among the tissues analyzed, the highest expression of Smad7 was found in the lung.

Example 2

Smad7 Modulates TGF-β Superfamily Signal Transduction

Figure 2A:
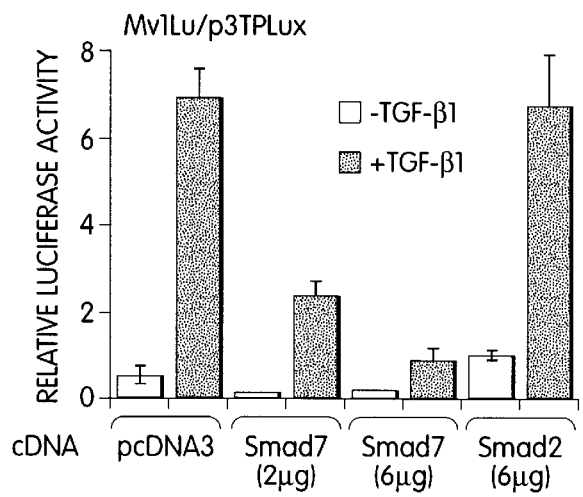
FIGS. 2A–2I show that Smad7 inhibits TGF-β and activin induced transcriptional responses.
Figure 2B:
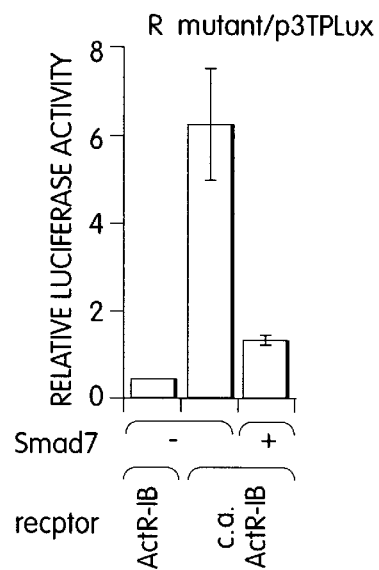

To investigate whether Smad7 modulates the responsiveness to TGF-β, the TGF-β-inducible luciferase p3TPLux reporter construct, which contains the TGF-β-inducible PAI-1 promoter, was transfected into MV1Lu mink epithelial cells in the absence or presence of Smad7 cDNA. Smad7 was found to exert a dose-dependent inhibition TGF-β-induce luciferase activity (FIG. 2a). Moreover, the induction of p3TPLux luciferase by a constitutively active variant of TβR-I, when transfected in R-mutant cells, was also inhibited by cotransfection with Smad7, as was the response by a constitutively active variant of the structurally related type I receptor for activin (ActR-IB) (FIG. 2B). Transfection of Smad2 did not affect TGF-β1-induced p3TPLux luciferase response in Mv1Lu cells (FIG. 2a). This inhibitory effect was specific as Smad7 did not inhibit the phorbol 12-myristate 13-acetate (PMA)/epiderrnal growth factor-induced p3TPLux luciferase response. In addition, the forskolin-mediated transcriptional induction using a cAMP-responsive-element-containing reporter construct was not affected by Smad7. These results indicate that Smad7 is a potent negative regulator of both TβR-I- and ActR-IB-induced p3TPLux response.

Figure 2C:
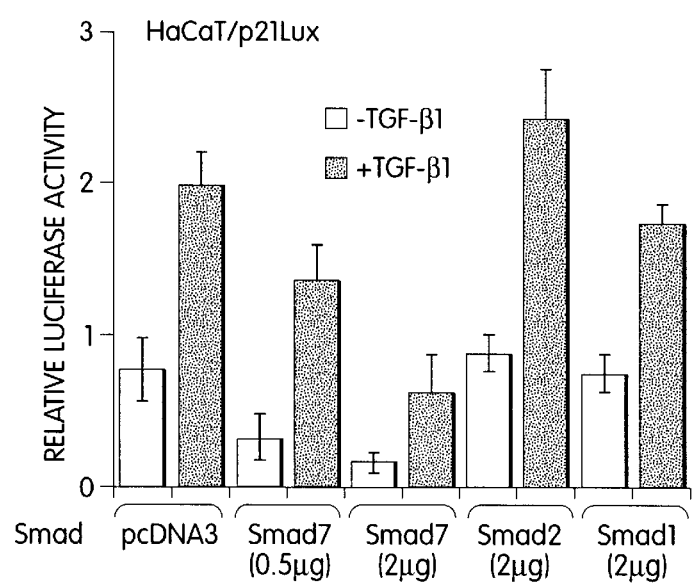

To examine the effect of Smad7 expression on TGF-β-mediated growth inhibition, a luciferase transcriptional reporter construct containing the p21 CDK inhibitor promoter (p21Lux) that is induced by TGF-β in human keratinocytes (HaCat) (Imamura, 1997) was used. Smad7 was found to antagonize TGF-β1-mediated p21 Lux response in HaCat cells dose-dependently (FIG. 2c). Increased expression of Smad2 by transfection slightly stimulated this response, whereas Smad1 transfection had no effect (FIG. 2c). Smad7 and N-terminally Flag-tagged Smad7 gave essentially the same antagonistic results on TGF-β signaling, suggesting that N-terminal tagging does not interfere with functional properties of Smad7. Thus, Smad7 inhibits TGF-β-induced pathways leading to extracellular matrix production as well as growth inhibition.

Figures 2D, 2E, 2F, 2G, 2H, 2I:
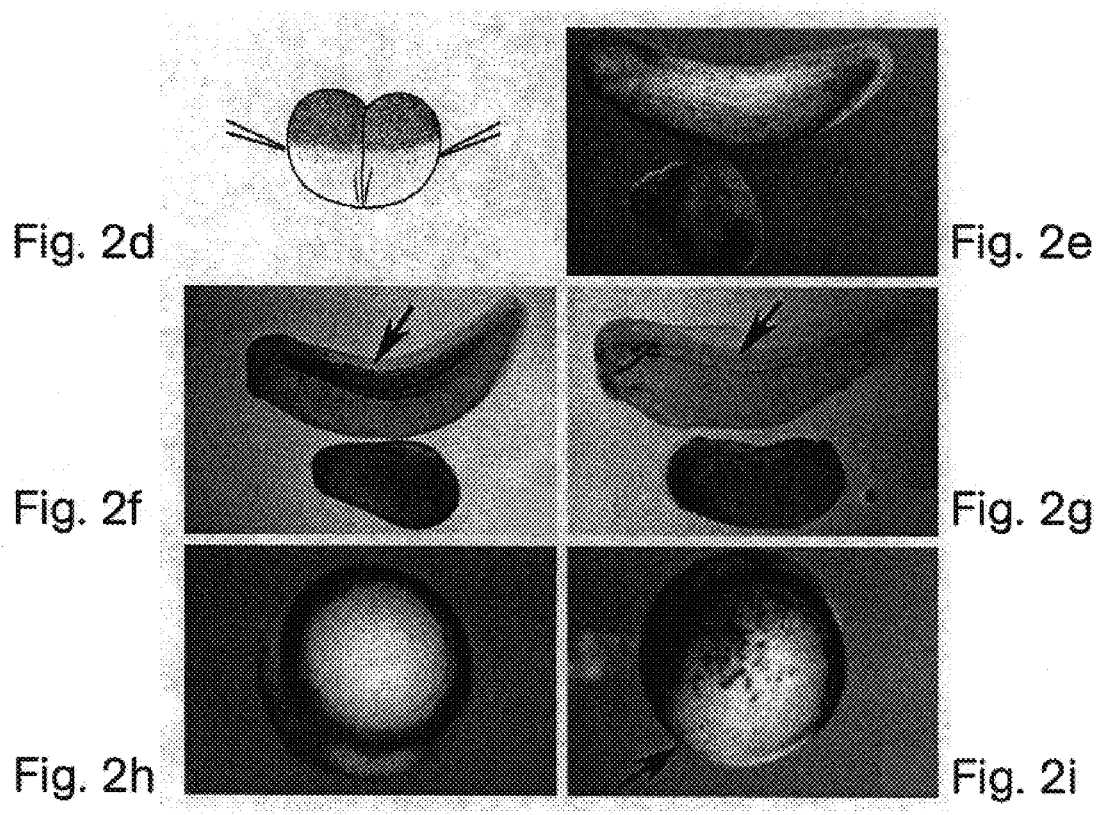

To determine whether Smad7 can inhibit transduction of TGF-β/activin-like signals in vivo, patterning defects caused by overexpression of Smad7 in Xenopus embryos were analyzed. When the endogenous activin signaling pathway is inactivated in early Xenopus embryos, by introduction of dominant negative forms of either an activin receptor (Hemmati-Brivanlou et al., *Nature* 359: 606–614, 1992; Chang et al., *Development* 124: 827–837, 1997) or of Smad4 (Lagna et al., *Nature* 383: 832–836, 1996), mesoderm fails to form. Similarly, microinjection of RNA encoding Smad7 into both blastomeres of two-cell embryos inhibited mesoderm formation (FIGS. 2d–g). Five hundred picograms of synthetic RNA encoding either Smad7 or myc-epitope tag (MT) was injected into each blastomere of two-cell embryos as shown schematically (FIG. 2d) and embryos were cultured to the tailbud stage. Embryos injected with MT RNA developed normally (top embryo in each panel) whereas embryos made to misexpress Smad7 (bottom embryo in each panel) failed to form head or tail structures (FIG. 2e) and showed a complete or partial loss of muscle (FIG. 2f) and notochord (FIG. 2g). Arrows indicate immunoreactive muscle (FIG. 2f) and notochord (FIG. 2g) in MT-injected embryos. Specifically, head and tail structures were absent or severely deficient in 80% of injected embryos (n=168) (FIG. 2e) as were mesodermal derivatives such as muscle (n=60) (FIG. 2f) and notochord (n=48) (FIG. 2g).

To further test the ability of Smad7 to block mesoderm formation in vivo, embryos were analyzed for expression of brachyury, a gene that is expressed throughout the presumptive mesoderm during gastrulation (Smith et al., *Cell* 67:79–87,1991) (FIG. 2h). Five hundred picograms of synthetic RNA encoding MT (FIG. 2h) or Smad7 (FIG. 2i) was injected into one blastomere of two-cell embryos near the equator and expression of brachyury analyzed by whole mount in situ hybridization. MT-injected embryos show the typical ring of brachyury expression (FIG. 2h) while brachyury transcripts are not detected on one side of Smad7-injected embryos (FIG. 2i, arrow). As shown in FIG. 2i, injection of Smad7 RNA into the equatorial region of one blastomere of two-cell embryos prevented brachyury expression on one side of the embryo.

Two members of the TGF-β family, activin and VG1, are candidates for being endogenous mesoderm-inducing molecules (Kessler et al., *Science* 266: 596–604, 1994). A Xenopus animal cap assay (Kessler, 1994) was usedto directly test the ability of Smad7 to block signaling downstream of these ligands. While both activin and Vg1 induced expression of brachyury in ectodermal explants (animal caps), coexpression of Smad7 inhibited brachyury induction of 60%, thereby demonstrating that Smad7 can block activin and Vg 1-mediated mesoderm induction.

Figure 3:
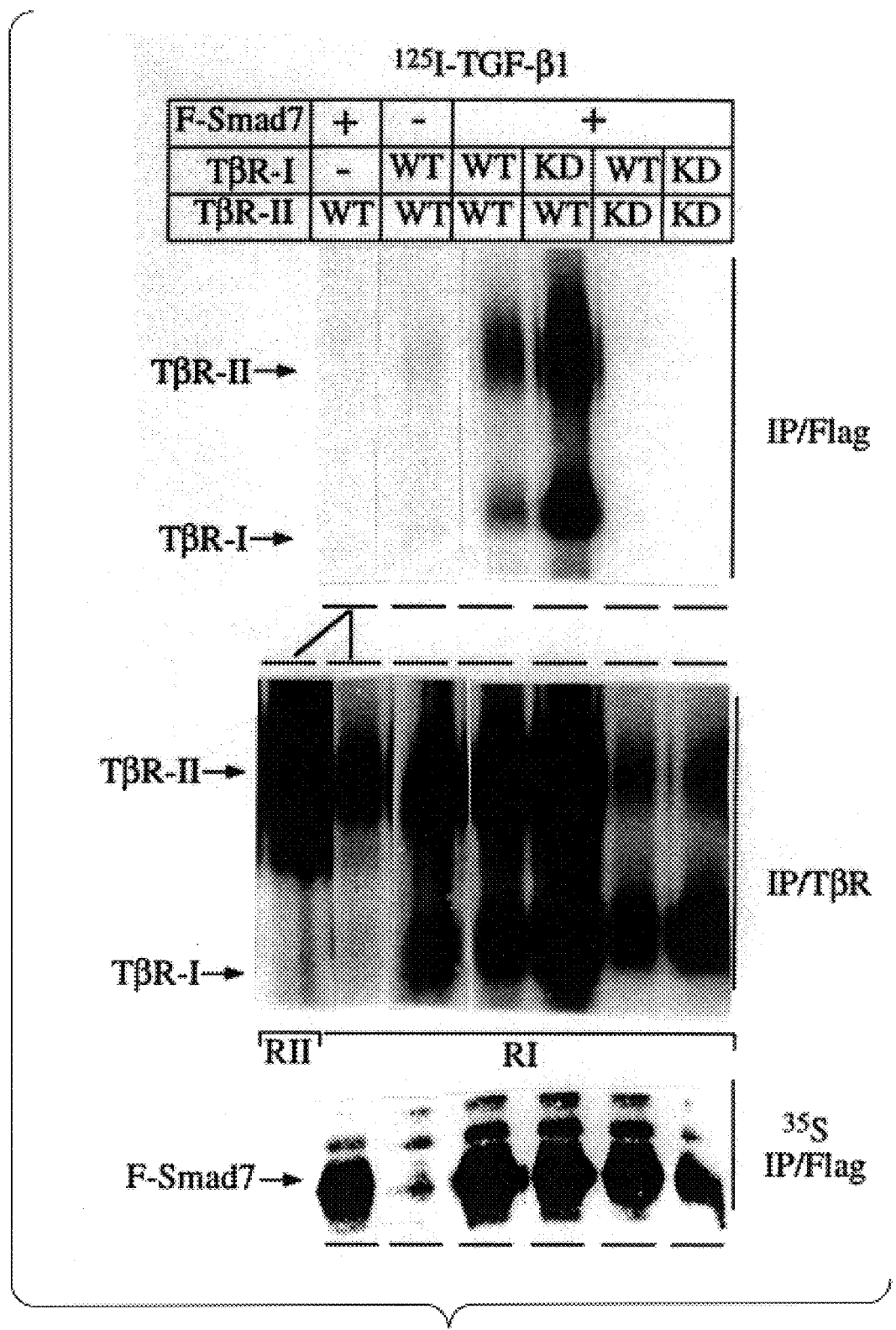
FIG. 3 demonstrates the association of Smad7 with the TGF-β receptor complex.

To obtain insight into the mechanism by which Smad7 exerts its negative role in signaling by TGF-β family members, it was tested whether Smad7, like Smad2 and Smad3 (Zhang et al., *Nature* 383:168–172, 1996; Macías-Silva et al., *Cell* 87:1215–1224, 1996; Nakao et al., 1997), can associate with the TGF-β receptor complex. COS cells transfected with N-terminally Flag-tagged Smad7 in combination with TβR-II (wild-type, WT, or kinase-deficient mutant, KD) and TβR-I (wild-type or kinase deficient mutant) were affinity labeled with $^{125}$I-TGF-β1, and cell lysates were subjected to immunoprecipitation with Flag antiserum against the Flag-epitope in Smad7. Immunoprecipitates were analyzed by SDS-PAGE and FujiX Bio-Imager. Expression of receptors and F-Smad7 after transfection was determined by immunoprecipitation with VPN antibody against TβR-I or DRL antibody against TβR-II on aliquots of cell lysates, and by immunoprecipitation with Flag antibody on lysates [$^{35}$S] methionine/cysteine labeled transfected cells. It was found that Smad7 interacted very efficiently with the TGF-β receptor complex (FIG. 3). Smad7 interacted with wild-type TβR-I as well as kinase inactive TβR-I in complex with wild-type TβR-II. In contrast, Smad2 and Smad3 interact stably only with complex of kinase-deficient TβR-I and wild-type TβR-II (Macías-Silva et al., 1996; Nakao et al., 1997). No interaction was observed between Smad7 and a heteromeric complex of kinase-deficient TβR-II and TβR-I, or with TβR-II alone (FIG. 3). Thus, transphosphorylation of TβR-I by TβR-II kinase is required for association of Smad7 with TβR-I.

Example 3
Phosphorylation of Smad7

Figure 4A:
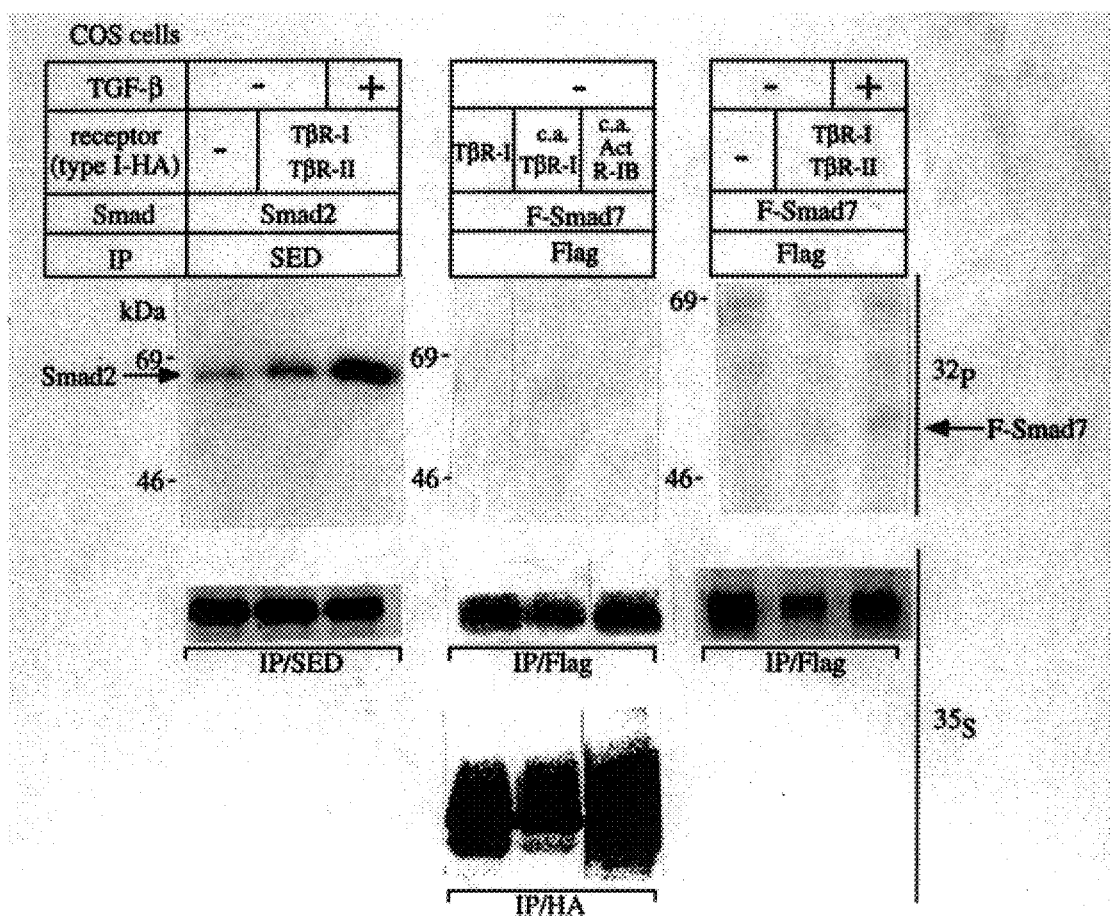
FIGS. 4A–4E show that Smad7 is not phosphorylated upon TβR-activation, but Smad7 overexpression inhibits TGF-β-mediated Smad2 and Smad3 phosphorylation.
Figure 4B:
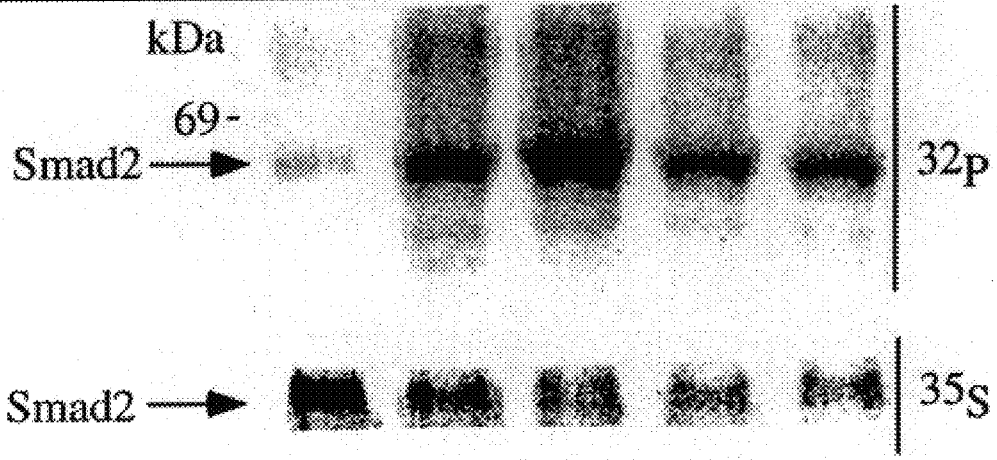
Figure 4C:
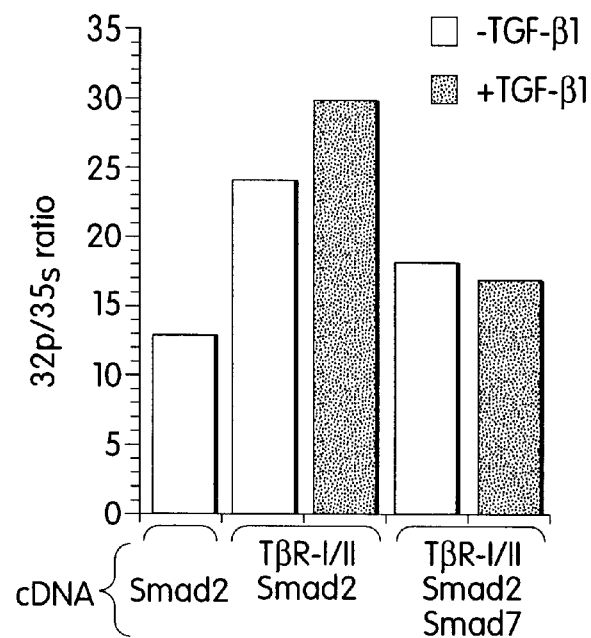
Figure 4E:
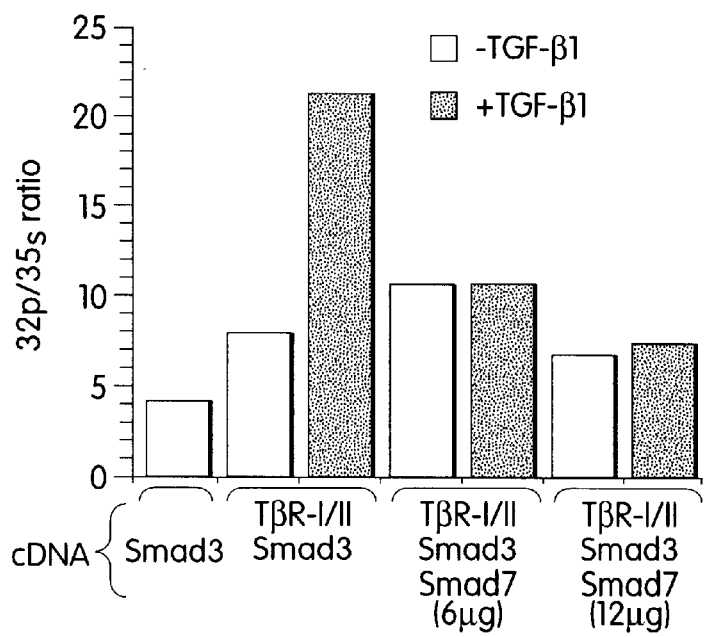

Phosphorylation of Smad2 and Smad3, but not Smad4, is induced after TGF-β stimulation (Eppert et al., Cell 86: 543–552, 1996; Zhang et al., 1996; Macías-Silva et al., 1996; Nakao et al., 1997; Lagna et al., 1996. It was investigated whether Smad7 is phosphorylated upon association with TGF-β receptors. COS cells were transfected with Smad7 (or for comparison with Smad2) in the absence or presence of receptors, labeled with [$^{32}$P]orthophosphate, and treated with TGF-β1. Cell lysates were subjected to immunoprecipitation with antisera against Smads or epitope tags, and the level of Smad phosphorylation was determined. Expression of type I receptors and Smads was analyzed by immunoprecipitation on aliquots of cell lysates, which had been labeled with [$^{35}$S]-methionine/cysteine. The $^{32}$P- or $^{35}$S-radioactivity associated with Smad2in (FIG. 4b) or Smad3 in (FIG. 4d) were quantitated by using a FujiX Bio-Imager and the 32P/$^{35}$S-ratio calculated (FIGS. 4c and e, respectively). Representative results of three independent experiments are shown. As expected, Smad2 phosphorylation was increased upon coexpression with receptors, and addition of TGF-β1 led to a further increase of Smad2 phosphorylation. However, no (or only very weak) phosphorylation of Smad7 was observed in cells transfected with constitutively active forms of TβR-I and ActR-IB or in cells transfected with wild-type TβR-I and TβR-II after stimulation with ligand (FIG. 4a). Thus, in spite of its direct association with TβR-I, Smad7 is not a direct substrate for the TβR-I kinase. Notably, Smad7 lacks the conserved SS(M/V)S C-tail sequence motif (FIG. 1a), which in the case of Smad2 (Macías-Silva et al., 1996) and Smad1 (Kretzschmar et al., Genes Dev. 11: 984–995, 1997) are phosphorylated by type I receptor kinase.

Example 4
Smad7 Reduces Phosphorylation of Smad Proteins

Figure 4D:
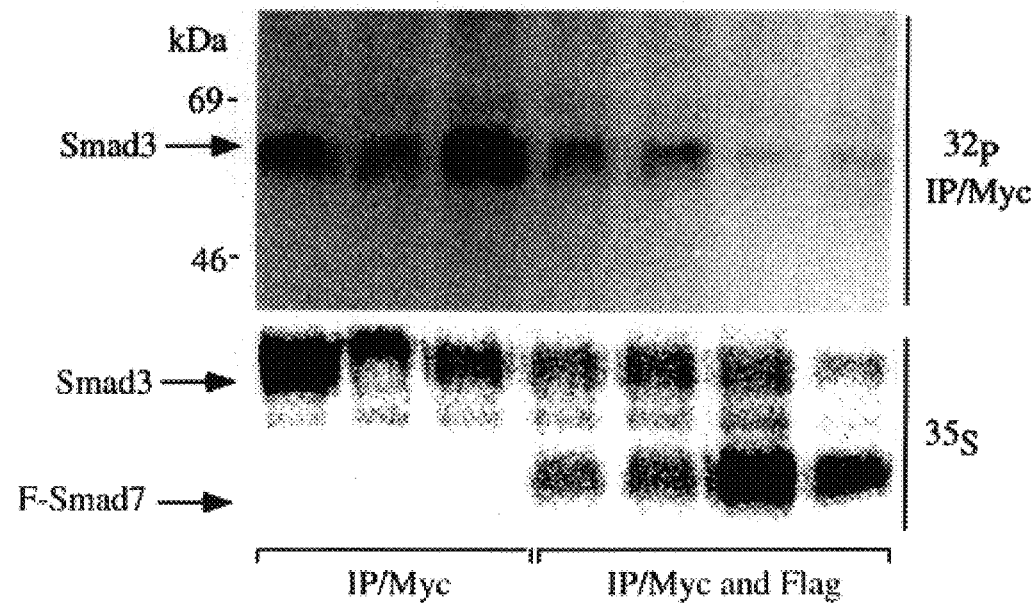

Smad7 may exert its negative role in TGF-β signaling by interfering with activation of other Smads. Therefore it was examined whether Smad7 affects the phosphorylation of Smad2 and Smad3 using [$^{32}$P]orthophosphate-labeled COS cells transfected with TGF-β receptors and Smads. COS cells were transfected with F-Smad7 or Smad2 (FIG. 4a), Smad2 alone or together with Smad7 (FIG. 4b), and N-terminally Myc-tagged Smad3 (M-Smad3) alone or together with F-Smad7 (FIG. 4d) in the absence or presence of wild-type or constitutive active (c.a.) receptors, whereafter cells were labeled with [$^{32}$P]orthophosphate. C-terminally HA-tagged type I receptors were used. Interestingly, Smad7 abolished the TGF-β1-induced phosphorylation of Smad2 (FIGS. 4b,c) and Smad3 in dose-dependent manner (FIGS. 4d,e). A Smad7 level twice as high as Smad3 appeared sufficient to cause a significant decrease in TGF-β-induced receptor-mediated Smad3 phosphorylation. As previously reported (Macías-Silva et al., 1996; Nakao et al., 1996), it was found that Smad2 and Smad3 become phosphorylated when overexpressed in COS cells. For Smad2 this receptor-independent phosphorylation does not occur at the SSMS motif in the C-terminal tail (Macías-Silva et al., 1996), and may possibly occur via non-receptor kinases. Smad7 appears not to block this receptor-independent phosphorylation. Since activation of Smad2 and Smad3 is essential for optimal TGF-β signaling (Zhang et al., 1996; Macías-Silva et al., 1996; Nakao et al., 1997; Lagna et al., 1996; Kretzschmar et al., 1997), the inhibition of their phosphorylation provides a mechanistic explanation for the antagonistic effect of Smad7. The association of Smad7 with TβR-I suggests that it may compete with Smad2 and Smad3 for receptor binding. In accordance with this notion, co-transfection of Smad2 or Smad3 with Smad7 reduced the antagonistic effect of Smad7 in a TGF-β1-induced p3TPLux assay. In addition, it was determined that Smad7 not only inhibits TGF-β and activin signaling, but also blocks BMP signaling. Using methodology described herein, it was determined that Smad7 associated with BMPR-Is and inhibited phosphorylation of SmadI in cultured mammalian cells. In addition, injection of Smad7 RNA into ventral cells of Xenopus embryos phenocopies the effect of blocking the BMP signaling pathway, and led to formation of an incomplete secondary dorsal axis.

Example 5
Regulation of Smad7 Expression by TGF-β

Figure 5A:
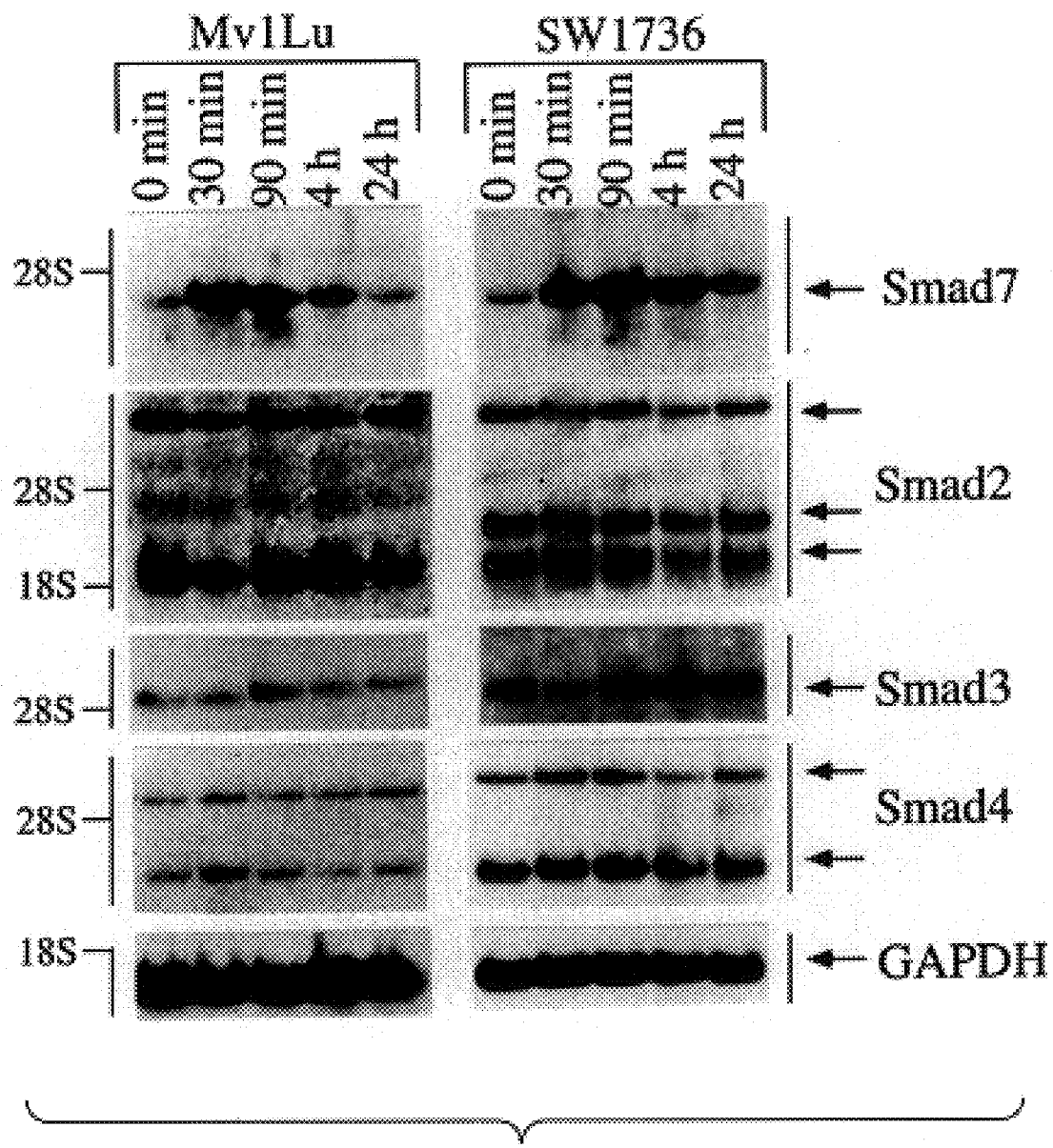
FIGS. 5A–5C show that Smad7 is an early response gene for TGF-β.
Figure 5B:
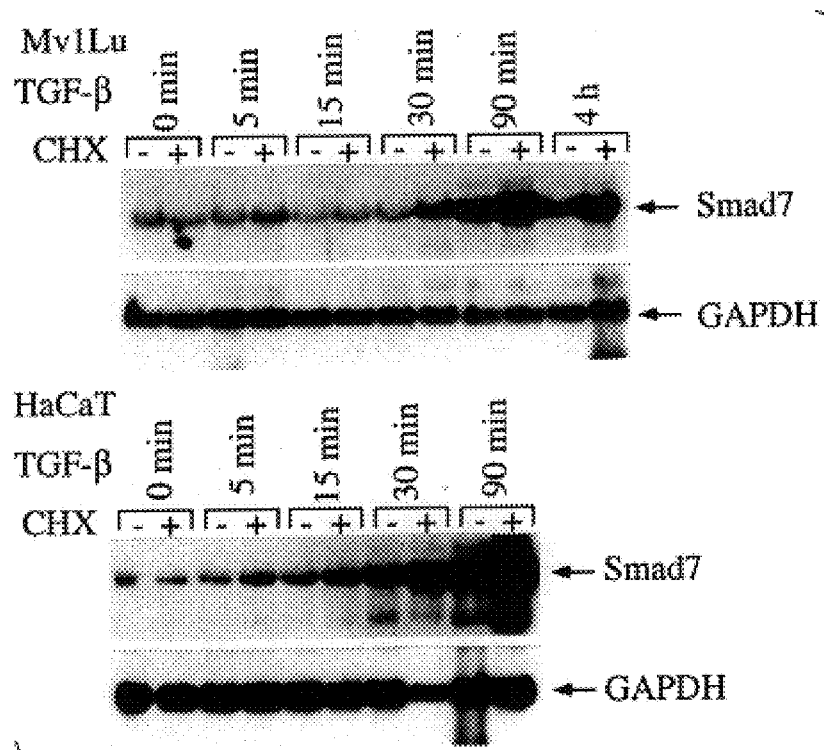
Figure 5C:
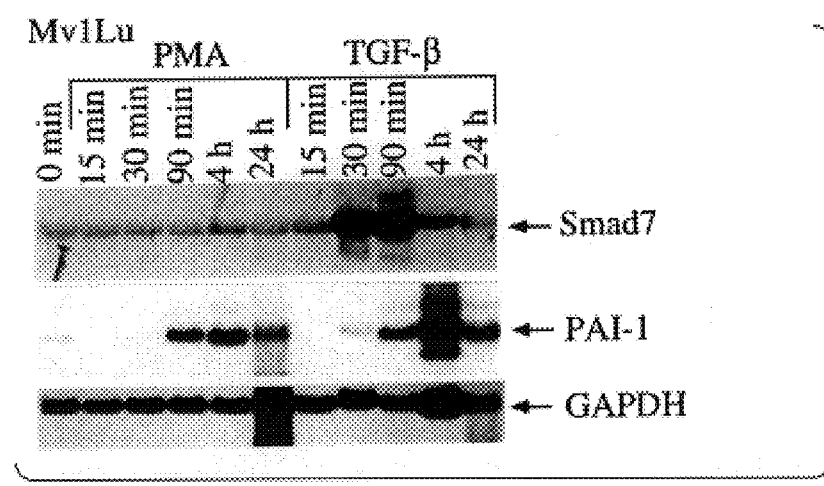

Regulation of Smad7 expression by signaling molecules may be used to effectively modulate TGF-β responses. Therefore, it was investigated whether the expression of Smad7, and for comparison Smad2, Smad3 and Smad4, were regulated by TGF-β1. Northern blots with 20 μg/lane total RNA from TGF-β1 stimulated Mv1Lu cells, SW1736 human anaplastic thyroid carcinoma cells and HaCat cells probed with Smad7 revealed that Smad7 mRNA was rapidly induced in response to 10 ng/ml TGF-β1 stimulation (FIGS. 5a,b). The amount of RNA loaded was checked by hybridization of filters to a glyceraldehyde-3-phosphate dehydrogenase (GAPDH) cDNA probe. In Mv1Lu cells, Smad7 mRNA was induced 4-fold after 30 min of TGF-β stimulation. Expression of Smad2, Smad3 and Smad4 upon TGF-β1 stimulation remained unchanged (FIG. 5a). Induction of Smad7 mRNA by TGF-β1 was observed in the presence of 20 μg/ml cycloheximide (CHX), indicating that de novo protein synthesis is not required for TGF-β1-mediated induction of Smad7. In fact, Smad7 mRNA was superinduced in the presence of TGF-β1 and 20 μg/ml CHX added 30 min. prior to TGF-β1 (FIG. 5b). This is likely caused by increase in mRNA stability or loss of transcriptional repressors by CHX. Treatment with CHX alone only slightly increased the basal Smad7 mRNA level. In contrast, 10 nM PMA, which like TGF-β1 stimulates PAI-1 expression and inhibits the growth of Mv1Lu cells, did not induce Smad7 expression (FIG. 5c). In Mv1Lu cells lacking functional TβR-I (R mutant), TGF-β1 had no effect on Smad7 mRNA expression. Taken together these data indicate that Smad7 is an immediate-early response gene for TGF-β1, and activated complexes of Smad2, Smad3 and Smad4 may directly and/or in combination with DNA binding cofactors act on the Smad7 promoter. The intracellular antagonist Smad7 may thus act in a negative feedback loop to regulate the intensity or duration of the TGF-β signal.

Example 6
Smad7 Interacts with BMP Receptor Complexes and Inhibits BMP-Mediated Signaling.

Figure 6A:
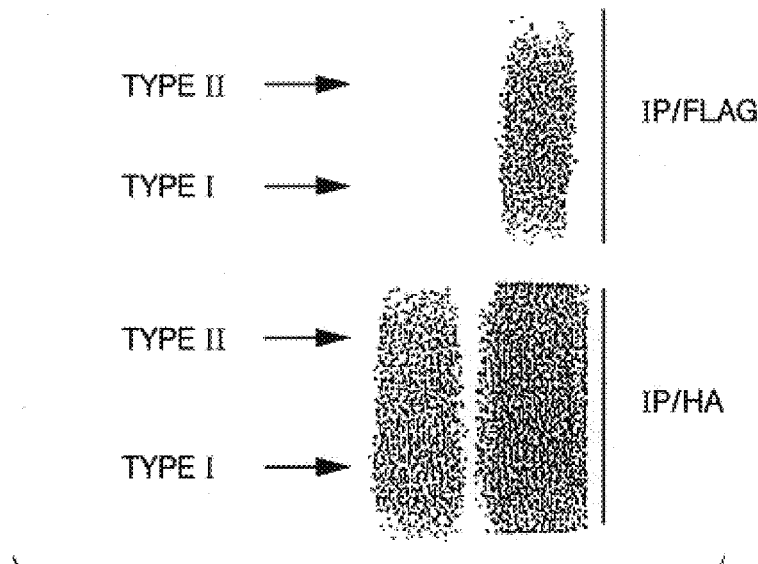
FIGS. 6A–6F demonstrate the association of Smad7 with BMP and activin receptor complexes.
Figure 6B:
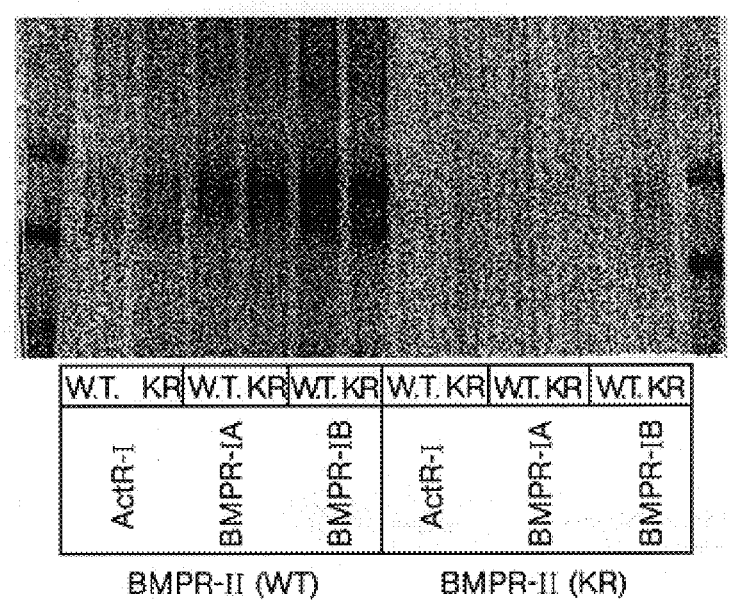
Figure 6C:
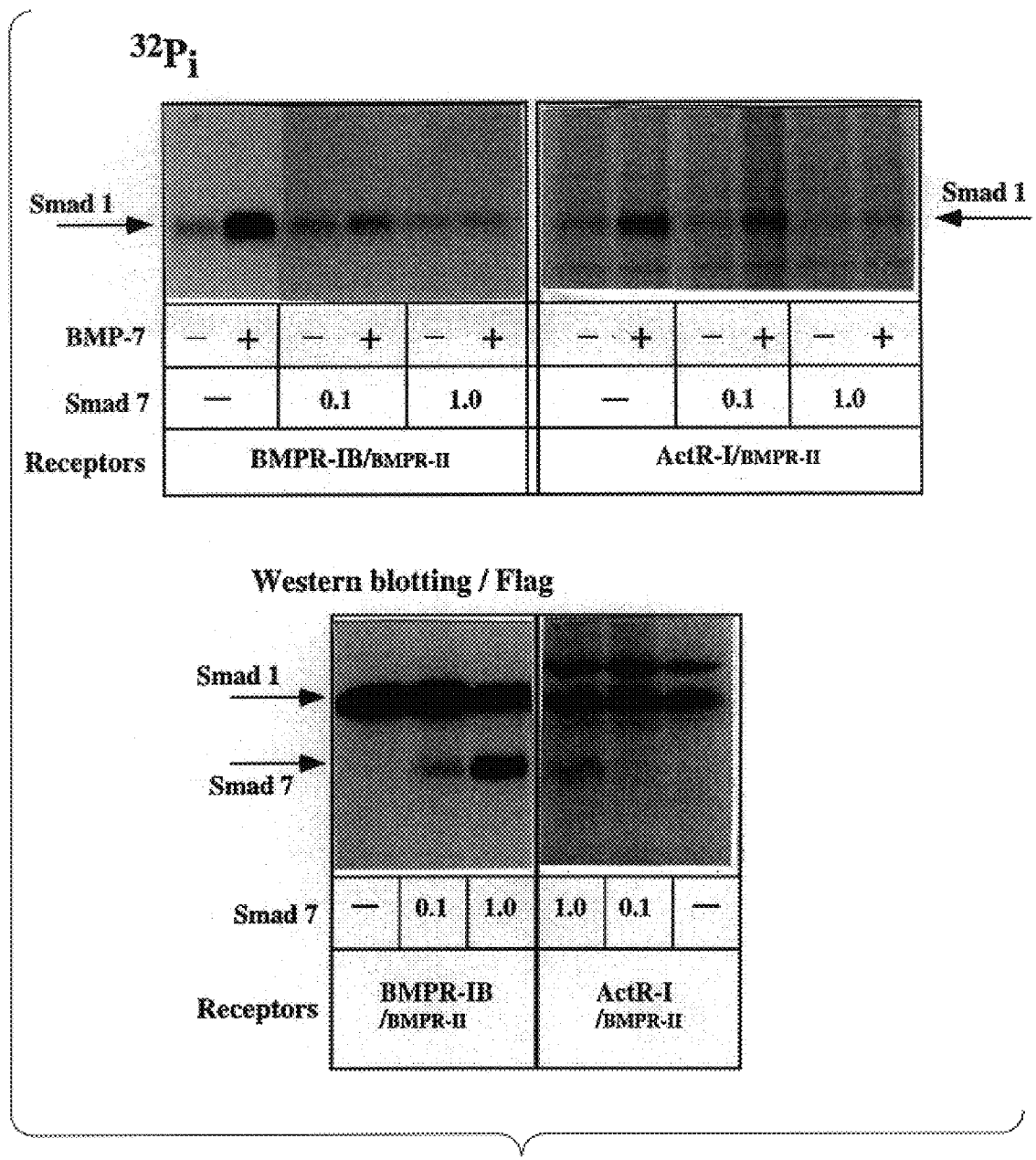
Figure 6D:
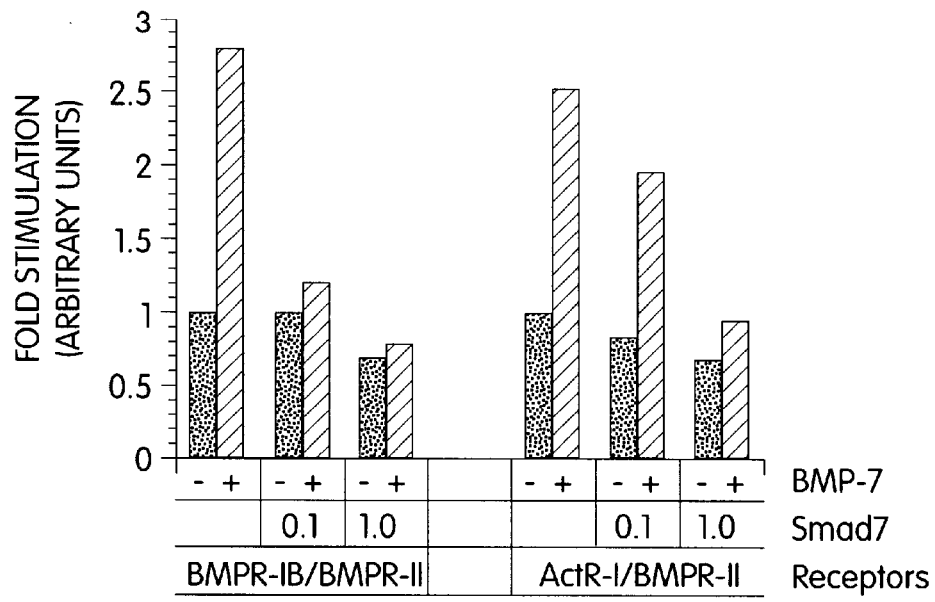
Figure 6F:
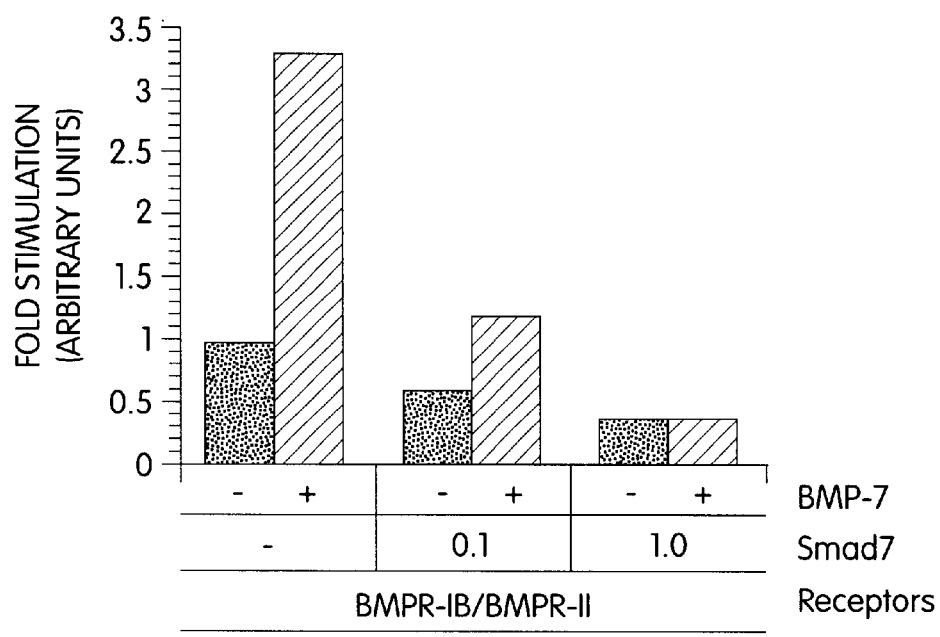
Figure 6E:
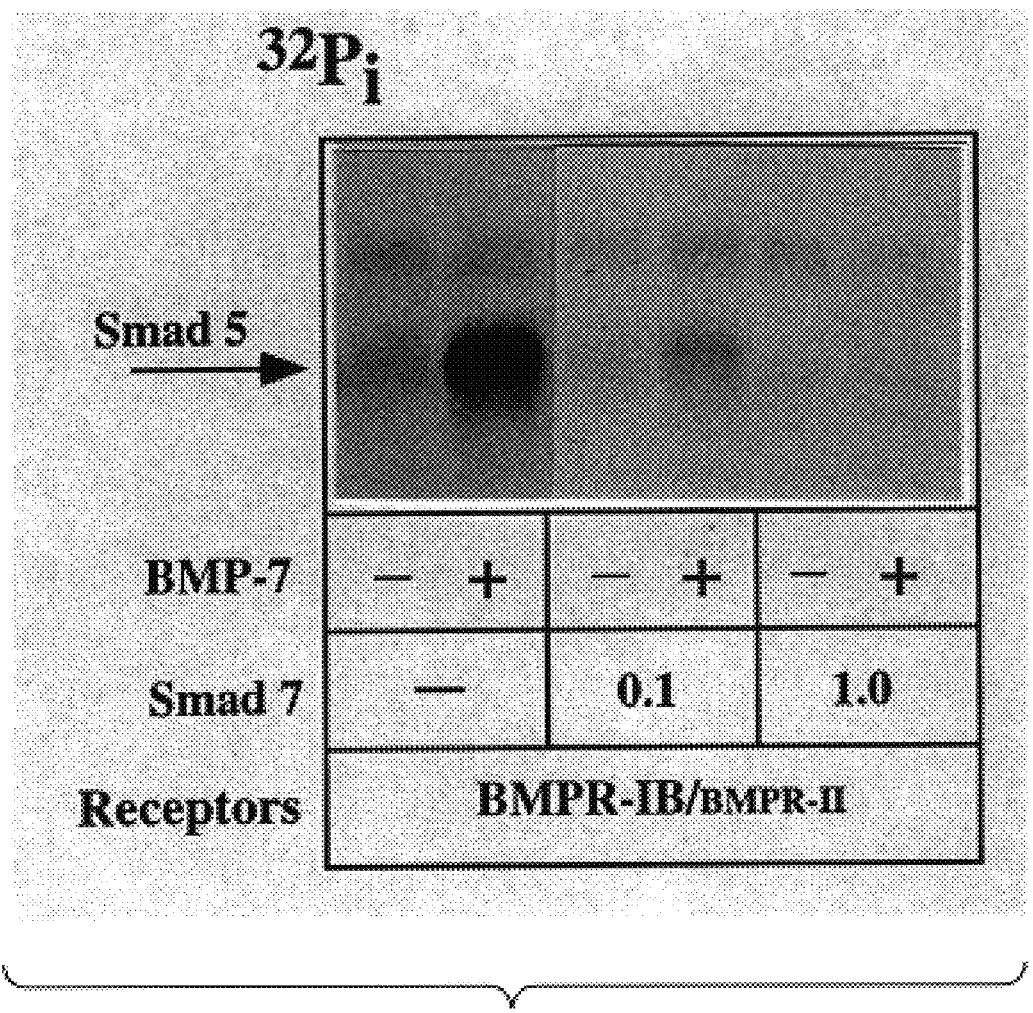

To determine if Smad7 associates with the BMP receptor complex, COS cells were transfected with the BMP receptors BMPR-IA, BMPR-IB, or ActR-I (wild-type or kinase-deficient mutant) tagged at C-terminus with HA epitope, and BMPR-II (wild-type or kinase-deficient mutant), in the absence or presence of N-terminally Flag-tagged Smad7 (F-Smad7). The receptors were covalently affinity labeled with $^{125}$I-BMP-7, and cell lysates were subjected to immunoprecipitation with Flag antibody to immunoprecipitate F-Smad7. Immunoprecipitates were analyzed by SDS-PAGE and FujiX Bio-Imager. Expression of receptors and F-Smad7 (not shown) after transfection was determined by immunoprecipitation with HA-antisera on aliquots of cell lysates, and by immunoprecipitation with Flag antibody on lysates from [$^{35}$S]methionine/cysteine labeled transfected cells. As shown in FIGS. 6A–F, TGF superfamily receptors coimmunoprecipitated with F-Smad7. Therefore, Smad7 associated with BMPR-IA and BMPR-IB, and less efficiently with ActR-I receptors. As shown in FIG. 6B, no interaction was observed between Smad7 and heteromeric complexes of a kinase-deficient type II receptor and a wild-type or a kinase-deficient type I receptor. Thus Smad7 only interacts with type I receptors which are phosphorylated by the type II receptor (i.e. activated). Among the tested type I receptors, Smad7 preferentially interacts with BMPR-IA, BMPR-IB, TβR-I and likely ActR-IB, and less efficiently with ActR-I. In addition, the effect of Smad7 on BMPR-IB- and ActR-I-mediated phosphorylation of Smad1 or Smad5 was examined (FIG. 6C–F). FIG. C shows that Smad 7 inhibits BMPR-IB- and ActR-I-mediated phosphorylation of Smad1. COS cells were transfected with F-Smad1 alone or together with F-Smad7 in the presence of type I receptors (BMPR-IB or ActR-I) and BMPR-II in the absence or presence of BMP-7, whereafter cells were labeled with [$^{32}$P]orthophosphate and immunoprecipitated with Flag antisera. Expression of F-Smad1 and F-Smad7 was determined by immunoblotting with Flag on aliquots of cell lysates. FIG. 6D shows that the $^{32}$P-radioactivity associated with Smad1 in FIG. 6C as quantified by using a FujiX Bio-Imager and plotted. FIG. 6E shows that Smad7 inhibits BMPR-IB phosphorylation of Smad5. COS cells were transfected with F-Smad5 alone or together with F-Smad7, in the presence of BMPR-IB and BMPR-II; cells were incubated in the absence or presence of BMP-7, whereafter they were labeled with [$^{32}$P]orthophosphate and subjected to immujnoprecipitation with Flag antisera. FIG. 6F shows the $^{32}$P-radioactivity associated with Smad5 in FIG. 6E as quantified using a FujiX Bio-Imager and plotted. COS cells were transfected with cDNAs encoding BMP receptors and Smad1 or Smad5 in the absence or presence of Smad7. The phosphorylation level of Smad1 or Smad5 was examined by [$^{32}$1']orthophosphate labeling and immunoprecipitation from cell lysates using Smad antisera. Smad7 potently inhibited BMPR-IB-mediated phosphorylation of Smad1 and Smad5 in a dose dependent manner (FIGS. 6C–F). In addition, Smad7 inhibited ActR-I-mediated phosphorylation of Smad1 (FIGS. 6C, D). The specificity of the interaction based on the phosphorylation of the type I receptor by type II receptor kinase strongly suggests physiological importance of the interaction. Phosphorylation may induce a conformational change that is required for Smad7-type I receptor interaction.

Figure 7A:
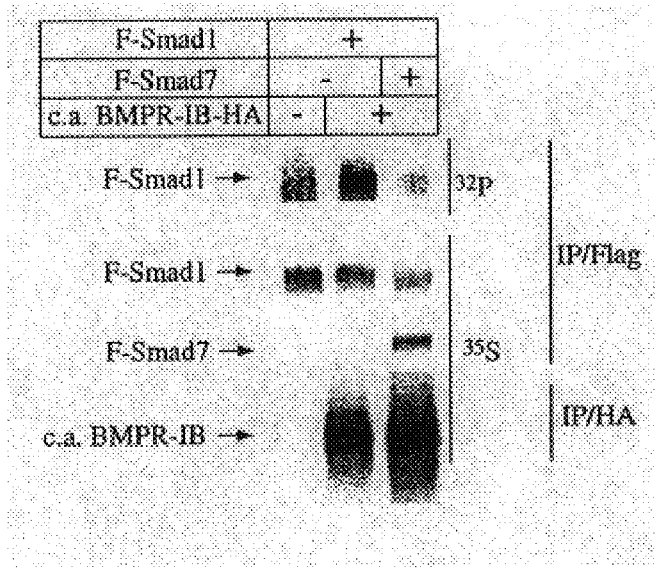
FIGS. 7A–7C show that Smad7 inhibits BMP- and activin-receptor mediated phosphorylation of Smad1 or Smad5.
Figure 7B:
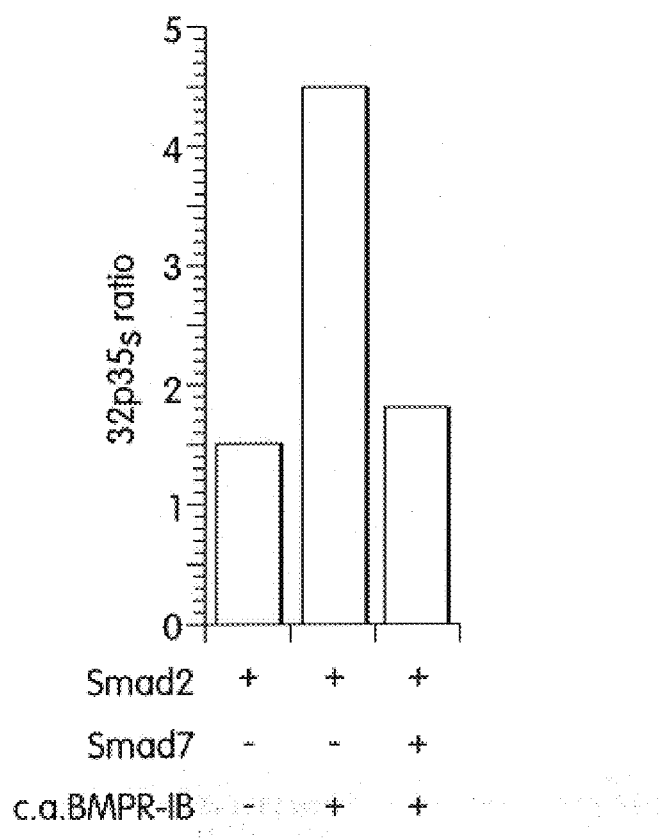
Figure 7C:
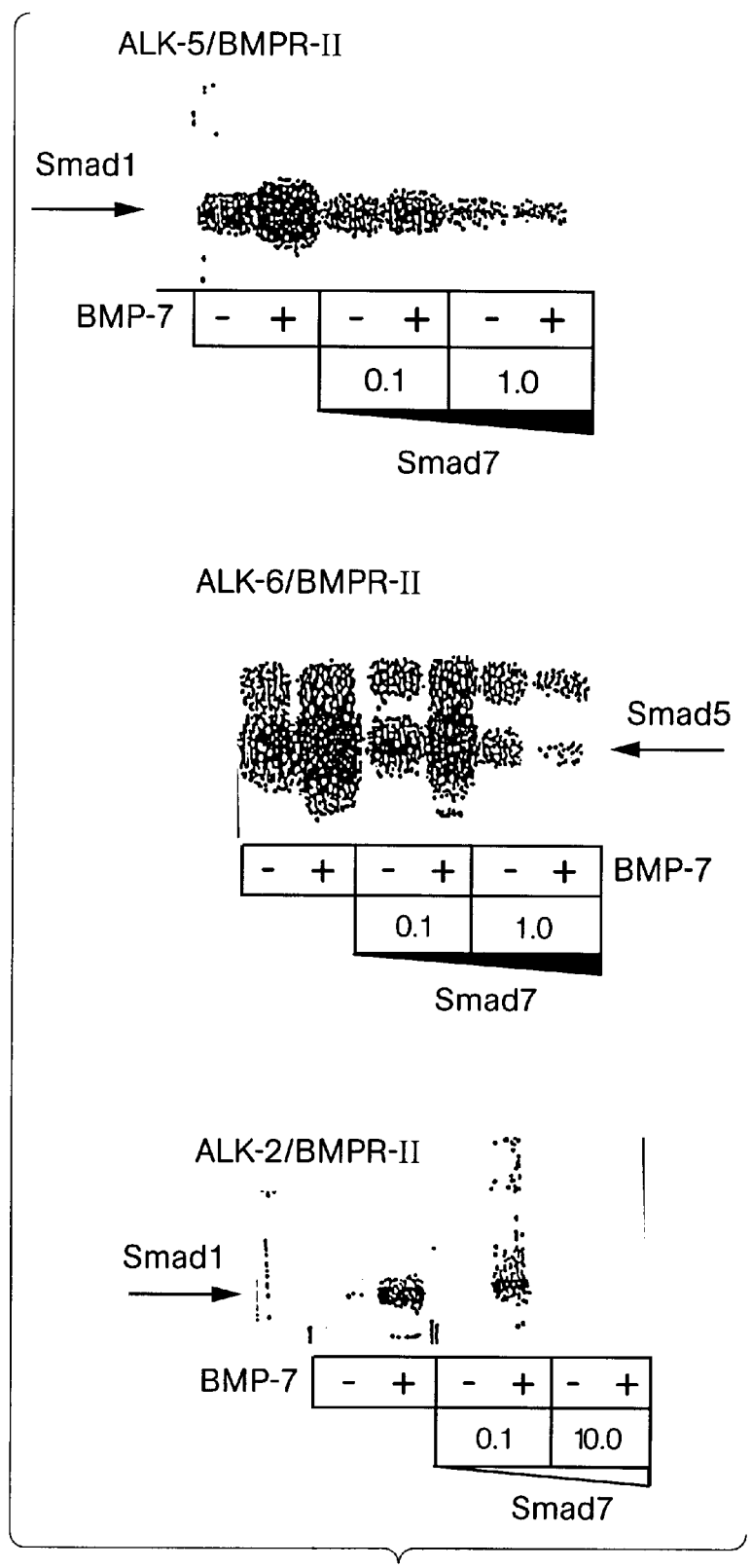

To determine if Smad7 inhibits BMP-mediated phosphorylation of pathway specific Smads, COS cells were transfected with F-Smad1 or F-Smad5, alone or together with F-Smad7 in the absence or presence of constitutive active (c.a.) BMPR-IB (FIG. 7A), or alone or together with F-Smad7, type I receptors and BMPR-II in the absence or presence of BMP-7 (FIG. 7C), whereafter cells were labeled with [$^{32}$P]-orthophosphate. The amount of transfected Smad7 is indicated in FIG. 7C (0.1 or 1.0 microgram). Cell lysates were subjected to immunoprecipitation with antisera against Smads, and the level of phosphorylation determined. Expression of Smads and BMPR-IB was analyzed by immunoprecipitation with antisera directed towards epitope tags on aliquots of cell lysates, which had been labeled with [$^{35}$S]methionine/cysteine. In FIG. 7B, the $^{32}$P or $^{35}$S-radioactivity associated with SmadI were quantitated by using FujiX Bio-Imager and the $^{32}$P/$^{32}$S-ratio calculated. FIG. 7 shows that Smad7 potently inhibited phosphorylation of by BMPR-IB-mediated Smad1 or Smad5 phosphorylation in a dose-dependent manner. Consistent with the differential receptor binding, BMPR-IB-mediated Smad phosphorylation was more efficiently inhibited by Smad7 than was ActR-I-mediated Smad phosphorylation.

Example 7

Analysis of Smad7 N-terminal and C-terminal Domain Function

Figure 8A:
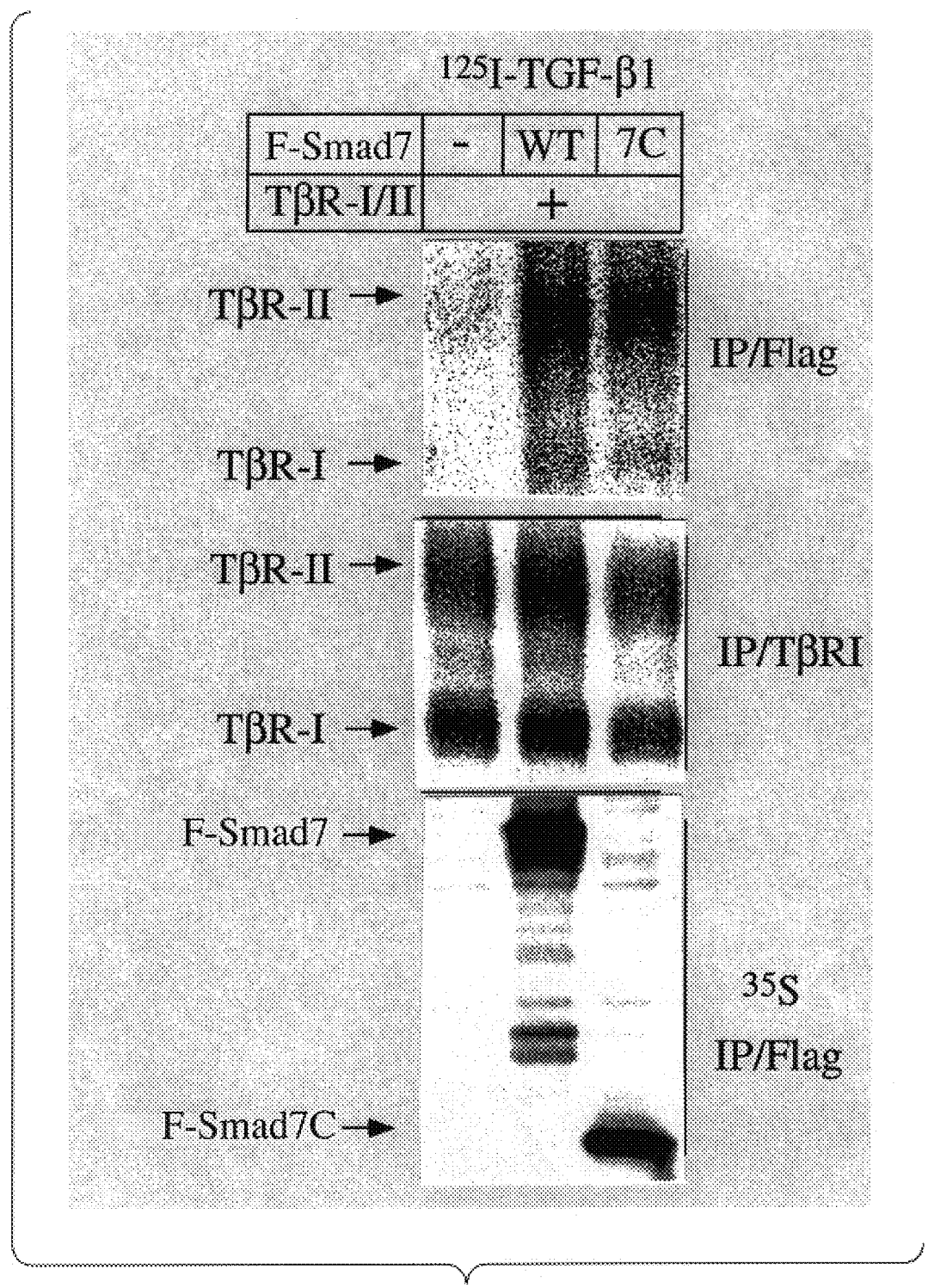
FIGS. 8A, 8B1, 8B2, 8C, 8D, and 8E demonstrates that the C-terminal domain of Smad7 associates with the TGF-β seceptor complex and that Smad8 and the N-terminal and C-terminal domains of Smad7 inhibit TGF-β signalling.
Figures 1, 8B:
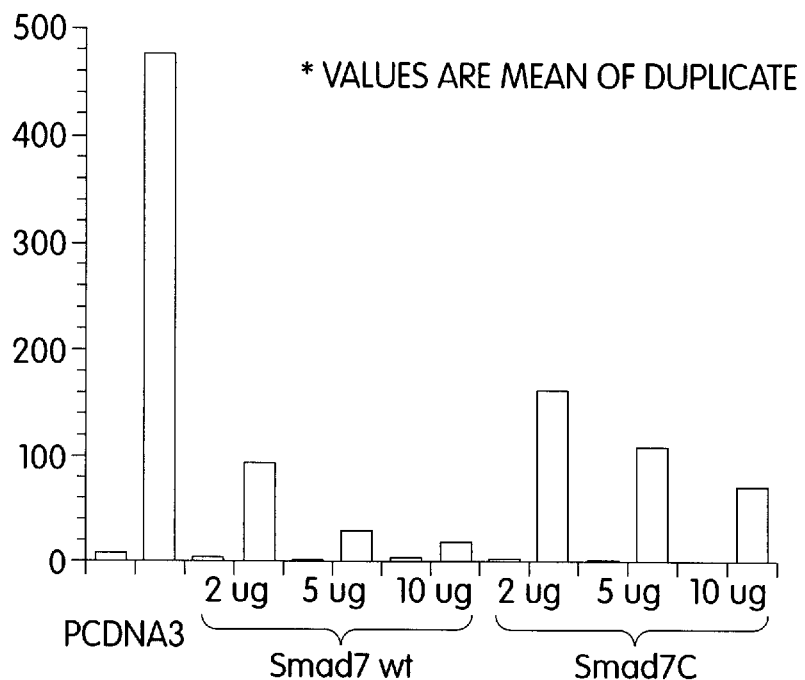
Figures 2, 8B:
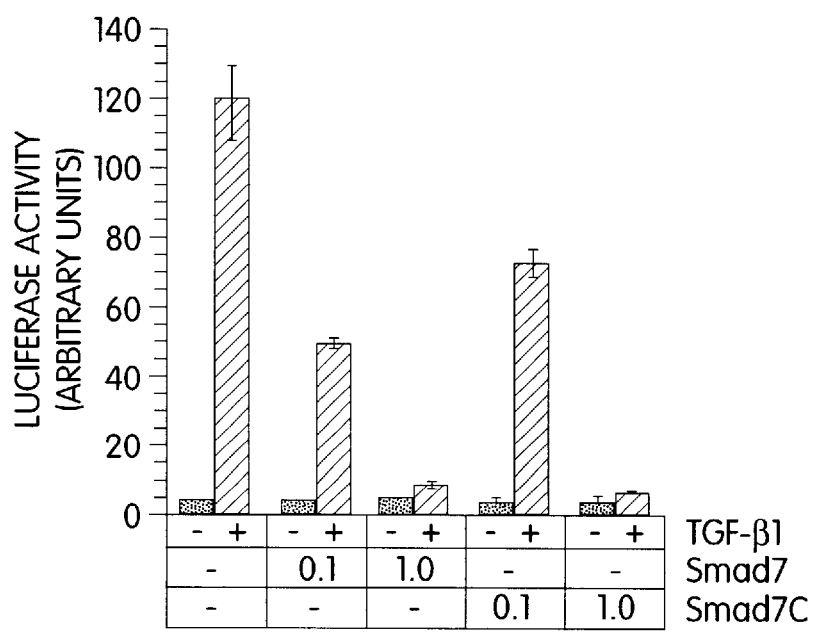

To determine if the C-terminal domain of Smad7 associates with the TGF-β receptor complex, COS cells were transfected with wild-type N-terminally tagged mouse Smad7 (F-mSmad7) or a N-terminally Flag tagged mouse Smad7 C-terminal domain (amino acids 204–426 of mSmad7) in combination with wildtype TGF-β receptors. The receptors were covalently affinity labeled with $^{125}$I-TGF-β1. Immunoprecipitates were analyzed by SDS-PAGE and FujiX BioImager. Expression of receptors and Smad7 after transfection was determined by immunoprecipitation with VPN antisera against TβR-I on aliquots of cell lysates, and by immunoprecipitation with Flag antibody on cell lysates from $^{35}$S methionine/cysteine labeled transfected cells. As shown in FIG. 8A, the TGF-β receptor complex coprecipitates with Smad7 C-terminal domain. Therefore, the Smad7 C-terminal domain associates with TGF-β receptors. Next, the C-terminal domain was tested in an assay of TGF-β-induced p3TPLux response, as described above. As shown in FIG. 8B, the C-terminal domain inhibits, albeit less efficiently as wild-type Smad7, the TGF-B-induced p3TPLux response. FIG. 8B, panel 2 shows that transfection of Smad7C blocks TGF-β-induced p3TPLux transcriptional response, but less efficiently than will-type Smad7.

Figure 8C:
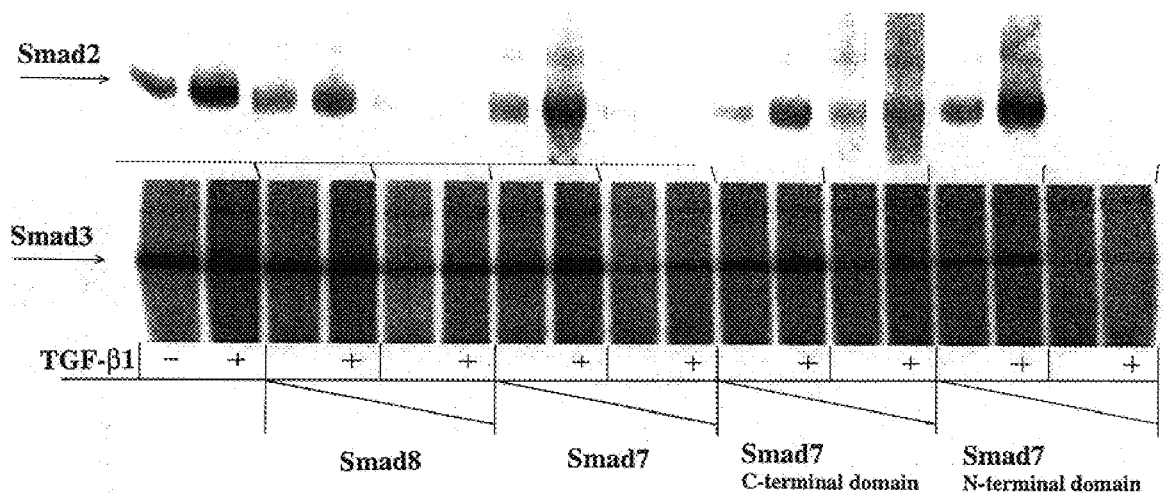

The inhibitory effect of N- and C-terminal Smad7 domains and Smad8 on TGFβ superfamily receptor responses was tested. Smad8 and Smad7 deletion constructs were tested for effects on TβR-I-mediated phosphorylation of Smad2 or Smad3. COS cells were transfected with TβR-I and TβR-II and indicated Smads. Phosphorylation of Smads was determined by a $^{32}$P orthophosphate labeling assay. FIG. 8C shows that Smad8 and N- and C-terminal (MH2) domains of Smad7 each inhibited TβR-I-mediated phosphorylation of Smad2 or Smad3. The effect of the C-terminal domain was achieved at lower expression levels than the N-terminal domain. Consistent with the ability of the C-domain of Smad7 to inhibit TβR-I-mediated phosphorylation of Smad2, this domain was sufficient to inhibit TGF-β-induced transcriptional activation, although it was less efficient at doing so than was wild-type Smad7 (FIG. 8B, panel 2). Deletion of the last 19 amino acids residues completely abrogated the ability of the Smad7 C-domain to inhibit TGF-β-induced transcriptional activation of the 3TP promoter.

Figure 8D:
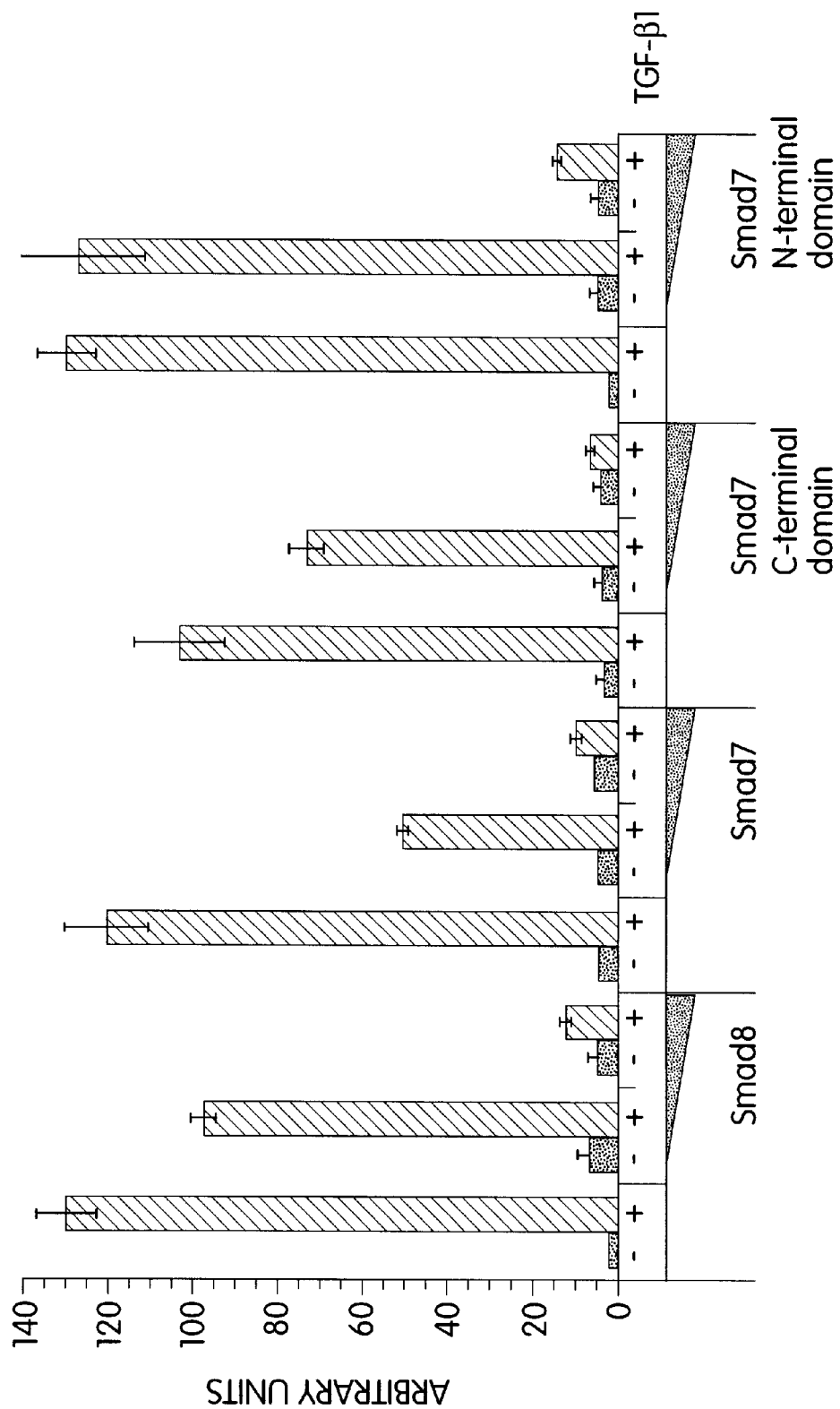

FIG. 8D shows the inhibitory effect of Smad7 N- and C-terminal domains and Smad8 (as compared to Smad7 wild-type) on TGF-β receptor mediated p3TPLux transcriptional response. Mv1Lu cells were transfected with p3TP-Lux reporter construct with or without different quantities of inhibitory Smads. The induction of luciferase expression upon cell incubation with TGF-β was measured. Consistent with their differential phosphorylation inhibitory effects, Smad8 and the Smad7 domains inhibited the TGF-β mediated transcriptional response of the reporter gene.

Figure 8E:
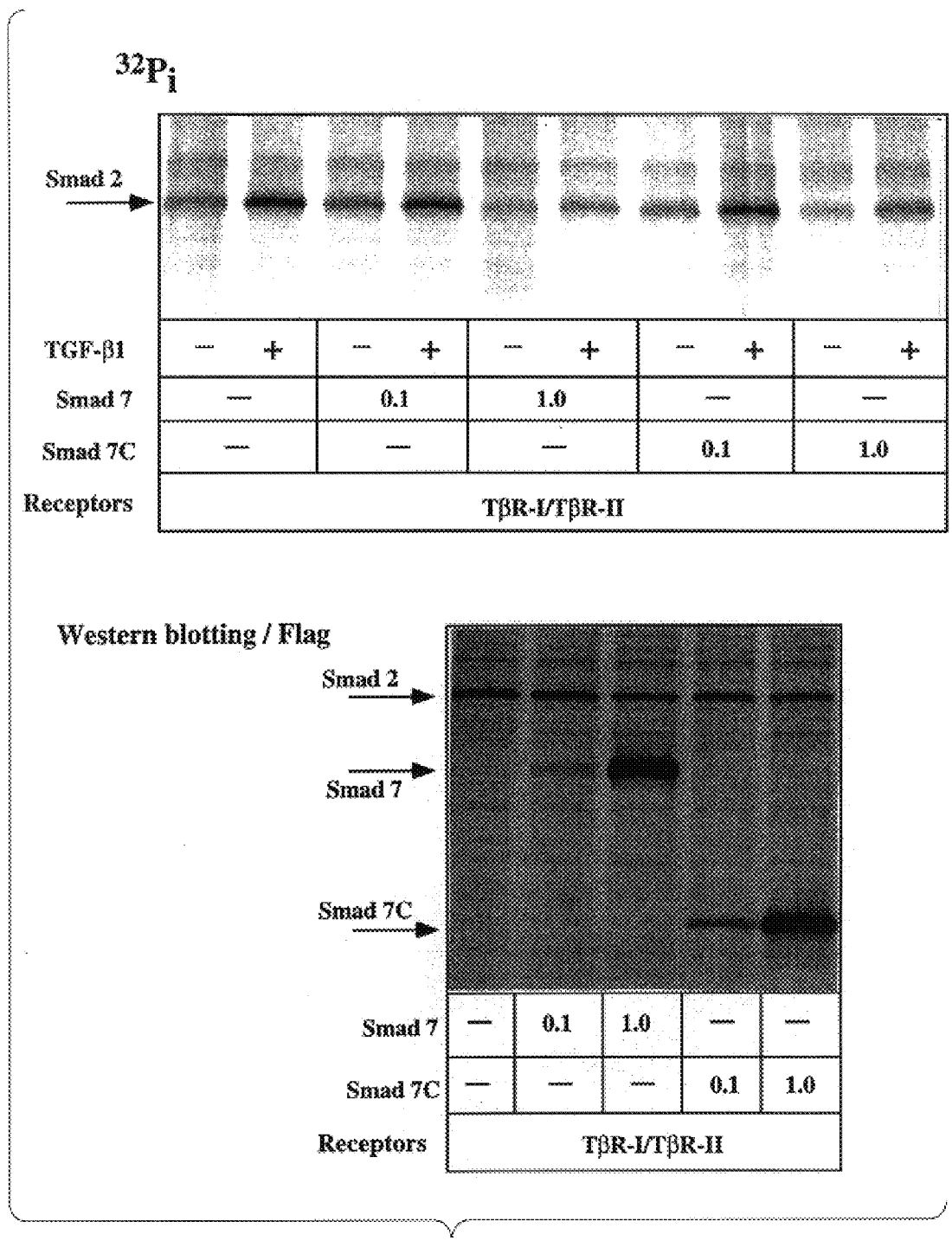

FIG. 8E shows that Smad7C inhibits TβR-I-mediated phosphorylation of Smad2, but less efficiently than wild-type Smad7. In the absence of inhibitory Smad, TGF-β1 stimulated a 1.6-fold increase in Smad2 phosphorylation level, which was completely blocked by cotransfection with 1 μg wild-type Smad7, whereas in the presence of 1 μg Smad7C a 1.2-fold increase in TGF-β-mediated Smad2 phosphorylation was observed. COS cells were transfected with F-Smad2 alone or together with F-Smad7C or wild-type F-Smad7 in the presence of BMPR-IB and BMPR-II; cells were then incubated in the absence or presence of BMP-7, whereafter they were labeled with [$^{32}$P] orthophosphate and subjected to innmunoprecipitation with Flag antisera. Expression of F-Smad2, F-Smad7 and F-Smad7C was determined by immunoblotting with Flag on aliquots of cell lysates.

Example 8

Smad6 is Highly Conserved and Most Closely Related to Smad7

Figure 9B:
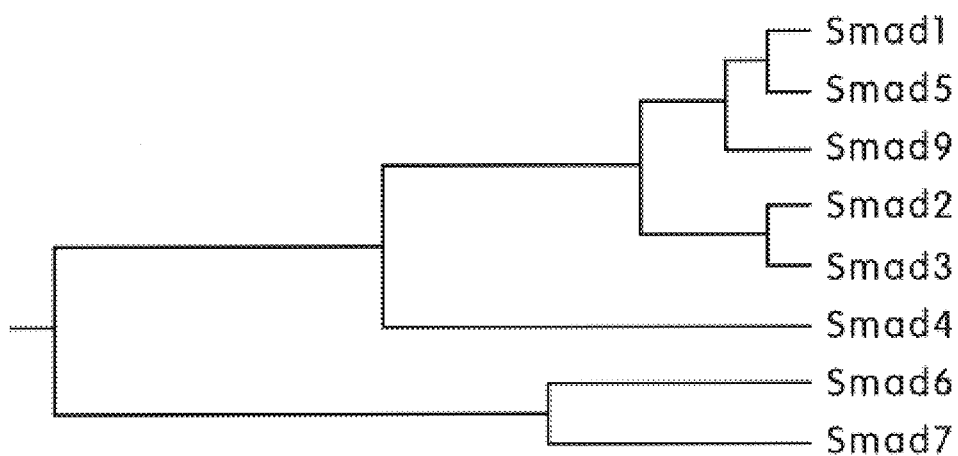

A database search for human and mouse sequences related to Smad7 revealed the existence of an expressed sequence tag (EST; Genbank accession number N95582) corresponding to a novel human Smad. By screening of a human placenta cDNA library we obtained a 3.2 kb cDNA clone. The entire coding region of this clone was sequenced using ABI Prism 310 Genetic Analyzer, and sequence analysis was performed with DNASTAR. Sequence analysis revealed 92% amino acid similarity to mouse Smad6 (Imamura et al., *Nature*, 389:622–626, 1997), and therefore this gene was termed human Smad6 (hSmad6) (FIG. 9A). FIG. 9A shows sequence comparison of human and mouse Smad6 and human Smad7. Identical residues are boxed. The borders of the Mad-homology MH2 domain are indicated by arrows. The Genbank accession number for human Smad6 is AF043640. The sequence identity between human and mouse Smad6 is lower compared to that observed with other Smads, e.g., human and mouse Smad7 are 98% identical (Hayashi et al., 1997; Nakao et al., 1997). FIG. 9B shows pairwise alignment relationship between hSmad1 through hSmad7 and hSmad9. Among the human Smads identified to date, hSmad6 is most closely related to hSmad7 (41% overall sequence identity). Like the N-terminal domain of Smad7, the N-terminal domain of Smad6 shows very weak similarity to MH1 domains from Smad1 through Smad5. Notably hSmad6 lacks the conserved SS(MNV)S motif in its carboxy-terminal tail, which in the case of pathway-restricted Smads is phosphorylated by appropriate type I receptor kinases. Recently Hata et al. reported a hSmad6 sequence (accession number AF035528) (Hata et al., *Genes Dev.*, 12:186–197, 1998). Comparison of the two sequences reveals one nucleotide difference in the coding region resulting in one amino acid difference (codon 21 in AF043640 is predicted to be an aspartic acid residue).

Example 9

Smad6 and Smad7 Expression in Lung Cancer Cell Lines

Figure 9C:
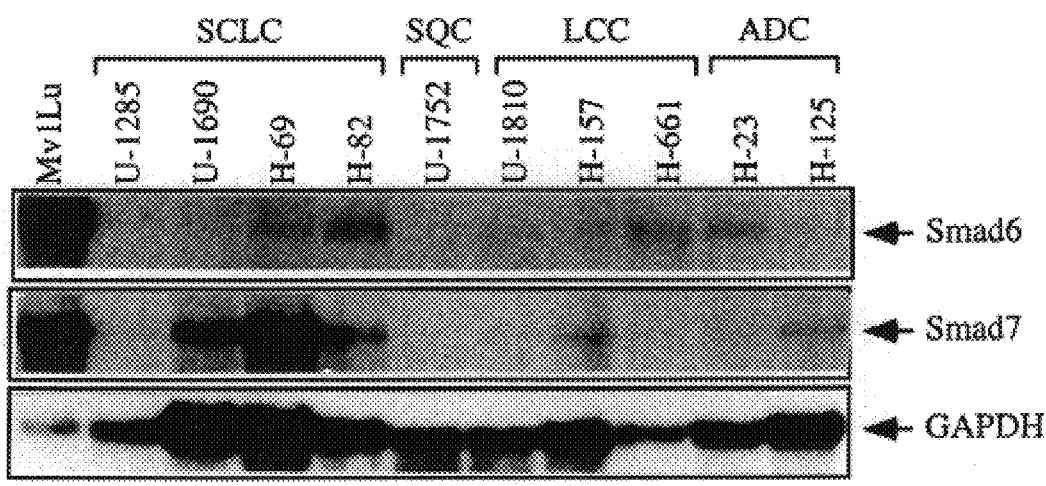

As previously reported, the distribution of Smad6 mRNA in various human tissues revealed that Smad6 was broadly expressed in various human tissues. One Smad6 transcript of approximately 3 kb was detected (Imamura, T., et al. 1997). Interestingly, the expression profiles of Smad6 and Smad7 (Nakao et al., 1997) were very similar with the highest expression in the lung. Therefore, a panel of 10 different lung carcinoma cell lines (four SCLC and six non-SCLC) was examined for Smad6 and Smad7 mRNA expression (FIG. 9C). The highest Smad6 mRNA expression was detected in the SCLC cell lines H-69 and H-82, and in the non-SCLC cell lines H-661 and H-23, whereas the SCLC cell line U-1690, H-69 and H-82, and the non-SCLC cell lines H-157 and H-125 expressed the highest levels of Smad7 mRNA. Thus, the two genes are differently expressed, and no correlation was observed between Smad6 and Smad7 expression in these cells.

Example 10

TGF-β Family Members Induce Smad6 and Smad7 mRNA in Mv1Lu and HaCat Cells

Figures 1, 10A:
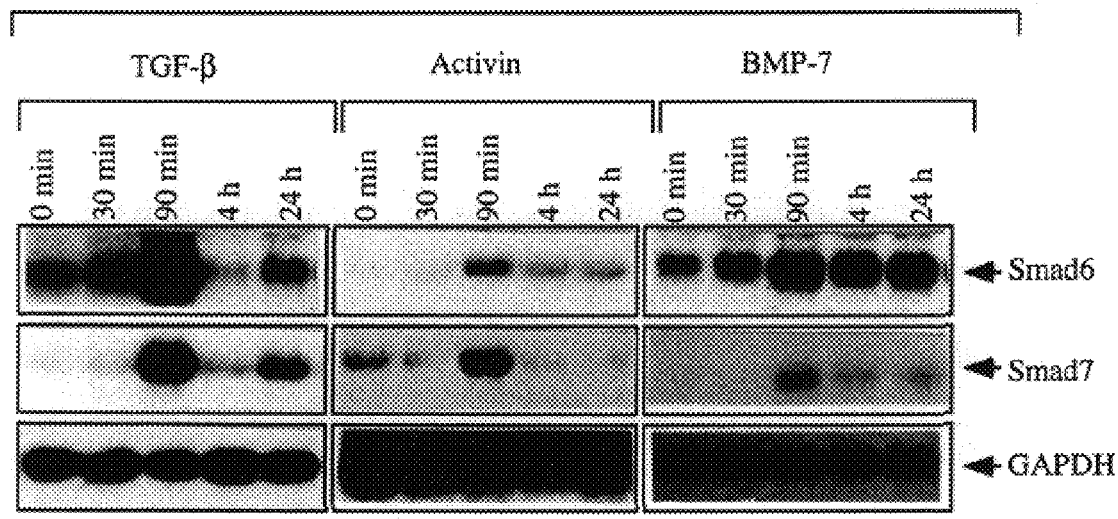
Figures 2, 10A:
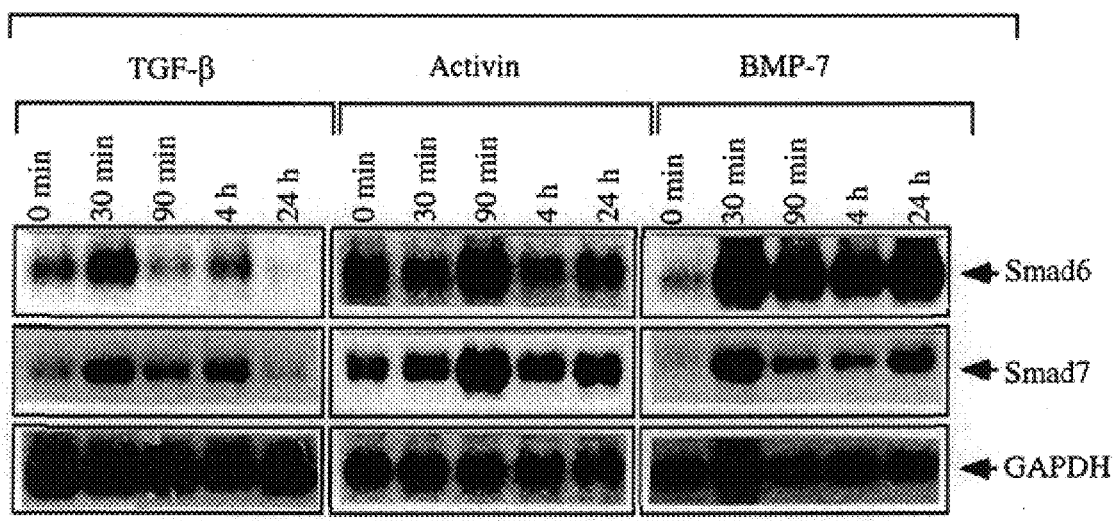

Mink lung epithelial (Mv1Lu) and human keratinocyte (HaCat) cell lines are responsive to TGF-β1, activin and BMP-7 (Yashamita et al. *J. Cell Biol.* 130:217–226,1995). Smad7 mRNA is rapidly included by TGF-β1 (Nakao, A., 1997). Northern blot analysis of Smad6 and Smad7 expression was performed on RNA prepared from Mv1Lu and HaCat cells stimulated with TGF-β1 (10 ng/ml), activin (50 ng/ml) and BMP-7 (500 ng/ml). Phosphor Imager quantitation revealed that (after 90 min of ligand stimulation and normalizing with GAPDH mRNA expression level) in Mv1Lu cells (FIG. 10A Panel 1), TGF-β1, activin and BMP-7 induced Smad6 mRNA expression 6-, 2- and 3-fold, respectively, and induced Smad7 mRNA expression 5-, 2-, and 3-fold, respectively, and in HaCat cells (FIG. 10A Panel 2), TGF-β1, activin and BMP-7 induced Smad6 mRNA expression 4-, 2- and 12-fold, respectively, and included Smad7 mRNA expression 6-, 3-, and 6-fold, respectively. Both genes were rapidly induced by all three ligands (FIG. 10A). Smad6 and Smad7 were induced with similar kinetics by TGF-β and activin, with a major peak of expression after 90 min of stimulation. A second peak of Smad6 and Smad7 mRNA expression was observed after 24 hr of stimulation Mv1Lu cells, in particular after TGF-β1 stimulation (FIG. 10A). There was a difference in the BMP7-induced mRNA expression profiles for Smad6 and Smad7 in Mv1Lu cells: whereas Smad7 mRNA expression peaked at 90 min and was reduced to low levels thereafter, Smad6 mRNA remained high after 90 min of stimulation (FIG. 10A). Treatment of cells with 0.5% FCS, prior to ligand treatment, was found to decrease the basal level of inhibitory Smad expression, making the mRNA inductions observed with ligands more pronounced. The expression of Smad6 and Smad7 mRNA after stimulation with ligands were similar in cultures of high and low cell density.

As shown in the Examples above, Smad7 not only inhibits TGF-β and activin, but also BMP signaling. Smad7 associates with BMP type I receptors and inhibits BMPR-I-mediated signaling. Thus Smad7 may exert a negative feedback control on signaling by TGF-β1, activin as well as BMP-7.

Example 11

Smad6 is a Direct Target Gene for TGF-β1

Figure 10B:
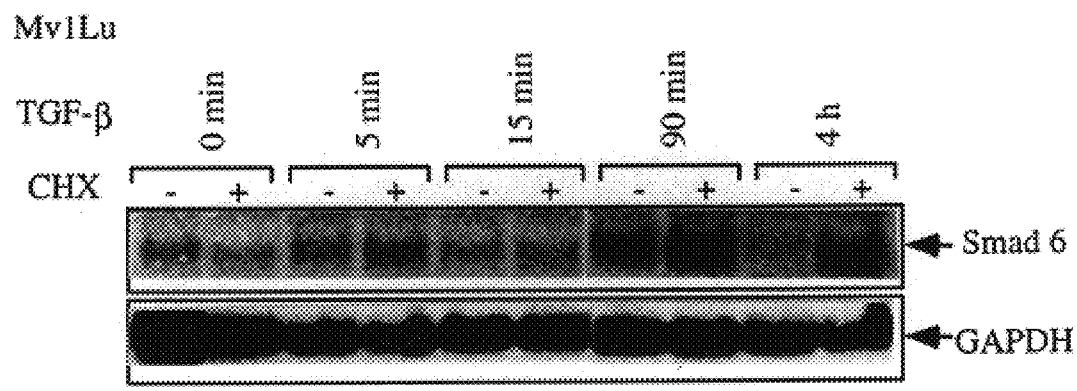
Figure 10C:
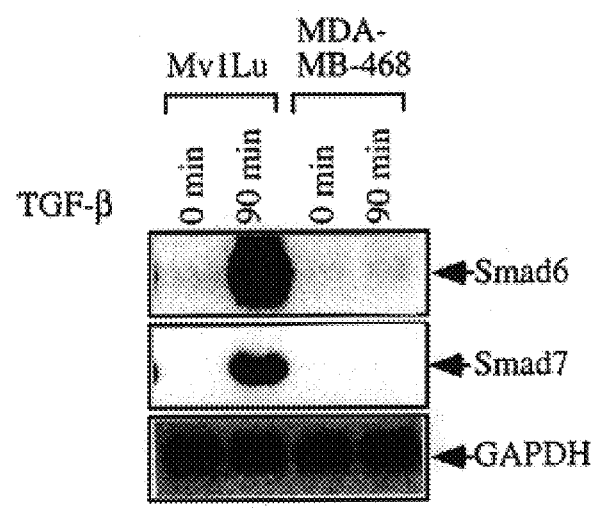

Previously it was demonstrated that the induction of Smad7 mRNA by TGF-β1 was observed in the presence of cycloheximide (CHX), indicating that de novo protein synthesis is not required for this response. Induction by TGF-β1 of Smad6 mRNA was also seen after addition of CHX (FIG. 10B). CHX (20 μg/ml) was added 30 min before TGF-β1. The induction of Smad6 mRNA was prolonged in the presence of both TGF-β1 and CHX when compared to TGF-β1 alone (FIG. 10B), probably as a result of CHX-induced loss of transcriptional repressors or increase in Smad6 mRNA stability. Based upon these results, Smad6 and Smad7 transcription are likely to be directly regulated by pathway-restricted and common mediator Smads. Therefore, the effect of TGF-β1 on MDA-MB-468 breast cancer cells that lack Smad4 (Lagna et al., *Nature*, 383:832–836, 1996) was examined (FIG. 10C). Smad6 mRNA expression was not affected by TGF-β1 in these cells. Smad7 expression was below detection level in the absence or presence of TGF-β1, or possibly the Smad7 gene may be absent in these cells. Taken together, the results indicate that Smad6 and Smad7 are immediate-early response genes for TGF-β family members.

Example 12
Transfection of Anti-sense Expression Construct Enhances Cellular Responsiveness to TGF-β1

Figure 11:
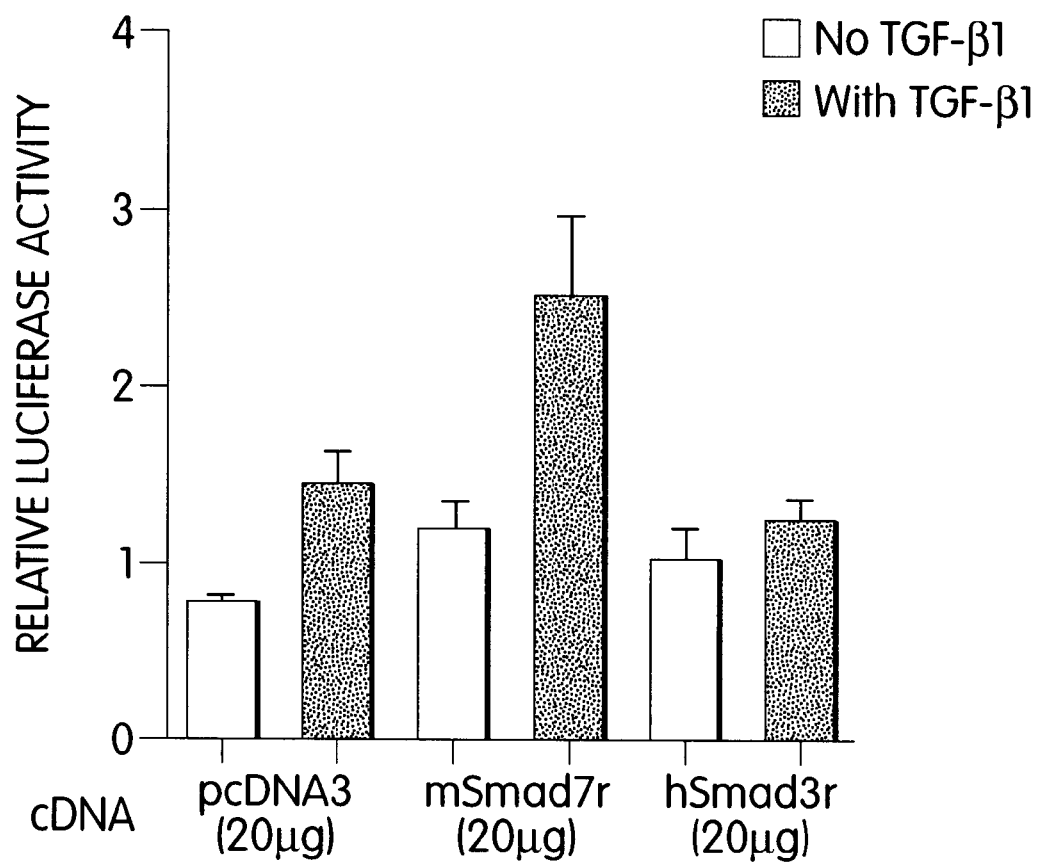
FIG. 11 shows that anti-sense Smad7 mRNA potentiates TGF-β1 transcriptional response.

To investigate whether the expression level of inhibitory Smads modulate the responsiveness to TGF-β, TGF-β1-induced transcriptional response was measured in Mv1Lu cells transfected with an anti-sense Smad7 cDNA expression construct. MV1Lu cells that are grown in the presence of serum have relatively high constitutive Smad7 expression (FIG. 9C), and Smad7 is rapidly induced by TGF-β1 (FIG. 10A). Transfection of anti-sense Smad7 expression construct (mSmad7r), but not empty vector or anti-sense Smad3 expression construct (hSmad3r), increased TGF-β1-mediated p3TPLux transcriptional response in Mv1Lu cells. TGF-β1 (10 ng/ml) was added 4 h prior to lysis of cells to measure luciferase activity. Data are presented as mean +/−SEM. Transfection of Mv1Lu cells with 20 μg of anti-sense Smad7 expression plasmid increased the TGF-β1 response, measured as activation of the PAI-1 promoter containing reporter, (p3TPlux) after a 4 h stimulation. The increased TGF-β response in the Smad7 anti-sense transfected cells was 2–4 fold compared to control cells transfected with empty expression vector (FIG. 11); the response was dependent on the amount of transfected anti-sense expression construct. Transfection with anti-sense Smad3 expression construct showed no or very weak inhibitory response (FIG. 11). These results indicate that the expression level of Smad7 determines the cellular responsiveness to TGF-β1.

Example 13
Effect of EGF and PMA on Smad6 and Smad7 mRNA Expression

Figure 12A:
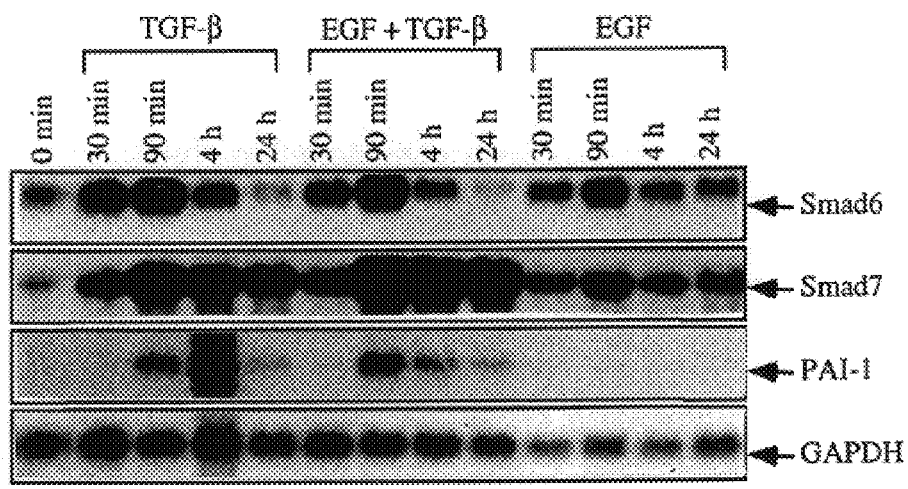
FIGS. 12A–12B depict the effect of EGF and PMA on Smad6 and Smad7 mRNA expression.
Figure 12B:
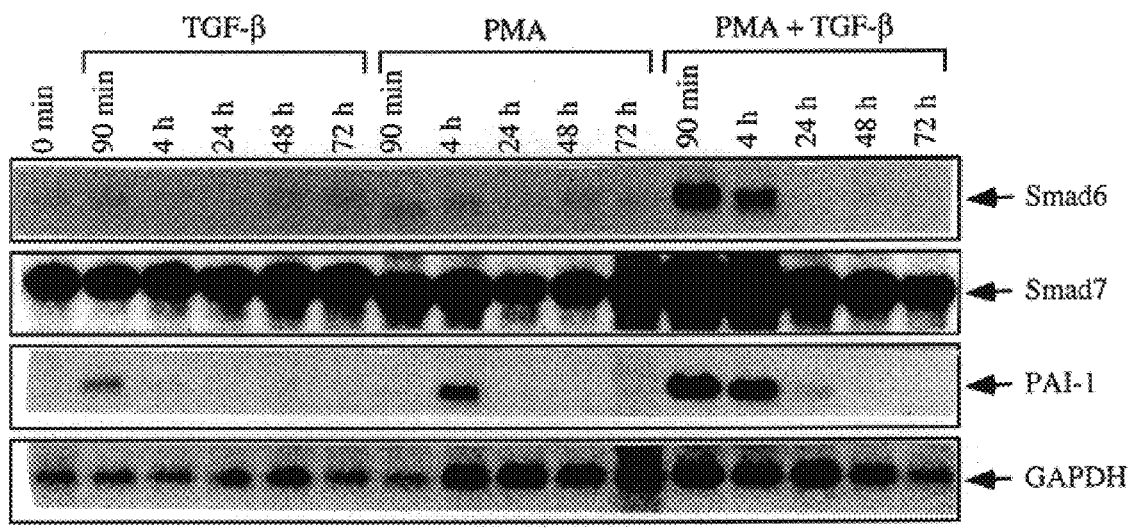

To examine the possibility of cross-talk between different signaling pathways, the effects of forskolin (activator of cAMP), epidermal growth factor (EGF) and phorbol ester PMA responses were determined in the absence and presence of 10 ng/ml TGF-β1. Forskolin had no effect alone, and only slightly enhanced the TGF-β1-induced expression of Smad6 and Smad7 mRNA. EGF (10 ng/ml) by itself was capable of inducing Smad6 and Smad7 expression, and acted synergistically with TGF-β1 for the induction of Smad7 mRNA (FIG. 12A). EGF was added 60 min. before TGF-β1. PMA ($10^{-8}$ M) alone had no appreciable effect, but a strong synergistic response was observed when PMA was added together with TGF-β1 on the induction of Smad6 and Smad7 expression (FIG. 12B). In this particular experiment the TGF-β1-mediated induction of Smad6 and Smad7 mRNA was very low, but could be observed upon longer exposure to X-ray film, thereby making synergistic effect more apparent. PAI-1 gene expression, which was found to be more rapidly induced by TGF-β1 (peak at 90 min) than PMA (peak at 4 h), was included as a control to show effect of PMA and TGF-β1 on cells.

Figure 13A:
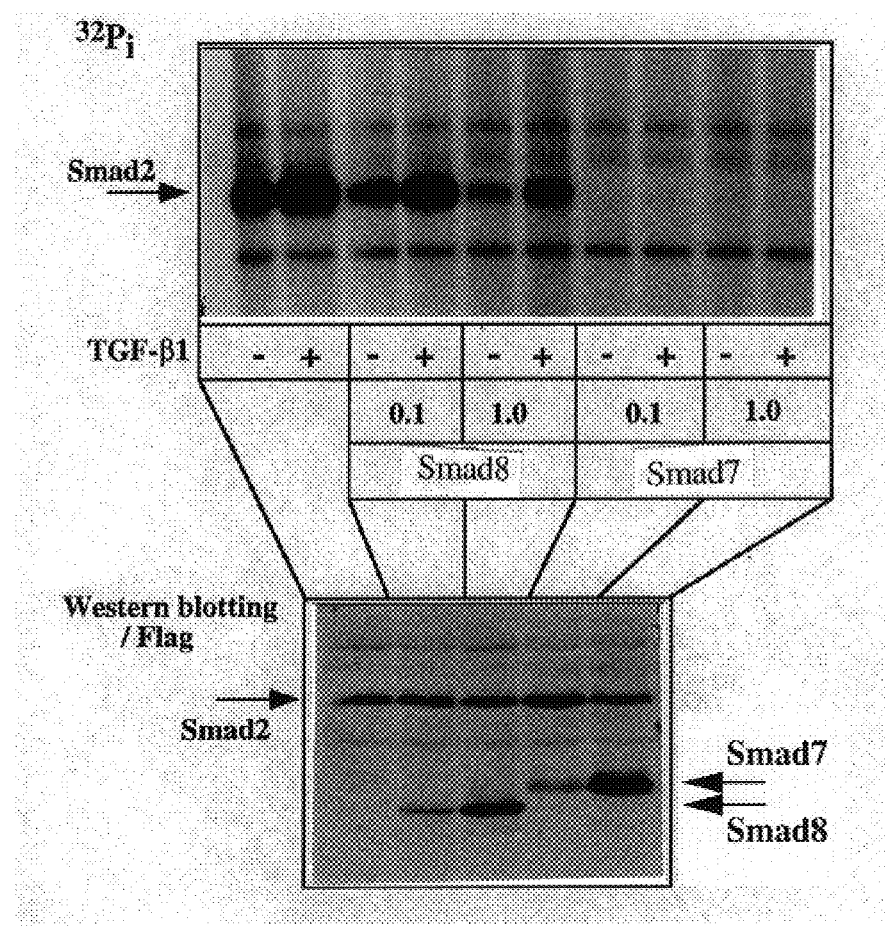
FIGS. 13A–13B show that Smad7 inhibits TGF-β-mediated signaling responses more effectively than Smad8.
Figure 13B:
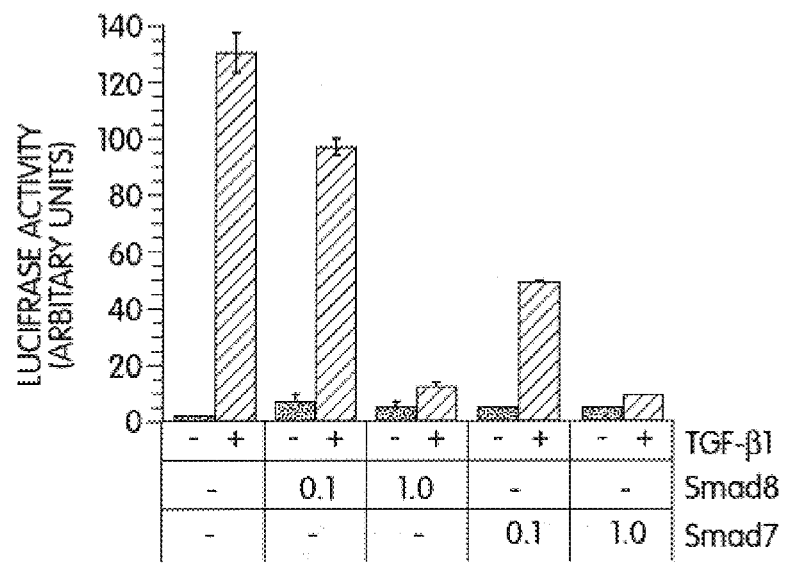

Example 14
Smad7 is More Potent than Smad8 In Inhibiting TGF-β-induced Responses Xenopus Smad8 shares 96% amino acid identity with murine Smad7 within the C-domain (Nakayama et al, 1998). Given that this domain is sufficient for receptor binding, and for inhibition of several TGF-β-induced responses, one would predict that these proteins would behave identically with regard to receptor binding and inhibition of downstream signaling. Consistent with this possibility, Smad8 interacted with the activated TβR-I, BMPR-IA, BMPR-IB and ActR-I. In addition, Smad9 inhibited BMPRI-mediated phosphorylation of Smad1 and Smad5 in a dose-dependent fashion that was indistinguishable from that of murine Smad7. FIG. 13A shows that Smad8 inhibits T βR-I-mediated phosphorylation of Smad2 less efficiently than Smad7. Cells were transfected with F-Smad2 alone or together with F-smad7 or F-Smad8 in the presence of T βR-I and T βR-II; cells were then incubated in the absence or presence of TGF-β. The level of F-Smad2 phosphorylation was determined by [$^{32}$P]orthophosphate labeling and immunoprecipitation of cell lysates with Flag antisera. Expression of F-Smads was analysed by Western blotting with Flag antiserum on aliquots of cell lysates. FIG. 13B shows that transfection of Smad7 in Mv1Lu cells blocks the TGF-β-induced p3TPLux response more effectively than Smad8. Thus, while Smad7 efficiently inhibited TβR-I-mediated phosphorylation of Smad2, Smad8 was less effective at doing so (FIG. 13A). Interestingly, this correlated with the more pronounced effect of Smad7 versus Smad8 in inhibiting TGF-β-induced transcriptional activation of the p3TPLux reporter gene (FIG. 13B). Of note, Smad7 is more effective than is Smad8 at inhibiting activin signaling in Xenopus mesoderm induction assay (Nakayama et al., 1998).

Example 15
Partial Secondary Axis Formation by Smad7 and Smad8

Figure 14A:
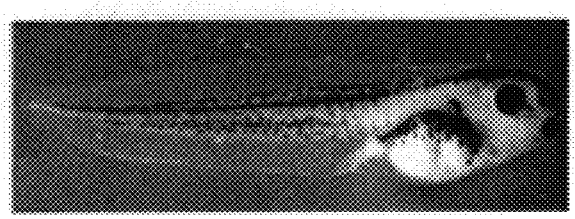
FIGS. 14A–14F show that overexpression of Smad7 in Xenopus embryos induces formation of a partial secondary axis and eye defects.
Figure 14B:
Figure 14C:
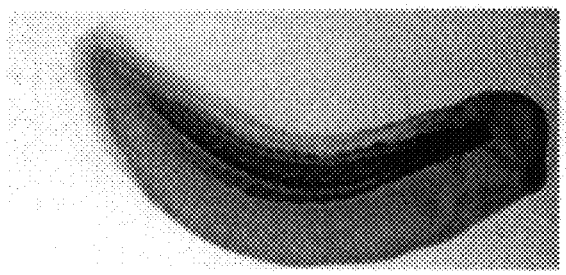
Figure 14D:
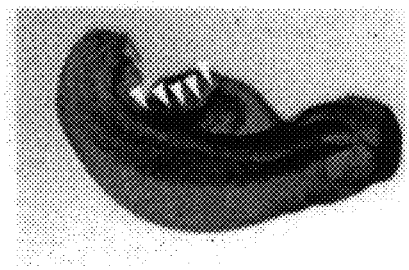
Figure 14E:
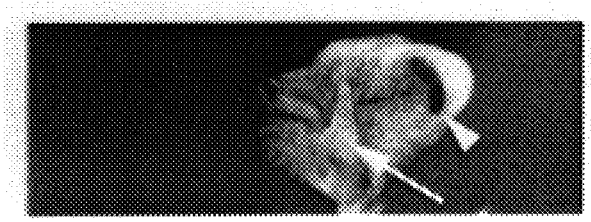

To determine whether Smad7 can inhibit transduction of BMP signals in vivo, patterning defects caused by overexpression of Smad7 in Xenopus embryos were analyzed. FIG. 14A shows photomicrographs of control tadpole and FIG. 14B shows sibling tadpole made to misexpress Smad7 in ventral cells. Note induction of partial secondary dorsal axis (arrow). FIG. 14C and FIG. 14D (control) depict Smad7-RNA injected sibling showing immunoreactive muscle in primary (arrow) and secondary (arrowhead) axes. FIG. 14E shows eye defects and spina bifida in an embryo made to overexpress Smad8 in dorsal cells. FIG. 14A shows fusion of eyes in an embryo made to overexpress Smad7 in dorsal cells. Overexpression of known BMP antagonists, such as dominant negative BMP receptors or ligands, on the ventral side of Xenopus embryos can induce the formation of a partial secondary axis (reviewed inGraff Cell 89:171–174, 1997). Injection of 200 or 400 pg of RNA encoding Smad7 near the ventral midline of four-cell embryos led to formation of a secondary dorsal axis in 90% (n=100) or 96% (n=79) of embryos, respectively (FIG. 14B). Secondary axis formation was observed in 94% (n=98) of embryos injected with 200 pg of RNA encoding that isolated C-domain of Smad7. Axes induced by either Smad7 or the C-domain of Smad7 contained immunoreactive muscle (FIG. 14D) but lacked notochord. In the same series of experiments, injection of 200 or 400 pg of RNA encoding Xenopus Smad8 near the ventral midline induced the formation of a secondary axis in 87 (n=92) or 91% (n=101) of injected embryos, respectively. One notable difference between the axes induced by the two gene products is that the secondary axes induced by Smad8 included a cyclopic or fused eye in 10% (200 pg) or 41% (400 pg) of cases whereas eye formation was rarely observed (3% of embryos) following misexpression of Smad7, and then only when a high dose (400 pg) of RNA was injected.

Example 16
Ectopic Expression of Smad7 in Dorsal Cells Induces a Subset of the Patterning Defects Caused by Overexpression of Smad8

Figure 14F:

Ectopic expression of Smad8 within dorsal cells of Xenopus embryos produces a range of phenotypic defects which cannot be attributed to blockade of BMP signaling. These include failure of the neural folds to fuse (spina bifida) as well as a range of eye defects (Nakayama et al., 1998). To directly compare patterning defects cause by misexpression of Smad7 and Smad8 within dorsal cells, 200 pg of RNA encoding either protein was injected near the dorsal midline of four-cell embryos. While 20% of Smad8-injected embryos developed spina bifida, and 40% showed a decrease in eye pigmentation (n=50), 97% of Smad7-injected embryos developed completely normally (n=89). When a higher dose (400 pg) of RNA encoding either Smad8 or Smad7 was injected, 40% of Smad8-injected embryos developed with spina bifida (FIG. 14E, n=124) while only 7% of embryos injected with Smad7 RNA (n=140), and 3% of embryos injected with a control RNA (encoding a myc epitope tag, n=70) displayed this defect. In contrast, 43% of Smad7-injected embryos developed with variable eye defects ranging from a slight to moderate decrease in eye pigment to fusion of the eyes (FIG. 14F). Forty-seven per cent of Smad8-injected siblings developed with comparable eye defects (Nakayama et al., 1998). The percentage of Smad8-injected embryos displaying spina bifida, eye induction or eye defects was somewhat lower in these experiments than that previously reported (Nakayama et al., 1998), possibly due to inherent differences between embryos used for the two sets of experiments. Together, these results suggest that Smad7 and Smad8 can interact with common signaling pathways in vivo although Smad8 may target additional, as of yet unidentified, pathways. Therefore, overexpression of Smad8 in Xenopus embryos produces patterning defects that are not observed following overexpression of Smad7, suggesting that Smad7 and Smad8 may preferentially target distinct signaling pathways. While it cannot be ruled out that the possibility that these differences are due to species specificity, e.g., the possibility that mammalian Smad7 is more efficiently translated, or interacts more efficiently with receptors in mammalian cells than does Xenopus Smad8, the results do not support this interpretation. Specifically, Smad7 is a more potent antagonist of TGF-β/activin signaling in both mammalian and Xenopus systems than is Smad8.

Example 17
Smad7 but not Smad6 inhibits TGF-β1-induced Growth Inhibition.

Figure 15:
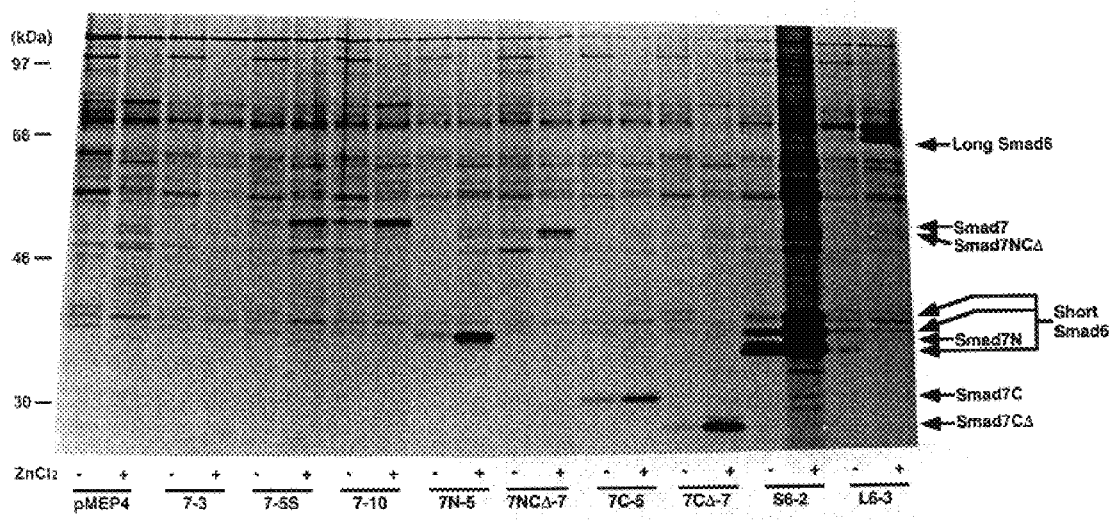
FIG. 15 shows characterization of expression of Smad7 and Smad6 in stable pMEP-4-driven transfected clones.
Figure 16A:
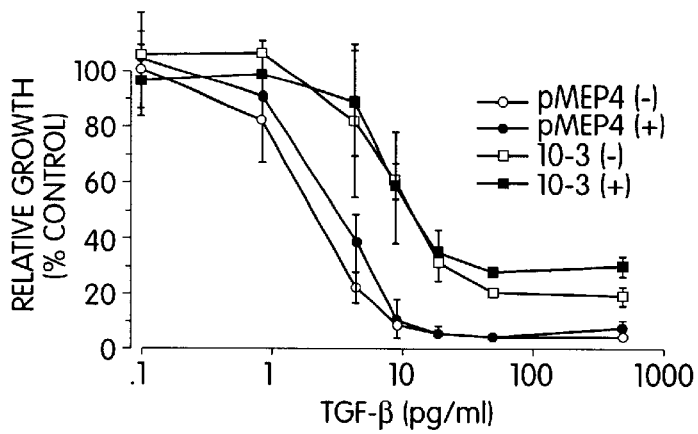
FIGS. 16A–16E show that Smad7 inhibits TGF-β1-mediated growth inhibition (A–C) Effective of Smad7 on TGF-β1-induced growth inhibition in three independent clones (D) Effective of Smad6S and (E) Smad6L on TGF-β1-induced growth inhibition.
Figure 16B:
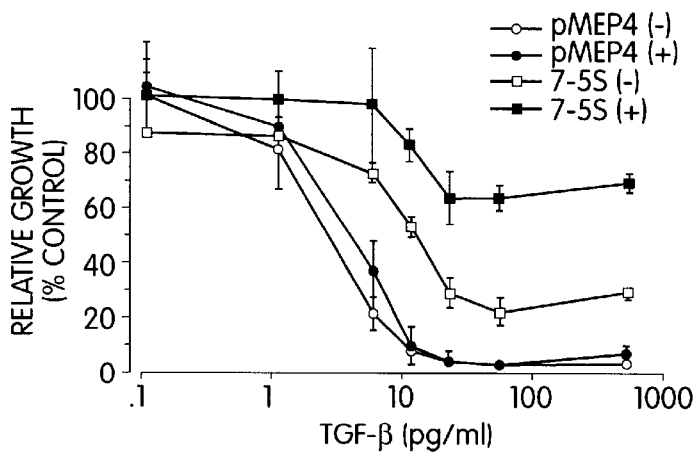
Figure 16C:
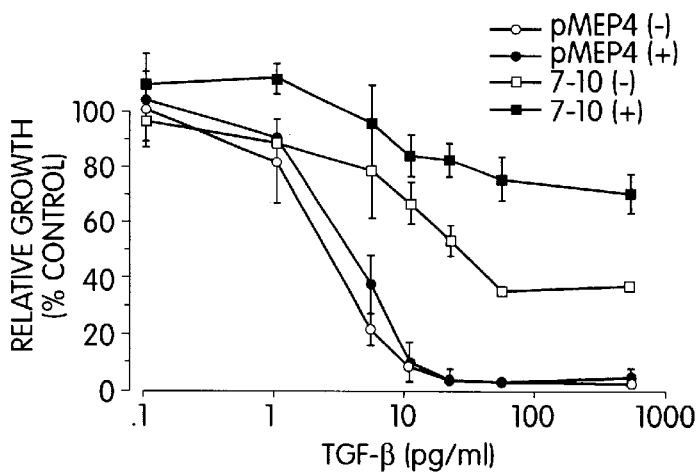
Figure 16D:
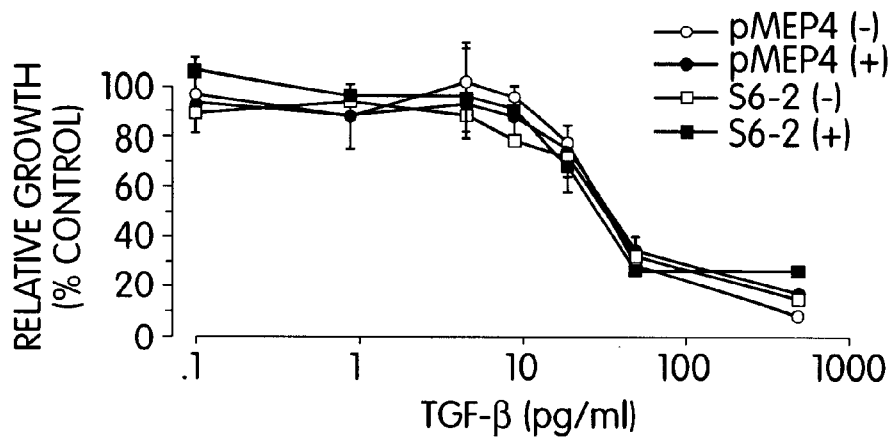
Figure 16E:
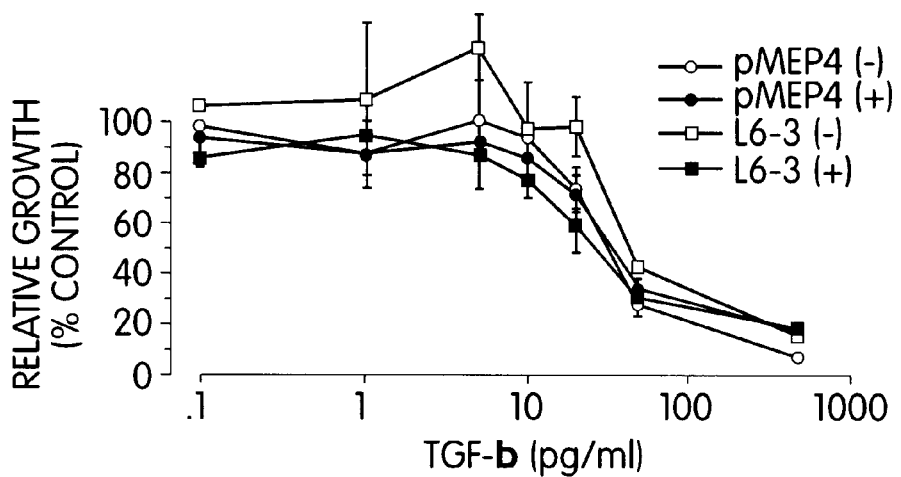

In order to investigate the effect of inhibitory Smads on TGF-β1-mediated growth inhibition, mouse Flag-tagged Smad6 (F-Smad6) and F-Smad7 were stably transfected into Mv1Lu cells; Smad6 and Smad7 were placed under transcriptional control of the human inducible metallothionien IIA promoter using the pMEP4 expression vector. Both reported forms of Smad6 were tested; a mouse long Smad6 version (Smad6L; Imamura et al., Nature 398:622–626, 1997) as well as a human short Smad6 version (Smad6S; Topper et al., PNAS 94:9314–9319, 1997). FIG. 15 shows characterization of Smad expression level in stable transfected Mv1Lu cell lines in the absence or presence of zinc chloride; wild-type F-Smad7 (pMEP4-smad7; three independent clones, 7-3, 7-5S and 7-10), the N-terminal domain of Smad7 (pMEP-7N, clone 7N-5), Smad7 with deletion at C-tail (pMEP4-7NCΔ, clone 7NCΔ-7), the C-terminal domain of Smad7 (pMEP4-7CΔ, clone 7CΔ-7) and the "short" variant of Smad6 (pMEP4-Smad6S, clone S6-2)and the "long" variant of Smad6 (pMEP4-Smad6L, clone L6-3) expression results are shown. Cells were metabolically labeled, and cell lysates subjected to immunoprecipitation with Flag antibody. Immunoprecipitates were analyzed by SDS-PAGE. When the expression of Smad6S, Smad6L and Smad7 was analyzed, we observed that the inhibitory Smads were already expressed in the absence of the inducer zinc chloride. This is result of leakage of the metallothionin promoter. Pretreatment of cells with zinc chloride in each transfectant led to increase in Smad6 and Smad7 expression (FIG. 15). Subsequently, we tested the response of the Smad7 and Smad7 (and empty pMEP4) transfectants for TGF-β1-induced growth inhibition in the absence or presence of zinc chloride. Multiple independent Smad7-expressing clones were analyzed. We found that Smad7 prevented the TGF-β1-induced growth-inhibitory effects in Mv1Lu (FIGS. 16A–C). In all Smad7 clones TGF-β1-induced growth inhibition was blocked to an extent which correlated with their different expression levels of Smad7. pMEP4-transfected Mv1Lu cells, in the absence or presence of zinc chloride showed a similar dose response curve for TGF-β1 as nontransfected Mv lLu cells. Ectopic expression Smad6L or Smad6S did not affect the TGF-β1-induced growth inhibition (FIGS. 16D,E). FIG. 16 shows the effect of TGF-β1 on pMEP4 transfected cells in the absence or presence of zinc chloride. The relative growth compared to control is plotted against the concentration of TGF-β1. Different lots of TGF-β1 were used in experiments A–C versus D,E, explaining why there is a difference between the ED50's on pMEP4 transfected cells in these experiments. All data shown are means +/−SED. Thus Smad7 can antagonize TGF-β1-induced growth inhibition, and appears to be more effective than Smad6.

Example 18
Smad7 Inhibits TGF-β1-induced Transcriptional Responses.

Figure 17:
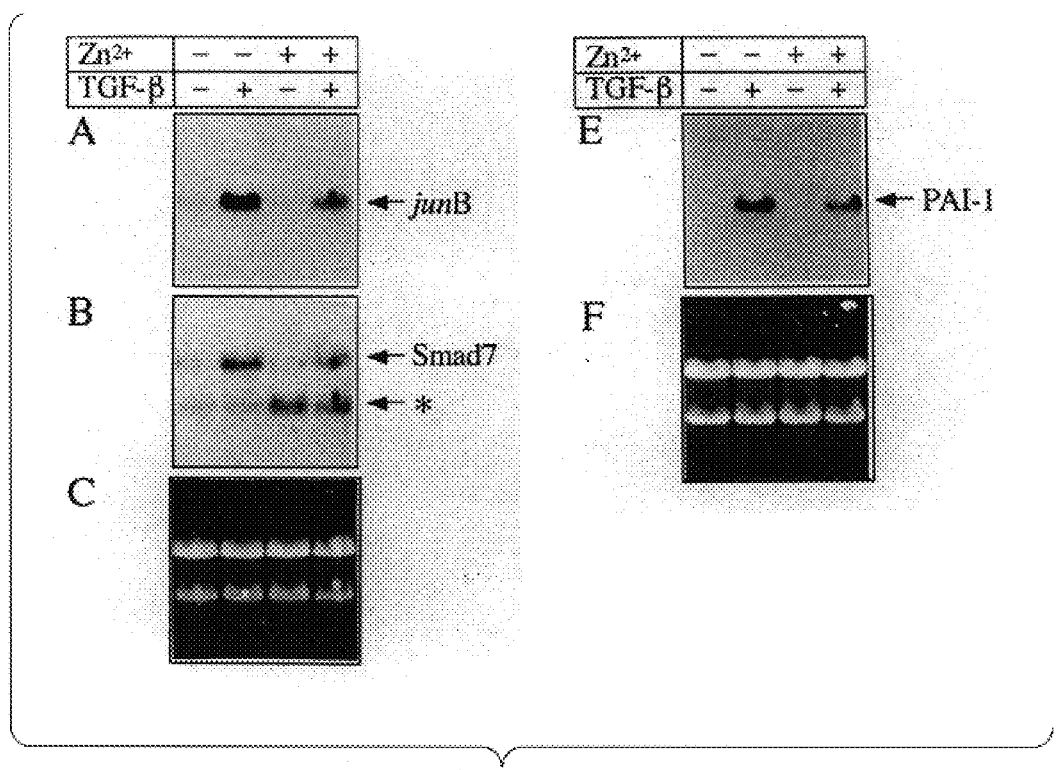
FIGS. 17A–17F show that Smad7 inhibits TGF-β1-mediated induction of early response genes.

Subsequently we examined the effect of ectopic Smad7 expression on TGF-β1-induced expression of the endogenous early response genes, Smad7, PAI-1 and JunB (FIG. 17). In FIG. 17 it is shown that ectopically expressed Smad7 inhibits TGF-β1-mediated induction of JUNB (A), Smad7 (B) and PAI-1 mRNA (E) expression. Northern blot analysis on RNA from Mv1Lu cells stably transfected with pMEP4-Smad7 without or with pretreatment with zinc chloride on exposure to TGF-β1. The endogenous mRNAs for junB, Smad7 and PAI-1 are indicated by arrows. The asterisk in Smad7 blot indicates the transfected F-Smad7 mRNA. The amount and intactness of total RNA loaded was checked by ethidium bromide staining (C and F). For junB (A) and Smad7 probe (B) the same blot was used, which was different from blot for PAI-11 probe (E). After treatment of cells with zinc chloride for 20 h prior to TGF-β1 stimulation for 2 h, the ectopically induced Smad7 was found to inhibit TGF-β1-induced immediate early gene responses at a Smad7 mRNA extopic expression level similar to that of endogenous gene after TGF-β treatment (FIG. 17B). Interestingly, upon treatment with zinc chloride for 6 h, no significant effect on TGF-β1 stimulation of early response genes in the Smad7 expressing clones was observed, whereas the apparent ectopic Smad7 mRNA levels were higher after 6 h versus 20 h pretreatment. Possibly differences in Smad7 mRNA do not correlate exactly with Smad7 protein levels upon zinc chloride treatment, or a particular post-translationally modification that occurs with slow kinetics may be required for interaction of Smad7 with receptor in MV1Lu cells.

Figure 18A:
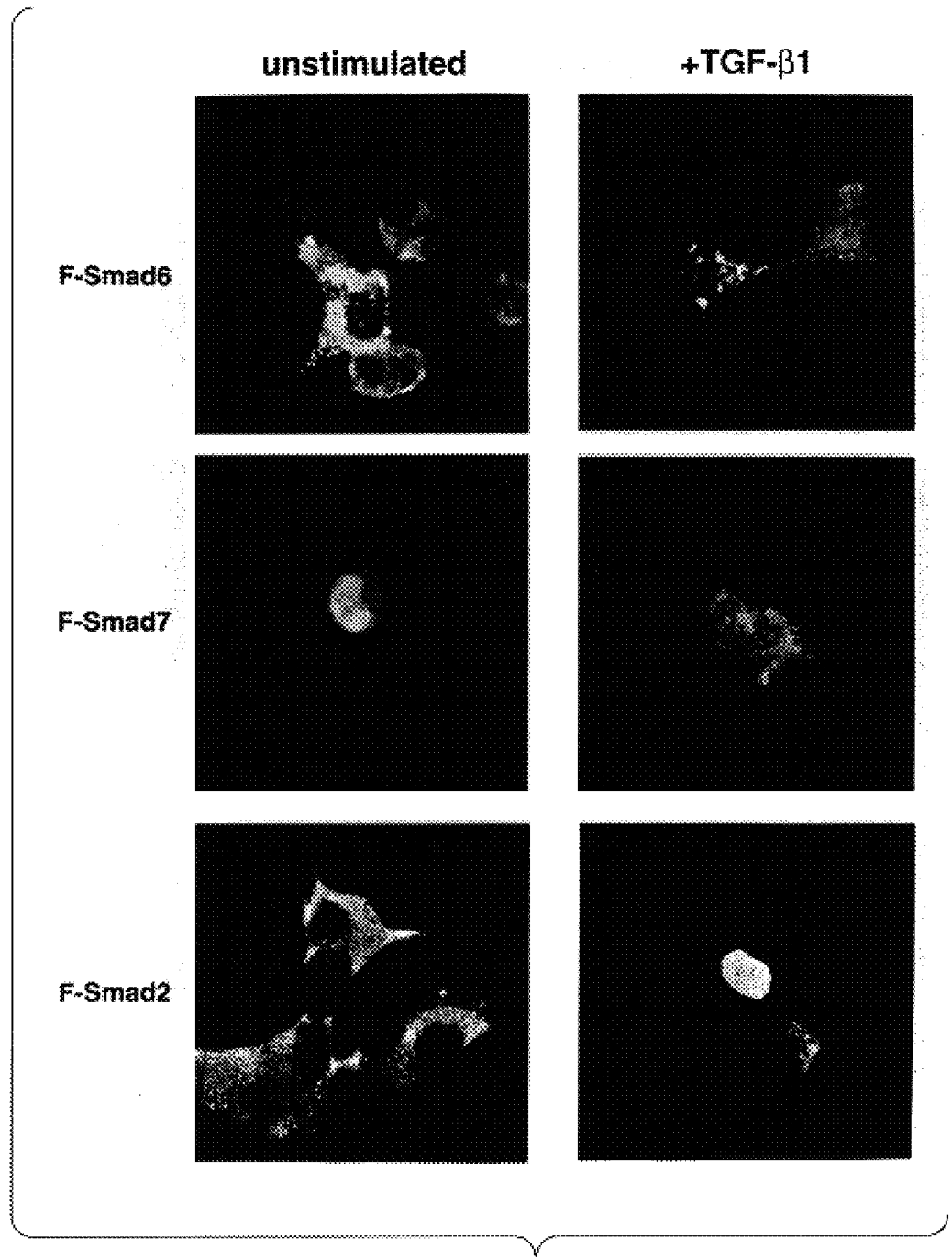
FIGS. 18A–18C show the subcellular distribution of Smad7 in the absence or presence of TGF-β1 receptor activation.
Figure 18B:
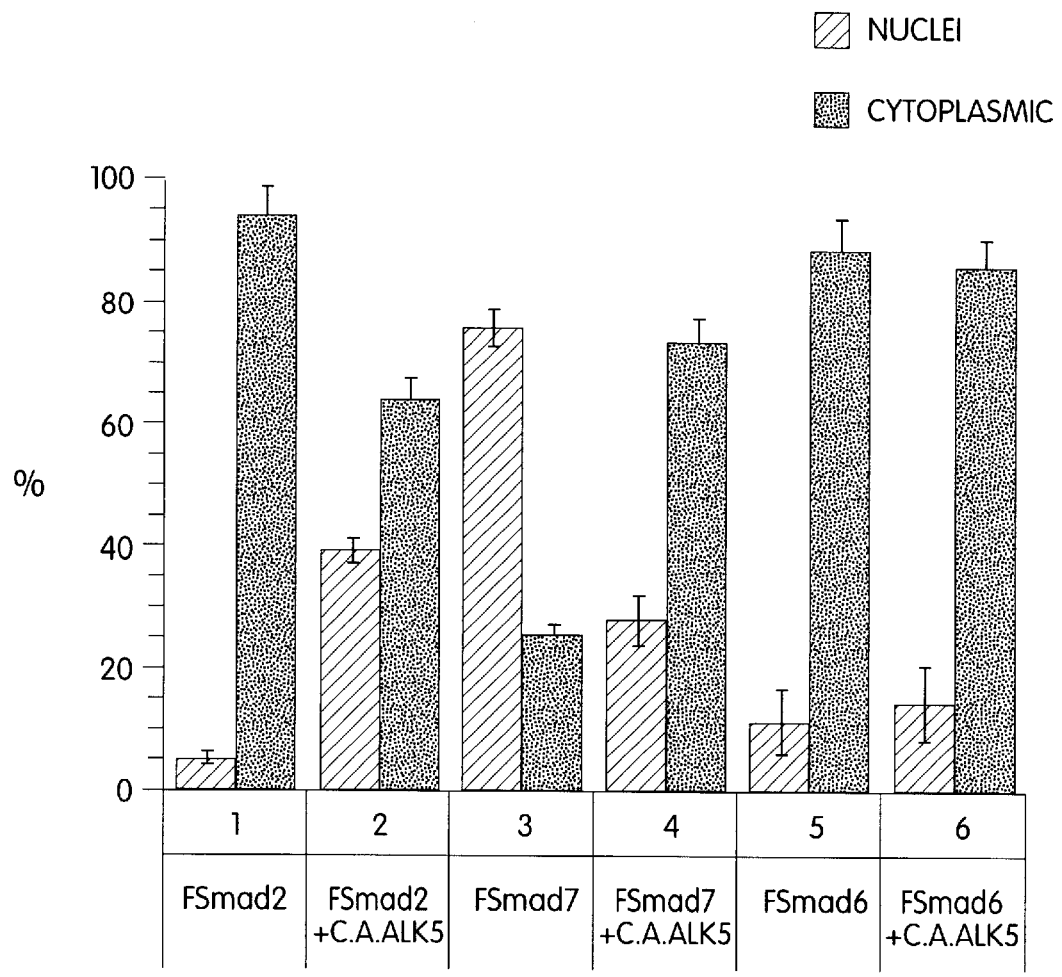
Figure 18C:
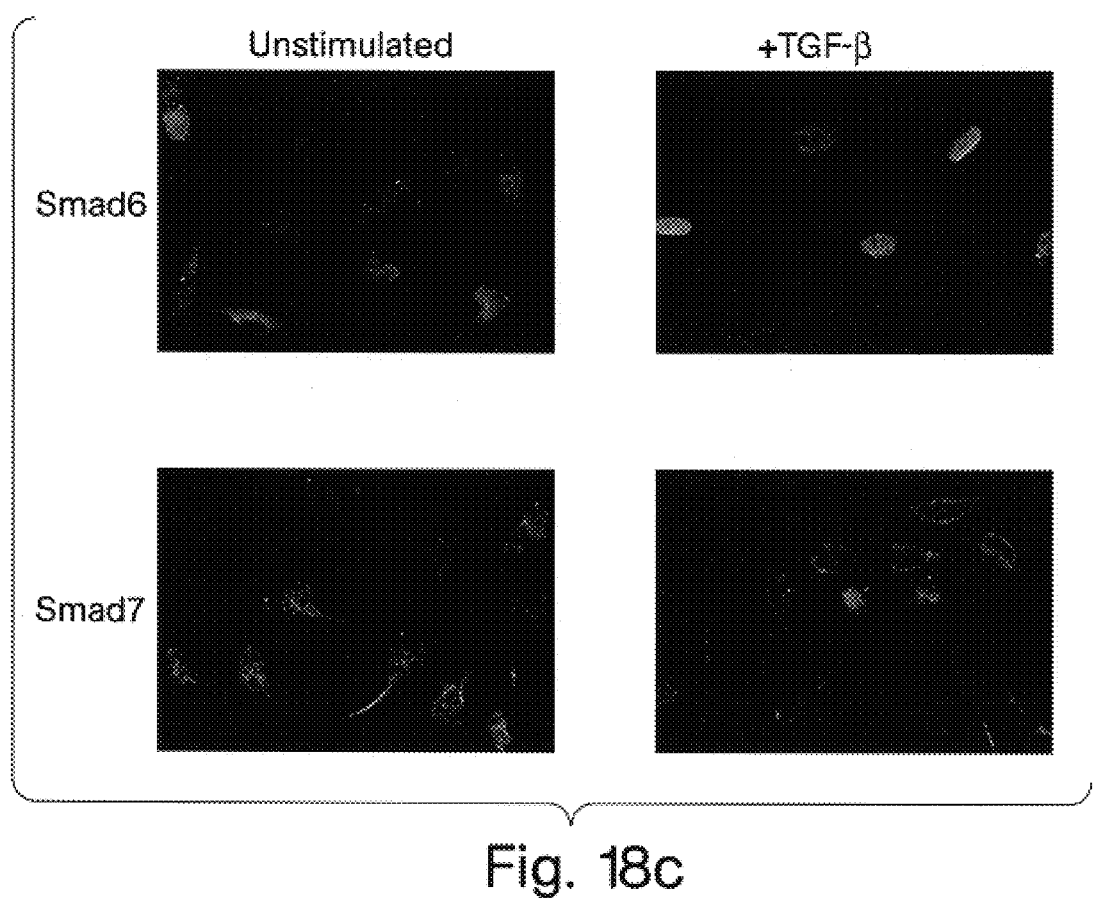
Figure 19A:
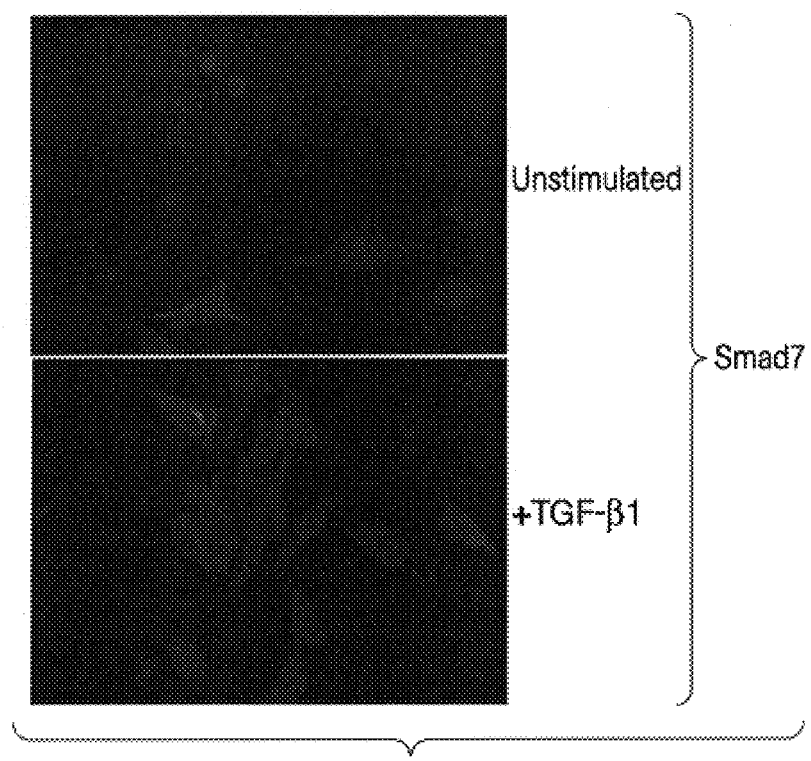
FIGS. 19A–19E show the subcellular distribution of wild-type Smad7 and Smad7 deletion mutants in the absence or presence of TGF-β1 stimulation.
Figure 19B:
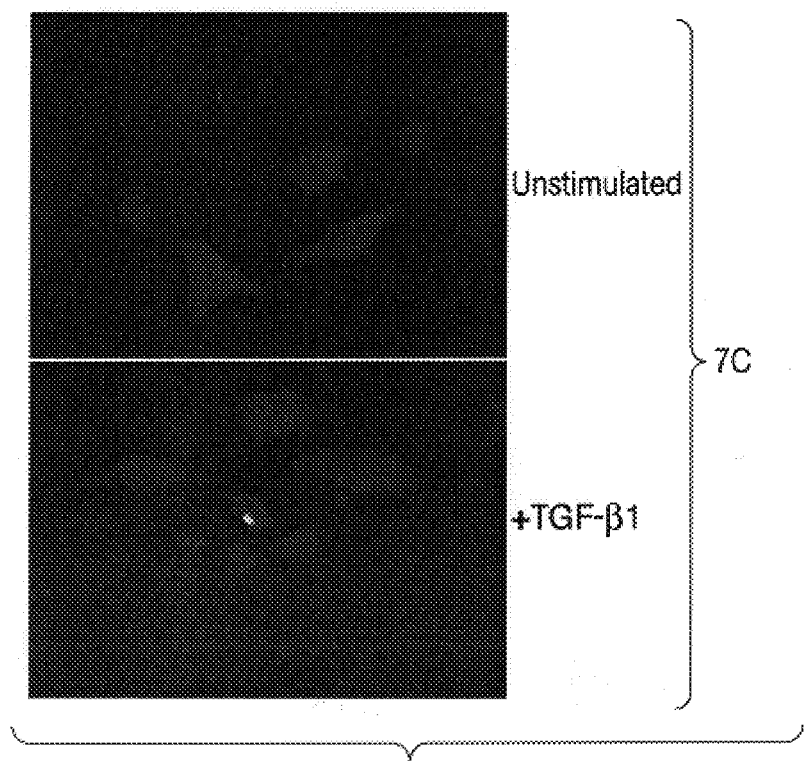
Figure 19C:
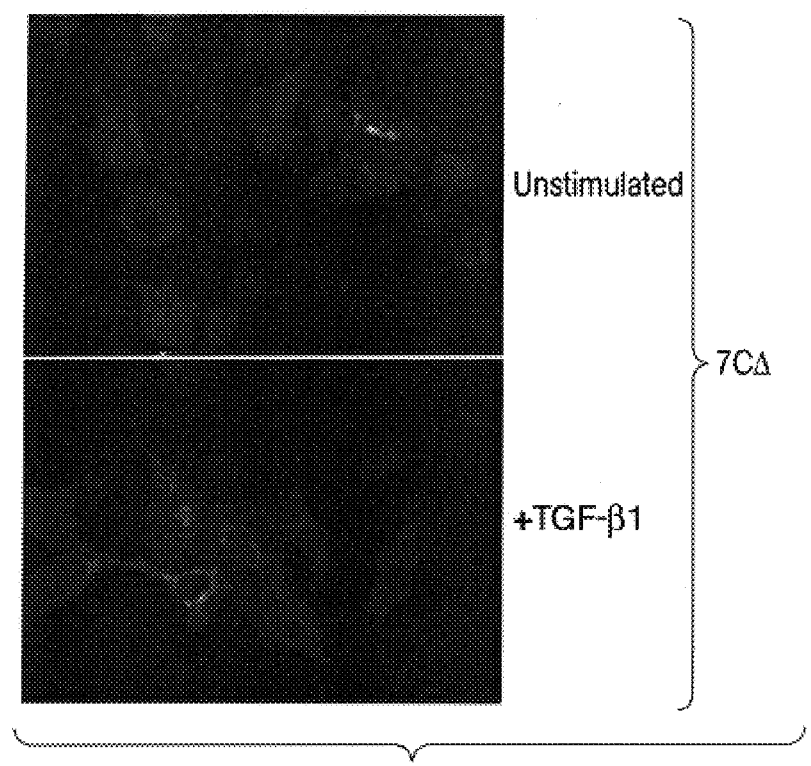
Figure 19D:
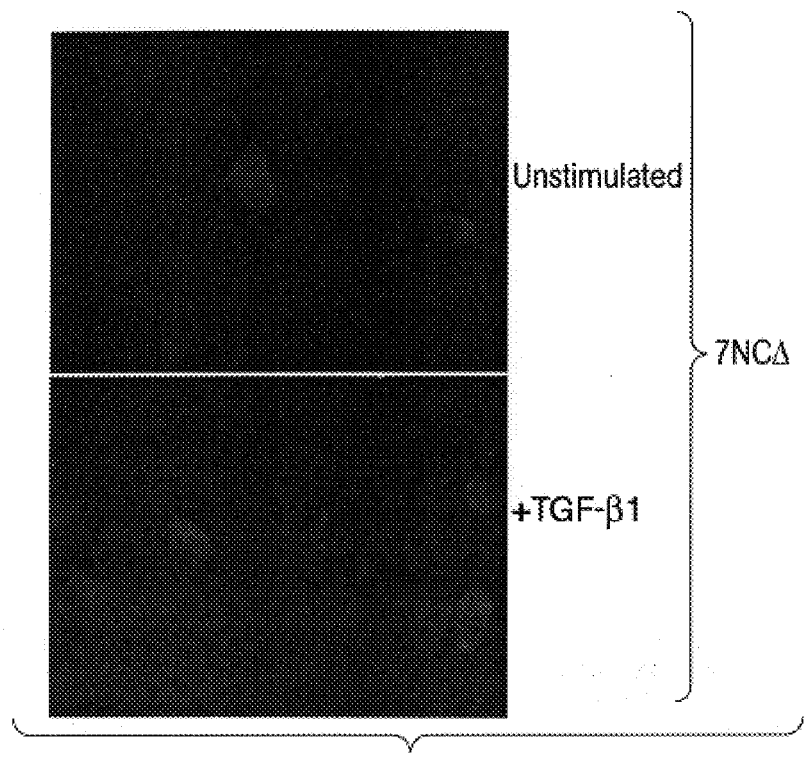
Figure 19E:
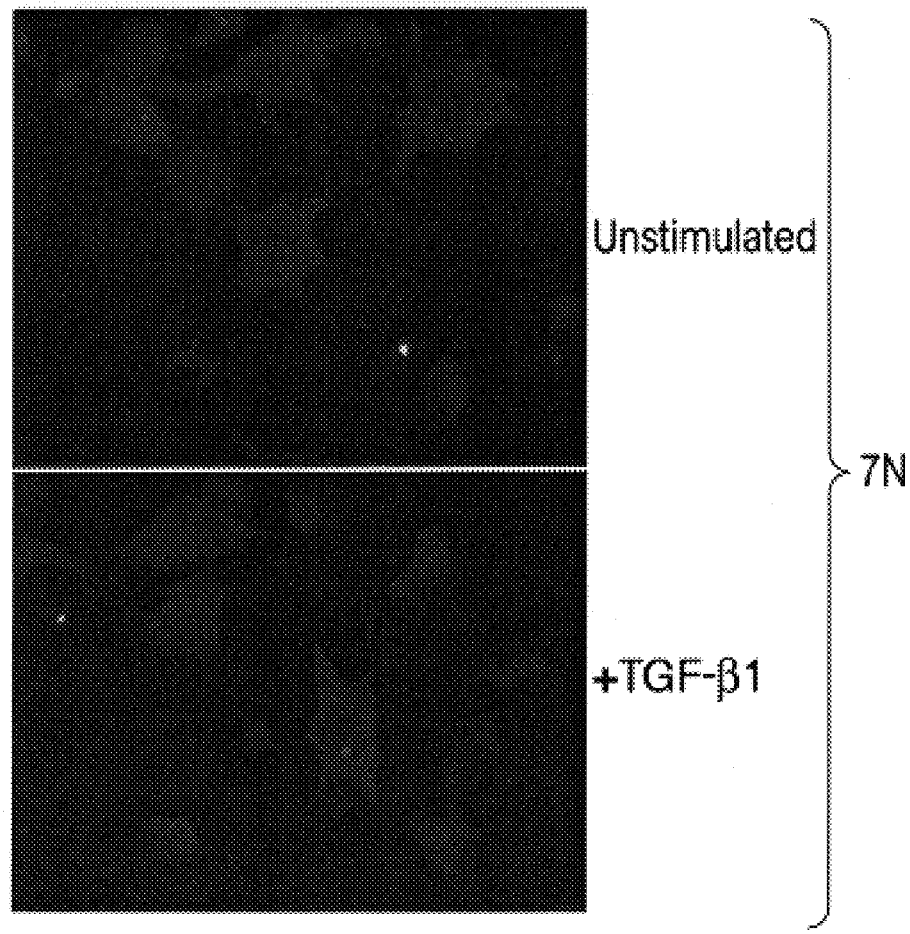
Figure 20:
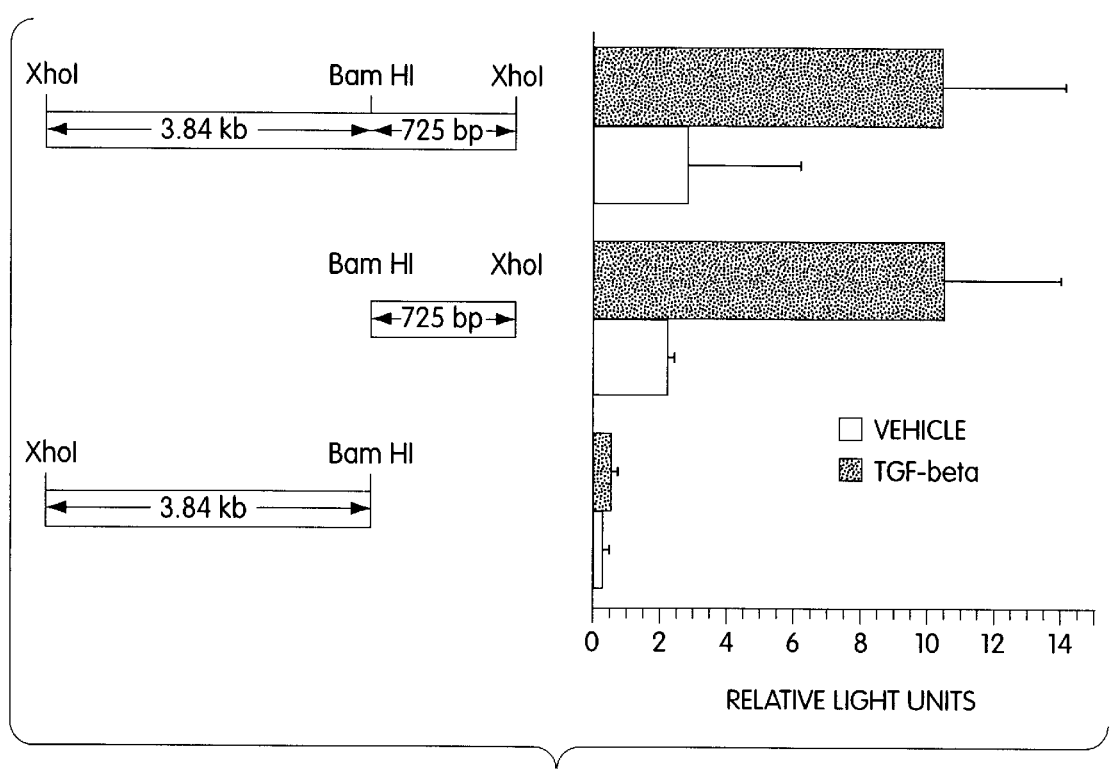
FIG. 20 depicts the results of a luciferase assays showing TGF-β1 inducibility of a Smad7 promoter fragment.

Example 19
TGF-β1-induced Nuclear Export of Smad7 in Transfected COS Cells and Nontransfected Mv1Lu Cells The subcellular localization of F-Smad6, F-Smad7 and F-Smad2 in transfected COS cells was analyzed in the absence or presence of the constitutive active TβR-I(T204D) by immunofluorescence using Flag antibody (FIG. 18A). In FIG. 18, Panel A shows the subcellular distribution of F-Smad7, F-Smad7 and F-Smad2 in the absence or presence of constitutive TβR-I(T204D) mutant in transfected COS cells. Smads were localized in the cells by immunofluorescence using Flag antibody. Panel B shows the quantitation of nuclear versus cytoplasmic cell staining for F-smads in the absence or presence of T βR-I(T204D). Panel C shows the subcellular distribution of Smad7 and Smad6 in nontransfected MV1Lu cells in the absence and presence of TGF-β1. The Smads were localized in the cells using specific antisera to Smad6 (ESP) or Smad7 (KER). Smad6 was mainly located in the cytoplasm of the cells and the subcellular localization was not different from Smad6 cotransfection with T βR-I(T204D), constitutively active TβR-1. Smad7 was located in the cell nuclei but exported in a large proportion of total treated cells from the nuclei to the cytoplasm upon cotransfection with T βR-I(T204D), which is in agreement with earlier reports (Eppert et al. 1996; Nakao et al., 1997). The quantitation of nuclear versus cytoplasmic staining for the different Smads in the absence or presence of TβR-I(T204D) are presented in FIG. 18B. The nuclear localization was checked by DAPI staining. The observed differences in subcellular distribution of Smad7 versus Smad2 and Smad6, suggest a functional significance of TβR-1-mediated export of Smad7 from the nucleus. However, over expression in COS cells and use of epitope tag may affect Smad7 subcellular distribution. Therefore, the subcellular distribution of inhibitory Smads in nontransfected Mv1Lu cells using antisera that specifically recognize Smad6 and Smad7 was also examined. In agreement with results in transfected COS cells, a cytoplasmic staining for Smad6 in the absence or presence of TGF-β (or BMP-7) was observed. In some experiments, a TGF-β1-induced nuclear translocation was observed in some of the cells (FIG. 18C). In the absence of ligand, a nuclear staining was observed for Smad7. However, upon TGF-β1 stimulation a cytoplasmic accumulation of Smad7 was induced (FIG. 18C). Two different antisera for each of Smad6 (recognizing Smad6L but not Smad6S) and Smad7, raised against different epitopes, gave identical results.

Example 20
Differential Localization of Smad7 Deletion Mutants in the Absence or Presence of TGF-β1

The subcellular localization of F-Smad6 and F-Smad7 in Mv1Lu cells stably expressing F-Smad7 and F-Smad7 were analyzed in the absence or presence TGF-β1 using the Flag antibody and immunofluorescence. In FIG. 19, the subcellular distribution of Smad7 mutants in the absence or presence of TGF-β1 is shown. The cells were pretreated with zinc chloride. Smads were localized in the cells using Flag antibody. Identical results were obtained, compared to the experiments in which transfected COS cells and nontransfected Mv1Lu cells were used; cytoplasmic staining for F-Smad6L and Smad6S versus a TGF-β1-induced nuclear export for F-Smad7 (FIG. 19). To gain more insight into regions in Smad7 that are important for nuclear localization and TGF-β1-induced nuclear export, the subcellular distribution of different Smad7 deletion mutants were analyzed. pMEP4 expression constructs for the C-terminal domain of F-Smad7 (7C; amino acids 204–426). F-Smad7C with C-tail deletion (7CΔ; amino acids 204–407) Smad7 with deletion of C-tail (7Δ; amino acids 1–407), and N-terminal domain of Smad7 (7N; amino acids 1–203) were stably transfected into Mv1Lu cells, and cell lines characterized for Smad7 expression upon zinc chloride treatment (FIG. 15). All cells showed some degree of leaky expression, but in all cell lines zinc treatment included expression of the Smad protein. Subcellular distribution of the 7C mutant (after zinc chloride treatment) in the absence or presence of TGF-β1 was similar to that of wild-type Smad7, although its efficiency of nuclear export was much less than that of wild-type Smad7. An intact MH2 domain appeared important for nuclear localization as 7CΔ and 7Δ mutants were predominantly in cytoplasm in the absence of TGF-β1. Smad7N was found in the cytoplasm in the absence or presence of TGF-β1; it had a spotted localization suggesting association with a particular cell structure (FIG. 19). None of the Smad7 deletion constructs were able to interfere with TGF-β1-induced growth inhibition as observed for Smad7 wild-type.

Example 21
Characterization of the Mouse Smad7 Promoter

The mouse Smad7 promoter was isolated from a commercially available genomic DNA library of the 129/Sv mouse strain (Stratagene, La Jolla, Calif.), using a ~800 bp Smad7 cDNA fragment as a probe (nucleotides 883–1614 of SEQ ID NO. 3).

Figure 21:
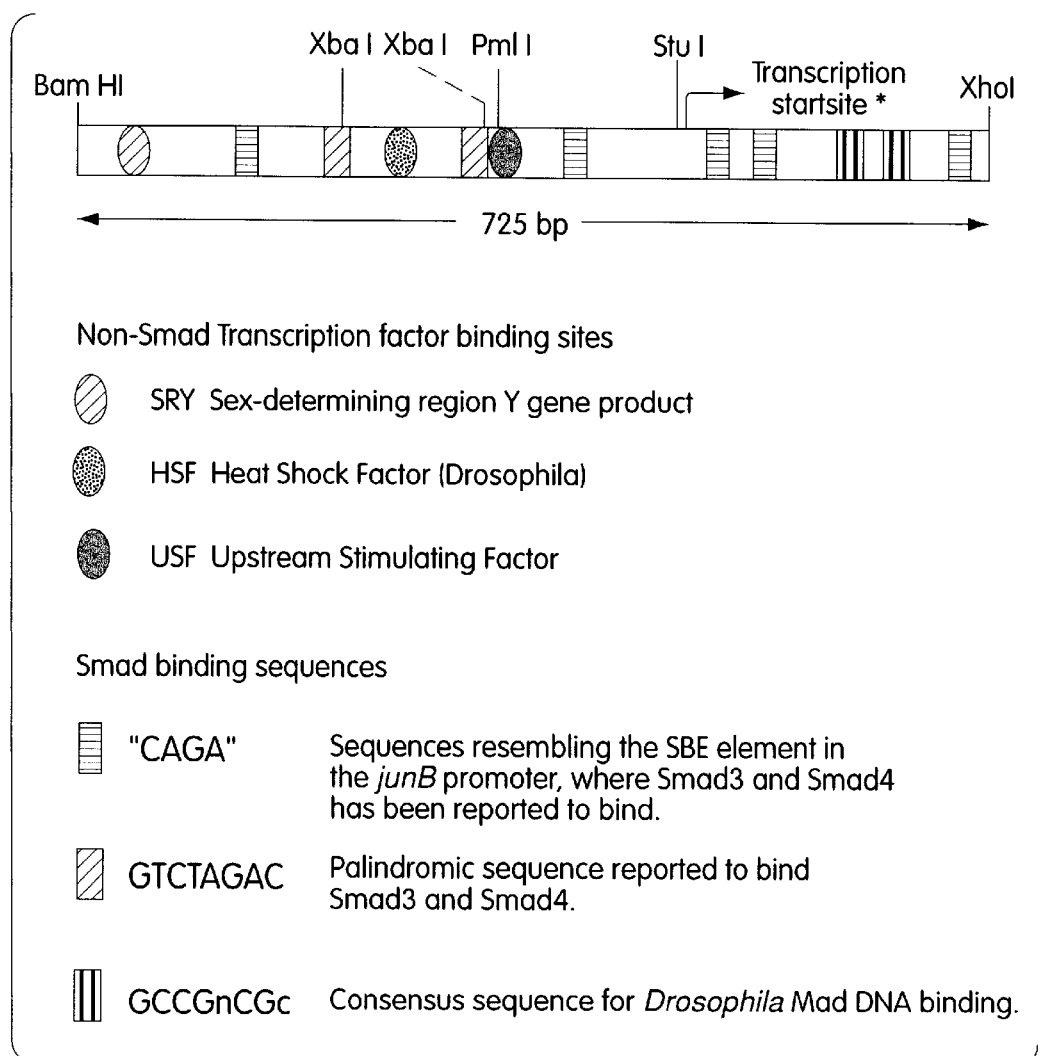
FIG. 21 depicts several restriction enzyme sites and putative binding sites for different anscription factors and Smad proteins in the ~725 bp Bam HI-Xho I minimal promoter fragment SEQ ID NO:15).

The putative Smad7 promoter that was isolated comprised of a ~4,465 bp Xho I-Xho I fragment from the 5'-end of the Smad7 mouse genomic DNA. A single Bam HI site was identified by restriction mapping ~3,840 bp from the 5'-Xho I site. In order to determine the promoter properties of the ~4,465 bp Xho I-Xho I DNA, three different regions of this DNA fragment (i.e., ~4,465 bp Xho I-Xho I, ~725 bp Bam HI-Xho I, and ~3,840 bp Xho I-Bam HI) were inserted 5' of the promoter-less luciferase reporter gene in the commercially available pGL3-Basic expression vector (Promega, Madison, Wis.) and transfected into HepG2 cells. Following transfection, the cells were starved overnight in DMEM (0.3% FBS) and later stimulated with 10 ng/ml of TGF-β1 or vehicle (negative control) for 16 hours. The cells were lysed and subjected to luciferase analysis. These results, depicted in FIG. 21, show that both the ~4,465 bp Xho I-Xho I and the ~725 bp Bam HI-Xho I Smad7 DNA fragments but not the ~3,840 bp Xho I-Bam HI fragment, confer TGF-β1 inducibility to the heterologous luciferase transcription unit.

The 725 bp Bam HI-Xho I Smad7 promoter fragment was further characterized. Its sequence is depicted as SEQ ID NO. 15 of the sequence listing. The transcriptional start site was localized by an RNAase Pretection Assay and was localized at ~nucleotide 499 of SEQ ID NO. 15. This start site was also found to coincide with the predicted start site as determined by computer software programs searching for such sites (Wingender, E. et al., Biotechnology, 1994, 35:273–280; Prestidge, D. et al., J Mol Biol, 1995, 249:923–932). FIG. 22 depicts several restriction enzyme sites and putative binding sites for different transcription factors and Smad proteins in the Bam HI-Xho I promoter fragment. The putative binding sites for non-Smad transcription factors were identified using the well known in the art TFSEARCH computer program and the TRANSFAC MATRIX TABLE database. Putative Smad binding regions were assessed using sequence information from the literature.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

A Sequence Listing is presented followed by what is claimed:

What is claimed is:

1. An isolated nucleic acid molecule selected from the group consisting of
  (a) nucleic acid molecules comprising a nucleic acid sequence selected from the group consisting of SEQ ID NO:3, SEQ ID NO:5, SEQ ID NO:7 and SEQ ID NO:8, and
  (b) full-length complements of (a).

2. The isolated nucleic acid molecule of claim 1, wherein the isolated nucleic acid molecule comprises SEQ ID NO:7 or SEQ ID NO:8.

3. The isolated nucleic acid molecule of claim 1, wherein the isolated nucleic acid molecule consists of SEQ ID NO:3.

4. The isolated nucleic acid molecule of claim 1, wherein the isolated nucleic acid molecule consists of SEQ ID NO:5.

5. An expression vector comprising the isolated nucleic acid molecule of claim 1 operably linked to a promoter.

6. A host cell transformed or transfected with the expression vector of claim 5.

7. The isolated nucleic acid molecule of claim 2, wherein the isolated nucleic acid molecule consists of SEQ ID NO:7.

8. The isolated nucleic acid molecule of claim 2, wherein the isolated nucleic acid molecule consists of SEQ ID NO:8.

9. A method for making a Smad7 polypeptide comprising culturing the host cell of claim 6 in a culture medium and isolating the polypeptide from the host cell or culture medium.

10. A method for making a Smad7 polypeptide comprising introducing the nucleic acid molecule of claim 1 into a non-cell system for transcription and/or translation of a nucleic acid molecule, incubating the non-cell system under conditions sufficient for transcription and/or translation of the nucleic acid molecule and isolating the polypeptide produced by the transcription and/or translation from the non-cell system.

11. A method for making a Smad7 polypeptide comprising introducing the expression vector of claim 5 into a non-cell system for transcription and/or translation of a nucleic acid molecule, incubating the non-cell system under conditions sufficient for transcription and/or translation of the nucleic acid molecule and isolating the polypeptide produced by the transcription and/or translation from the non-cell system.

12. An isolated nucleic acid molecule comprising a nucleotide sequence encoding an amino acid sequence selected from the group consisting of SEQ ID NO:4 and SEQ ID NO:6.

13. An isolated nucleic acid molecule consisting of a nucleotide sequence encoding an amino acid sequence selected from the group consisting of SEQ ID NO:4 and SEQ ID NO:6.

14. An expression vector comprising the isolated nucleic acid molecule of claim 12 operably linked to a promoter.

15. A host cell transformed or transfected with the expression vector of claim 14.

16. A method for making a Smad7 polypeptide comprising culturing the host cell of claim 15 in a culture medium and isolating the polypeptide from the host cell or culture medium.

17. A method for making a Smad7 polypeptide comprising introducing the nucleic acid molecule of claim 12 into a non-cell system for transcription and/or translation of a nucleic acid molecule, incubating the non-cell system under conditions sufficient for transcription and/or translation of the nucleic acid molecule and isolating the polypeptide produced by the transcription and/or translation from the non-cell system.

18. A method for making a Smad7 polypeptide comprising introducing the expression vector of claim 14 into a non-cell system for transcription and/or translation of a nucleic acid molecule, incubating the non-cell system under conditions sufficient for transcription and/or translation of the nucleic acid molecule and isolating the polypeptide produced by the transcription and/or translation from the non-cell system.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
       (A) LENGTH: 480 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:1:

```
CAGCAACCAT GGACGGGTTT CACCGTGCAG ATCAGCTTTG TGAAGGGCTG GGGCCAGTGC      60

TACACCCGCC AGTTCATCAG CAGCTGCCCG TGCTGGCTGG AGGTCATCTT CAACAGCCGG     120

TAGTCGGTCG TGTGGTGGGG AGAAGAGGAC AGGGCGGATC GTGAGCCGAG CAGGCCACCG     180

TTCAAACTAC TTGCTGCTAA CCTTTCCCGA GTGATTGCTT TTCATGCAAA CTCTTTGGTT     240

GGTGTTGTTA TTGCCATTCA TTGTTGGTTT TGTTTTGTTC TGTTCTGGGT TCAGCCTGGC     300

CTGCCCAGCC CTGGTCATCC AGCTGTACTG GCCCCTGGGG GGGTTCTGAG CAGTGCCTCT     360

TGTCTTGGAG ACAGACCTGG TGCCTGGCGC TGCCTTCAGC AGGCAGCAGG CAGCCTCCTG     420

CACACTGGCT TTTTTAGTCA TTTATGGGCA AAAAGAGTTA AAGTAAAACT TTGCAAATCC     480
```

(2) INFORMATION FOR SEQ ID NO:2:

(i) SEQUENCE CHARACTERISTICS:
       (A) LENGTH: 295 base pairs
       (B) TYPE: nucleic acid
       (C) STRANDEDNESS: single
       (D) TOPOLOGY: linear (xi) SEQUENCE DESCRIPTION: SEQ ID NO:2:

```
ACTCTAGTTC ACAGAGTCGA CTAAGGTGAT GGGGGTTGCA GCACACCAGC TCGGGGTTGA      60

TCTTCCCGTA AGATTCACAG CAACACAGCC TCTTGACTTC CGAGGAATGC CTGAGATCCG     120

GCCACCTGAA CACTTTGCAC AGCAGGAGGG GGAGCGAGTA GGACGAGGGC GGCTGCACTG     180

GCTGCCGCTG GCGGGCACGC CCGGGCCCAG CCTGCAGTCC AGGCGGCCGG GCAGCAGGAG     240

GCACGCGGTG CGCGTACCGC CGCGGGACTC CACGGCCTGA AGCAGCAGCT CCAGC         295
```

(2) INFORMATION FOR SEQ ID NO:3:

(i) SEQUENCE CHARACTERISTICS:
       (A) LENGTH: 1945 base pairs
       (B) TYPE: nucleic acid
       (C) STRANDEDNESS: single
       (D) TOPOLOGY: linear (ix) FEATURE:
       (A) NAME/KEY: Coding Sequence
       (B) LOCATION: 308...1585
       (D) OTHER INFORMATION:

(xi) SEQUENCE DESCRIPTION: SEQ ID NO:3:

```
CGTTCCTCCA GGGTCACGCC GGGGCCCGAA AGCCGCGCAG GGCGCGGGCC GCGCCGGGTG      60

GGGCATCCGA AGCGCAGCCC CCCGATCCCC GGCAGGCGCC CTGGGCCCCC GCGCGCGCCC     120

CGGCCTCTGG GAGATGGCGC ATGCCAGGAG GGCCCCTCCG GCCGCCGCCG GTTCTGCCCG     180
```

```
GGCCCCTGCT GTTGCTGCTG TCGCCTGCGC CTGNTGCCCC AAGTCGGCGC CCGATTNTTC    240

ATGGTGTGCG GAGGTCATGT TCGCTCCTTA GCCGGCAAAC GATTTTCTCC TCGCCTCCTC    300

GCCCCGC ATG TTC AGG ACC AAA CGA TCT GCG CTC GTC CGG CGT CTC TGG      349
        Met Phe Arg Thr Lys Arg Ser Ala Leu Val Arg Arg Leu Trp
        1               5                   10

AGG AGC CGT GCG CCC GGC GGC GAG GAC GAG GAG GAG GGC GTG GGG GGT      397
Arg Ser Arg Ala Pro Gly Gly Glu Asp Glu Glu Glu Gly Val Gly Gly
15              20                  25                  30

GGC GGC GGA GGA GGC GAG CTG CGG GGA GAA GGG GCG ACG GAC GGC CGG      445
Gly Gly Gly Gly Gly Glu Leu Arg Gly Glu Gly Ala Thr Asp Gly Arg
            35                  40                  45

GCT TAT GGG GCT GGT GGC GGC GGT GCG GGC AGG GCT GGC TGC TGC CTG      493
Ala Tyr Gly Ala Gly Gly Gly Gly Ala Gly Arg Ala Gly Cys Cys Leu
        50                  55                  60

GGC AAG GCA GTC CGA GGT GCC AAA GGT CAC CAC CAT CCC CAT CCC CCA      541
Gly Lys Ala Val Arg Gly Ala Lys Gly His His His Pro His Pro Pro
    65                  70                  75

ACC TCG GGT GCC GGG GCG GCC GGG GGC GCC GAG GCG GAT CTG AAG GCG      589
Thr Ser Gly Ala Gly Ala Ala Gly Gly Ala Glu Ala Asp Leu Lys Ala
80                  85                  90

CTC ACG CAC TCG GTG CTC AAG AAA CTC AAG GAG CGG CAG CTG GAG CTG      637
Leu Thr His Ser Val Leu Lys Lys Leu Lys Glu Arg Gln Leu Glu Leu
95                  100                 105                 110

CTG CTT CAG GCC GTG GAG TCC CGC GGC GGT ACG CGC ACC GCG TGC CTC      685
Leu Leu Gln Ala Val Glu Ser Arg Gly Gly Thr Arg Thr Ala Cys Leu
            115                 120                 125

CTG CTG CCC GGC CGC CTG GAC TGC AGG CTG GGC CCG GGG GCG CCC GCC      733
Leu Leu Pro Gly Arg Leu Asp Cys Arg Leu Gly Pro Gly Ala Pro Ala
        130                 135                 140

AGC GCG CAG CCC GCG CAG CCG CCC TCG TCC TAC TCG CTC CCC CTC CTG      781
Ser Ala Gln Pro Ala Gln Pro Pro Ser Ser Tyr Ser Leu Pro Leu Leu
    145                 150                 155

CTG TGC AAA GTG TTC AGG TGG CCG GAT CTC AGG CAT TCC TCG GAA GTC      829
Leu Cys Lys Val Phe Arg Trp Pro Asp Leu Arg His Ser Ser Glu Val
160                 165                 170

AAG AGG CTG TGT TGC TGT GAA TCT TAC GGG AAG ATC AAC CCC GAG CTG      877
Lys Arg Leu Cys Cys Cys Glu Ser Tyr Gly Lys Ile Asn Pro Glu Leu
175                 180                 185                 190

GTG TGC TGC AAC CCC CAT CAC CTT AGT CGA CTC TGT GAA CTA GAG TCT      925
Val Cys Cys Asn Pro His His Leu Ser Arg Leu Cys Glu Leu Glu Ser
            195                 200                 205

CCC CCT CCT CCT TAC TCC AGA TAC CCA ATG GAT TTT CTC AAA CCA ACT      973
Pro Pro Pro Pro Tyr Ser Arg Tyr Pro Met Asp Phe Leu Lys Pro Thr
        210                 215                 220

GCA GGC TGT CCA GAT GCT GTA CCT TCC TCC GCG GAA ACC GGG GGA ACG     1021
Ala Gly Cys Pro Asp Ala Val Pro Ser Ser Ala Glu Thr Gly Gly Thr
    225                 230                 235

AAT TAT CTG GCC CCT GGG GGG CTT TCA GAT TCC CAA CTT CTT CTG GAG     1069
Asn Tyr Leu Ala Pro Gly Gly Leu Ser Asp Ser Gln Leu Leu Leu Glu
240                 245                 250

CCT GGG GAT CGG TCA CAC TGG TGC GTG GTG GCA TAC TGG GAG GAG AAG     1117
Pro Gly Asp Arg Ser His Trp Cys Val Val Ala Tyr Trp Glu Glu Lys
255                 260                 265                 270

ACT CGC GTG GGG AGG CTC TAC TGT GTC CAA GAG CCC TCC CTG GAT ATC     1165
Thr Arg Val Gly Arg Leu Tyr Cys Val Gln Glu Pro Ser Leu Asp Ile
            275                 280                 285

TTC TAT GAT CTA CCT CAG GGG AAT GGC TTT TGC CTC GGA CAG CTC AAT     1213
Phe Tyr Asp Leu Pro Gln Gly Asn Gly Phe Cys Leu Gly Gln Leu Asn
        290                 295                 300
```

```
TCG GAC AAC AAG AGT CAG CTG GTA CAG AAA GTG CGG AGC AAG ATC GGC      1261
Ser Asp Asn Lys Ser Gln Leu Val Gln Lys Val Arg Ser Lys Ile Gly
            305                 310                 315

TGT GGC ATC CAG CTG ACG CGG GAA GTG GAT GGC GTG TGG GTT TAC AAC      1309
Cys Gly Ile Gln Leu Thr Arg Glu Val Asp Gly Val Trp Val Tyr Asn
320                 325                 330

CGC AGC AGT TAC CCC ATC TTC ATC AAG TCC GCC ACA CTG GAC AAC CCG      1357
Arg Ser Ser Tyr Pro Ile Phe Ile Lys Ser Ala Thr Leu Asp Asn Pro
335                 340                 345                 350

GAC TCC AGG ACG CTG TTG GTG CAC AAA GTG TTC CCT GGT TTC TCC ATC      1405
Asp Ser Arg Thr Leu Leu Val His Lys Val Phe Pro Gly Phe Ser Ile
                355                 360                 365

AAG GCT TTT GAC TAT GAG AAA GCC TAC AGC CTG CAG CGG CCC AAT GAC      1453
Lys Ala Phe Asp Tyr Glu Lys Ala Tyr Ser Leu Gln Arg Pro Asn Asp
            370                 375                 380

CAC GAG TTC ATG CAG CAA CCA TGG ACG GGT TTC ACC GTG CAG ATC AGC      1501
His Glu Phe Met Gln Gln Pro Trp Thr Gly Phe Thr Val Gln Ile Ser
385                 390                 395

TTT GTG AAG GGC TGG GGC CAG TGC TAC ACC CGC CAG TTC ATC AGC AGC      1549
Phe Val Lys Gly Trp Gly Gln Cys Tyr Thr Arg Gln Phe Ile Ser Ser
400                 405                 410

TGC CCG TGC TGG CTG GAG GTC ATC TTC AAC AGC CGG TAGTCGGTCG TGTGGT    1601
Cys Pro Cys Trp Leu Glu Val Ile Phe Asn Ser Arg
415                 420                 425

GGGGAGAAGA GGACAGGGCG GATCGTGAGC CGAGCAGGCC ACCGTTCAAA CTACTTGCTG    1661

CTAACCTTTC CCGAGTGATT GCTTTTCATG CAAACTCTTT GGTTGGTGTT GTTATTGCCA    1721

TTCATTGTTG GTTTTGTTTT GTTCTGTTCT GGGTTCAGCC TGGCCTGCCC AGCCCTGGTC    1781

ATCCAGCTGT ACTGGCCCCT GGGGGGGTTC TGAGCAGTGC CTCTTGTCTT GGAGACAGAC    1841

CTGGTGCCTG GCGCTGCCTT CAGCAGGCAG CAGGCAGCCT CCTGCACACT GGCTTTTTTA    1901

GTCATTTATG GGCAAAAAGA GTTAAAGTAA AACTTTGCAA ATCC                     1945

(2) INFORMATION FOR SEQ ID NO:4:

(i) SEQUENCE CHARACTERISTICS:
        (A) LENGTH: 426 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

Met Phe Arg Thr Lys Arg Ser Ala Leu Val Arg Arg Leu Trp Arg Ser
1               5                   10                  15

Arg Ala Pro Gly Gly Glu Asp Glu Glu Gly Val Gly Gly Gly
            20                  25                  30

Gly Gly Gly Glu Leu Arg Gly Glu Gly Ala Thr Asp Gly Arg Ala Tyr
        35                  40                  45

Gly Ala Gly Gly Gly Gly Gly Arg Ala Gly Cys Cys Leu Gly Lys
    50                  55                  60

Ala Val Arg Gly Ala Lys Gly His His His Pro His Pro Pro Thr Ser
65                  70                  75                  80

Gly Ala Gly Ala Ala Gly Gly Ala Glu Ala Asp Leu Lys Ala Leu Thr
                85                  90                  95

His Ser Val Leu Lys Lys Leu Lys Glu Arg Gln Leu Glu Leu Leu Leu
            100                 105                 110
```

```
Gln Ala Val Glu Ser Arg Gly Gly Thr Arg Thr Ala Cys Leu Leu Leu
        115                 120                 125
Pro Gly Arg Leu Asp Cys Arg Leu Gly Pro Gly Ala Pro Ala Ser Ala
130                 135                 140
Gln Pro Ala Gln Pro Pro Ser Ser Tyr Ser Leu Pro Leu Leu Leu Cys
145                 150                 155                 160
Lys Val Phe Arg Trp Pro Asp Leu Arg His Ser Ser Glu Val Lys Arg
                165                 170                 175
Leu Cys Cys Cys Glu Ser Tyr Gly Lys Ile Asn Pro Glu Leu Val Cys
            180                 185                 190
Cys Asn Pro His His Leu Ser Arg Leu Cys Glu Leu Glu Ser Pro Pro
        195                 200                 205
Pro Pro Tyr Ser Arg Tyr Pro Met Asp Phe Leu Lys Pro Thr Ala Gly
    210                 215                 220
Cys Pro Asp Ala Val Pro Ser Ser Ala Glu Thr Gly Gly Thr Asn Tyr
225                 230                 235                 240
Leu Ala Pro Gly Gly Leu Ser Asp Ser Gln Leu Leu Leu Glu Pro Gly
                245                 250                 255
Asp Arg Ser His Trp Cys Val Val Ala Tyr Trp Glu Glu Lys Thr Arg
            260                 265                 270
Val Gly Arg Leu Tyr Cys Val Gln Glu Pro Ser Leu Asp Ile Phe Tyr
        275                 280                 285
Asp Leu Pro Gln Gly Asn Gly Phe Cys Leu Gly Gln Leu Asn Ser Asp
    290                 295                 300
Asn Lys Ser Gln Leu Val Gln Lys Val Arg Ser Lys Ile Gly Cys Gly
305                 310                 315                 320
Ile Gln Leu Thr Arg Glu Val Asp Gly Val Trp Val Tyr Asn Arg Ser
                325                 330                 335
Ser Tyr Pro Ile Phe Ile Lys Ser Ala Thr Leu Asp Asn Pro Asp Ser
            340                 345                 350
Arg Thr Leu Leu Val His Lys Val Phe Pro Gly Phe Ser Ile Lys Ala
        355                 360                 365
Phe Asp Tyr Glu Lys Ala Tyr Ser Leu Gln Arg Pro Asn Asp His Glu
    370                 375                 380
Phe Met Gln Gln Pro Trp Thr Gly Phe Thr Val Gln Ile Ser Phe Val
385                 390                 395                 400
Lys Gly Trp Gly Gln Cys Tyr Thr Arg Gln Phe Ile Ser Ser Cys Pro
                405                 410                 415
Cys Trp Leu Glu Val Ile Phe Asn Ser Arg
            420                 425

(2) INFORMATION FOR SEQ ID NO:5:

(i) SEQUENCE CHARACTERISTICS:
        (A) LENGTH: 1876 base pairs
        (B) TYPE: nucleic acid
        (C) STRANDEDNESS: single
        (D) TOPOLOGY: linear (ix) FEATURE:
         (A) NAME/KEY: Coding Sequence
         (B) LOCATION: 50...1327
         (D) OTHER INFORMATION:

(xi) SEQUENCE DESCRIPTION: SEQ ID NO:5:

GAATTCGGCA CGAGGGCAAA CGACTTTTCT CCTCGCCTCC TCGCCCCGC ATG TTC AGG    58
                                                      Met Phe Arg
                                                       1
```

```
ACC AAA CGA TCT GCG CTC GTC CGG CGT CTC TGG AGG AGC CGT GCG CCC      106
Thr Lys Arg Ser Ala Leu Val Arg Arg Leu Trp Arg Ser Arg Ala Pro
    5                  10                  15

GGC GGC GAG GAC GAG GAG GAG GGC GCA GGG GGA GGT GGA GGA GGA GGC      154
Gly Gly Glu Asp Glu Glu Glu Gly Ala Gly Gly Gly Gly Gly Gly Gly
 20                  25                  30                  35

GAG CTG CGG GGA GAA GGG GCG ACG GAC AGC CGA GCG CAT GGG GCC GGT      202
Glu Leu Arg Gly Glu Gly Ala Thr Asp Ser Arg Ala His Gly Ala Gly
                 40                  45                  50

GGC GGC GGC CCG GGC AGG GCT GGA TGC TGC CTG GGC AAG GCG GTG CGA      250
Gly Gly Gly Pro Gly Arg Ala Gly Cys Cys Leu Gly Lys Ala Val Arg
             55                  60                  65

GGT GCC AAA TGT CAC CAC CAT CCC CAC CCG CCA GCC GCG GGC GCC GGC      298
Gly Ala Lys Cys His His His Pro His Pro Pro Ala Ala Gly Ala Gly
         70                  75                  80

GCG GCC GGG GGC GCC GAG GCG GAT CTG AAG GCG CTC ACG CAC TCG GTG      346
Ala Ala Gly Gly Ala Glu Ala Asp Leu Lys Ala Leu Thr His Ser Val
     85                  90                  95

CTC AAG AAA CTG AAG GAG CGG CAG CTG GAG CTG CTG CTC CAG GCC GTG      394
Leu Lys Lys Leu Lys Glu Arg Gln Leu Glu Leu Leu Leu Gln Ala Val
100                 105                 110                 115

GAG TCC CGC GGC GGG ACG CGC ACC GCG TGC CTC CTG CTG CCC GGC CGC      442
Glu Ser Arg Gly Gly Thr Arg Thr Ala Cys Leu Leu Leu Pro Gly Arg
                120                 125                 130

CTG GAC TGC AGG CTG GGC CCG GGG GCG CCC GCC GGC GCG CAG CCT GCG      490
Leu Asp Cys Arg Leu Gly Pro Gly Ala Pro Ala Gly Ala Gln Pro Ala
            135                 140                 145

CAG CCG CCC TCG TCC TAC TCG CTC CCC CTC CTG CTG TGC AAA GTG TTC      538
Gln Pro Pro Ser Ser Tyr Ser Leu Pro Leu Leu Leu Cys Lys Val Phe
        150                 155                 160

AGG TGG CCG GAT CTC AGG CAT TCC TCG GAA GTC AAG AGG CTG TGT TGC      586
Arg Trp Pro Asp Leu Arg His Ser Ser Glu Val Lys Arg Leu Cys Cys
165                 170                 175

TGT GAA TCT TAC GGG AAG ATC AAC CCC GAG CTG GTG TGC TGC AAC CCC      634
Cys Glu Ser Tyr Gly Lys Ile Asn Pro Glu Leu Val Cys Cys Asn Pro
180                 185                 190                 195

CAT CAC CTT AGC CGA CTC TGC GAA CTA GAG TCT CCC CCC CCT CCT TAC      682
His His Leu Ser Arg Leu Cys Glu Leu Glu Ser Pro Pro Pro Pro Tyr
                200                 205                 210

TCC AGA TAC CCG ATG GAT TTT CTC AAA CCA ACT GCA GAC TGT CCA GAT      730
Ser Arg Tyr Pro Met Asp Phe Leu Lys Pro Thr Ala Asp Cys Pro Asp
            215                 220                 225

GCT GTG CCT TCC TCC GCT GAA ACA GGG GGA ACG AAT TAT CTG GCC CCT      778
Ala Val Pro Ser Ser Ala Glu Thr Gly Gly Thr Asn Tyr Leu Ala Pro
        230                 235                 240

GGG GGG CTT TCA GAT TCC CAA CTT CTT CTG GAG CCT GGG GAT CGG TCA      826
Gly Gly Leu Ser Asp Ser Gln Leu Leu Leu Glu Pro Gly Asp Arg Ser
245                 250                 255

CAC TGG TGC GTG GTG GCA TAC TGG GAG GAG AAG ACG AGA GTG GGG AGG      874
His Trp Cys Val Val Ala Tyr Trp Glu Glu Lys Thr Arg Val Gly Arg
260                 265                 270                 275

CTC TAC TGT GTC CAG GAG CCC TCT CTG GAT ATC TTC TAT GAT CTA CCT      922
Leu Tyr Cys Val Gln Glu Pro Ser Leu Asp Ile Phe Tyr Asp Leu Pro
                280                 285                 290

CAG GGG AAT GGC TTT TGC CTC GGA CAG CTC AAT TCG GAC AAC AAG AGT      970
Gln Gly Asn Gly Phe Cys Leu Gly Gln Leu Asn Ser Asp Asn Lys Ser
            295                 300                 305

CAG CTG GTG CAG AAG GTG CGG AGC AAA ATC GGC TGC GGC ATC CAG CTG     1018
Gln Leu Val Gln Lys Val Arg Ser Lys Ile Gly Cys Gly Ile Gln Leu
        310                 315                 320
```

-continued

| | |
|---|---|
| ACG CGG GAG GTG GAT GGT GTG TGG GTG TAC AAC CGC AGC AGT TAC CCC<br>Thr Arg Glu Val Asp Gly Val Trp Val Tyr Asn Arg Ser Ser Tyr Pro<br>    325                                        330                          335 | 1066 |
| ATC TTC ATC AAG TCC GCC ACA CTG GAC AAC CCG GAC TCC AGG ACG CTG<br>Ile Phe Ile Lys Ser Ala Thr Leu Asp Asn Pro Asp Ser Arg Thr Leu<br>340                                345                              350                            355 | 1114 |
| TTG GTA CAC AAG GTG TTC CCC GGT TTC TCC ATC AAG GCT TTC GAC TAC<br>Leu Val His Lys Val Phe Pro Gly Phe Ser Ile Lys Ala Phe Asp Tyr<br>                        360                              365                              370 | 1162 |
| GAG AAG GCG TAC AGC CTG CAG CGG CCC AAT GAC CAC GAG TTT ATG CAG<br>Glu Lys Ala Tyr Ser Leu Gln Arg Pro Asn Asp His Glu Phe Met Gln<br>                                375                              380                            385 | 1210 |
| CAG CCG TGG ACG GGC TTT ACC GTG CAG ATC AGC TTT GTG AAG GGC TGG<br>Gln Pro Trp Thr Gly Phe Thr Val Gln Ile Ser Phe Val Lys Gly Trp<br>            390                                    395                              400 | 1258 |
| GGC CAG TGC TAC ACC CGC CAG TTC ATC AGC AGC TGC CCG TGC TGG CTA<br>Gly Gln Cys Tyr Thr Arg Gln Phe Ile Ser Ser Cys Pro Cys Trp Leu<br>                405                              410                            415 | 1306 |
| GAG GTC ATC TTC AAC AGC CGG TAGCCGCGTG CGGAGGGGAC AGAGCGTGAG CTGA<br>Glu Val Ile Phe Asn Ser Arg<br>420                              425 | 1361 |
| GCAGGCCACA CTTCAAACTA CTTTGCTGCT AATATTTTCC TCCTGAGTGC TTGCTTTTCA | 1421 |
| TGCAAACTCT TTGGTCGTTT TTTTTTTGTT TGTTGGTTGG TTTTCTTCTT CTCGTCCTCG | 1481 |
| TTTGTGTTCT ATTTTTCTAA CTACAAAGGT TTAAATGAAC AAGAGAAGCA TCTCTCATTG | 1541 |
| GAAATTTAGC ATTGTAGTGC TTTGAGAGAG AAAGGACTCC CTGNAAAAAA ACCTGAGATT | 1601 |
| TATTAAAGNA AAAAATGTAT TTTATGTTAT ATATAAATAT ATTATTACTT GTAAATATAA | 1661 |
| AGACGTTTTA TAAGCATCAT TATTTATGTA TTGTGCAATG TGTATAAACN AGNAAAATAA | 1721 |
| AGAAAAGATG CACTTTGCTT TAATATAAAT GCAAATAACA AATGCCAAAT TAAAAAAGAT | 1781 |
| AAACACAAGA TTGGTGTTTT TTTCTATGGG TGTTATCACC TAGCNGAATG TTTTTCTAAA | 1841 |
| GGAGTTTATG TTCCATTAAA CGATTTTTAA AANGT | 1876 |

(2) INFORMATION FOR SEQ ID NO:6:

(i) SEQUENCE CHARACTERISTICS:
        (A) LENGTH: 426 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:6:

Met Phe Arg Thr Lys Arg Ser Ala Leu Val Arg Arg Leu Trp Arg Ser
1               5                    10                 15

Arg Ala Pro Gly Gly Glu Asp Glu Glu Gly Ala Gly Gly Gly
              20                    25                    30

Gly Gly Gly Glu Leu Arg Gly Glu Gly Ala Thr Asp Ser Arg Ala His
        35                    40                    45

Gly Ala Gly Gly Gly Pro Gly Arg Ala Gly Cys Cys Leu Gly Lys
50                          55                    60

Ala Val Arg Gly Ala Lys Cys His His His Pro Pro Ala Ala
65                    70                    75                    80

Gly Ala Gly Ala Ala Gly Gly Ala Glu Ala Asp Leu Lys Ala Leu Thr
              85                    90                    95

```
His Ser Val Leu Lys Lys Leu Lys Glu Arg Gln Leu Glu Leu Leu Leu
                100                 105                 110

Gln Ala Val Glu Ser Arg Gly Gly Thr Arg Thr Ala Cys Leu Leu Leu
            115                 120                 125

Pro Gly Arg Leu Asp Cys Arg Leu Gly Pro Gly Ala Pro Ala Gly Ala
        130                 135                 140

Gln Pro Ala Gln Pro Pro Ser Ser Tyr Ser Leu Pro Leu Leu Leu Cys
145                 150                 155                 160

Lys Val Phe Arg Trp Pro Asp Leu Arg His Ser Ser Glu Val Lys Arg
                165                 170                 175

Leu Cys Cys Cys Glu Ser Tyr Gly Lys Ile Asn Pro Glu Leu Val Cys
            180                 185                 190

Cys Asn Pro His His Leu Ser Arg Leu Cys Glu Leu Glu Ser Pro Pro
        195                 200                 205

Pro Pro Tyr Ser Arg Tyr Pro Met Asp Phe Leu Lys Pro Thr Ala Asp
    210                 215                 220

Cys Pro Asp Ala Val Pro Ser Ser Ala Glu Thr Gly Gly Thr Asn Tyr
225                 230                 235                 240

Leu Ala Pro Gly Gly Leu Ser Asp Ser Gln Leu Leu Leu Glu Pro Gly
                245                 250                 255

Asp Arg Ser His Trp Cys Val Val Ala Tyr Trp Glu Glu Lys Thr Arg
            260                 265                 270

Val Gly Arg Leu Tyr Cys Val Gln Glu Pro Ser Leu Asp Ile Phe Tyr
        275                 280                 285

Asp Leu Pro Gln Gly Asn Gly Phe Cys Leu Gly Gln Leu Asn Ser Asp
290                 295                 300

Asn Lys Ser Gln Leu Val Gln Lys Val Arg Ser Lys Ile Gly Cys Gly
305                 310                 315                 320

Ile Gln Leu Thr Arg Glu Val Asp Gly Val Trp Val Tyr Asn Arg Ser
                325                 330                 335

Ser Tyr Pro Ile Phe Ile Lys Ser Ala Thr Leu Asp Asn Pro Asp Ser
            340                 345                 350

Arg Thr Leu Leu Val His Lys Val Phe Pro Gly Phe Ser Ile Lys Ala
        355                 360                 365

Phe Asp Tyr Glu Lys Ala Tyr Ser Leu Gln Arg Pro Asn Asp His Glu
    370                 375                 380

Phe Met Gln Gln Pro Trp Thr Gly Phe Thr Val Gln Ile Ser Phe Val
385                 390                 395                 400

Lys Gly Trp Gly Gln Cys Tyr Thr Arg Gln Phe Ile Ser Ser Cys Pro
                405                 410                 415

Cys Trp Leu Glu Val Ile Phe Asn Ser Arg
            420                 425

(2) INFORMATION FOR SEQ ID NO:7:

(i) SEQUENCE CHARACTERISTICS:
        (A) LENGTH: 1281 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ATGTTCAGGA CCAAACGATC TGCGCTCGTC CGGCGTCTCT GGAGGAGCCG TGCGCCCGGC      60

GGCGAGGACG AGGAGGAGGG CGTGGGGGGT GGCGGCGGAG GAGGCGAGCT GCGGGGAGAA     120
```

```
GGGGCGACGG ACGGCCGGGC TTATGGGGCT GGTGGCGGCG GTGCGGGCAG GGCTGGCTGC    180

TGCCTGGGCA AGGCAGTCCG AGGTGCCAAA GGTCACCACC ATCCCCATCC CCCAACCTCG    240

GGTGCCGGGG CGGCCGGGGG CGCCGAGGCG GATCTGAAGG CGCTCACGCA CTCGGTGCTC    300

AAGAAACTCA AGGAGCGGCA GCTGGAGCTG CTGCTTCAGG CCGTGGAGTC CCGCGGCGGT    360

ACGCGCACCG CGTGCCTCCT GCTGCCCGGC CGCCTGGACT GCAGGCTGGG CCCGGGGGCG    420

CCCGCCAGCG CGCAGCCCGC GCAGCCGCCC TCGTCCTACT CGCTCCCCCT CCTGCTGTGC    480

AAAGTGTTCA GGTGGCCGGA TCTCAGGCAT TCCTCGGAAG TCAAGAGGCT GTGTTGCTGT    540

GAATCTTACG GGAAGATCAA CCCCGAGCTG GTGTGCTGCA ACCCCCATCA CCTTAGTCGA    600

CTCTGTGAAC TAGAGTCTCC CCCTCCTCCT TACTCCAGAT ACCCAATGGA TTTTCTCAAA    660

CCAACTGCAG GCTGTCCAGA TGCTGTACCT TCCTCCGCGG AAACCGGGGG AACGAATTAT    720

CTGGCCCCTG GGGGCTTTC AGATTCCCAA CTTCTTCTGG AGCCTGGGGA TCGGTCACAC    780

TGGTGCGTGG TGGCATACTG GGAGGAGAAG ACTCGCGTGG GGAGGCTCTA CTGTGTCCAA    840

GAGCCCTCCC TGGATATCTT CTATGATCTA CCTCAGGGGA ATGGCTTTTG CCTCGGACAG    900

CTCAATTCGG ACAACAAGAG TCAGCTGGTA CAGAAAGTGC GGAGCAAGAT CGGCTGTGGC    960

ATCCAGCTGA CGCGGGAAGT GGATGGCGTG TGGGTTTACA ACCGCAGCAG TTACCCCATC   1020

TTCATCAAGT CCGCCACACT GGACAACCCG GACTCCAGGA CGCTGTTGGT GCACAAAGTG   1080

TTCCCTGGTT TCTCCATCAA GGCTTTTGAC TATGAGAAAG CCTACAGCCT GCAGCGGCCC   1140

AATGACCACG AGTTCATGCA GCAACCATGG ACGGGTTTCA CCGTGCAGAT CAGCTTTGTG   1200

AAGGGCTGGG GCCAGTGCTA CACCCGCCAG TTCATCAGCA GCTGCCCGTG CTGGCTGGAG   1260

GTCATCTTCA ACAGCCGGTA G                                             1281

(2) INFORMATION FOR SEQ ID NO:8:

(i) SEQUENCE CHARACTERISTICS:
        (A) LENGTH: 1281 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ATGTTCAGGA CCAAACGATC TGCGCTCGTC CGGCGTCTCT GGAGGAGCCG TGCGCCCGGC     60

GGCGAGGACG AGGAGGAGGG CGCAGGGGGA GGTGGAGGAG GAGGCGAGCT GCGGGGAGAA    120

GGGGCGACGG ACAGCCGAGC GCATGGGGCC GGTGGCGGCG GCCCGGGCAG GGCTGGATGC    180

TGCCTGGGCA AGGCGGTGCG AGGTGCCAAA TGTCACCACC ATCCCCACCC GCCAGCCGCG    240

GGCGCCGGCG CGGCCGGGGG CGCCGAGGCG GATCTGAAGG CGCTCACGCA CTCGGTGCTC    300

AAGAAACTGA AGGAGCGGCA GCTGGAGCTG CTGCTCCAGG CCGTGGAGTC CCGCGGCGGG    360

ACGCGCACCG CGTGCCTCCT GCTGCCCGGC CGCCTGGACT GCAGGCTGGG CCCGGGGGCG    420

CCCGCCGGCG CGCAGCCTGC GCAGCCGCCC TCGTCCTACT CGCTCCCCCT CCTGCTGTGC    480

AAAGTGTTCA GGTGGCCGGA TCTCAGGCAT TCCTCGGAAG TCAAGAGGCT GTGTTGCTGT    540

GAATCTTACG GGAAGATCAA CCCCGAGCTG GTGTGCTGCA ACCCCCATCA CCTTAGCCGA    600

CTCTGCGAAC TAGAGTCTCC CCCCCCTCCT TACTCCAGAT ACCCGATGGA TTTTCTCAAA    660

CCAACTGCAG ACTGTCCAGA TGCTGTGCCT TCCTCCGCTG AAACAGGGGG AACGAATTAT    720

CTGGCCCCTG GGGGGCTTTC AGATTCCCAA CTTCTTCTGG AGCCTGGGGA TCGGTCACAC    780
```

-continued

```
TGGTGCGTGG TGGCATACTG GGAGGAGAAG ACGAGAGTGG GGAGGCTCTA CTGTGTCCAG        840

GAGCCCTCTC TGGATATCTT CTATGATCTA CCTCAGGGGA ATGGCTTTTG CCTCGGACAG        900

CTCAATTCGG ACAACAAGAG TCAGCTGGTG CAGAAGGTGC GGAGCAAAAT CGGCTGCGGC        960

ATCCAGCTGA CGCGGGAGGT GGATGGTGTG TGGGTGTACA ACCGCAGCAG TTACCCCATC       1020

TTCATCAAGT CCGCCACACT GGACAACCCG GACTCCAGGA CGCTGTTGGT ACACAAGGTG       1080

TTCCCCGGTT TCTCCATCAA GGCTTTCGAC TACGAGAAGG CGTACAGCCT GCAGCGGCCC       1140

AATGACCACG AGTTTATGCA GCAGCCGTGG ACGGGCTTTA CCGTGCAGAT CAGCTTTGTG       1200

AAGGGCTGGG GCCAGTGCTA CACCCGCCAG TTCATCAGCA GCTGCCCGTG CTGGCTAGAG       1260

GTCATCTTCA ACAGCCGGTA G                                                 1281
```

(2) INFORMATION FOR SEQ ID NO:9:

(i) SEQUENCE CHARACTERISTICS:
    (A) LENGTH: 1491 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:9:

```
ATGTTCAGGT CCAAACGCTC GGGGCTGGTG CGGCGACTTT GGCGAAGTCG TGTGGTCCCC         60

GACCGGGAGG AAGGCGGCAG CGGCGGCGGC GGTGGCGGCG ACGAGGATGG GAGCTTGGGC        120

AGCCGAGCTG AGCCGGCCCC GCGGGCAAGA GAGGGCGGAG GCTGCGGCCG CTCCGAAGTC        180

CGCCCGGTAG CCCCGCGGCG GCCCCGGGAC GCAGTGGGAC AGCGAGGCGC CCAGGGCGCG        240

GGGAGGCGCC GGCGCGCAGG GGGCCCCCCG AGGCCCATGT CGGAGCCAGG GGCCGGCGCT        300

GGGAGCTCCC TGCTGGACGT GGCGGAGCCG GGAGGCCCGG GCTGGCTGCC CGAGAGTGAC        360

TGCGAGACGG TGACCTGCTG TCTCTTTTCG GAGCGGGACG CCGCCGGCGC GCCCCGGGAC        420

GCCAGCGACC CCCTGGCCGG GGCGGCCCTG GAGCCGGCGG GCGGCGGGCG GAGTCGCGAA        480

GCGCGCTCGC GGCTGCTGCT GCTGGAGCAG GAACTCAAAA CCGTCACGTA CTCGCTGCTG        540

AAGCGGCTCA AGGAGCGCTC GCTGGACACG CTGCTGGAGG CGGTGGAGTC CCGCGGCGGC        600

GTGCCGGGCG GCTGCGTGCT GGTGCCGCGC GCCGACCTCC GCCTGGGCGG CCAGCCCGCG        660

CCGCCGCAGC TGCTGCTCGG CCGCCTCTTT CGCTGGCCCG ACCTGCAGCA CGCCGTGGAG        720

CTGAAGCCCC TGTGCGGCTG CCACAGCTTC GCCGCCGCCG CCGACGGCCC TACCGTGTGC        780

TGCAACCCCT ACCACTTCAG CCGGCTCTGC GGGCCCGAAT CTCCGCCACC TCCCTACTCT        840

CGGCTGTCTC CTCGCGACGA GTACAAGCCA CTGGATCTGT CCGATTCCAC ATTGTCTTAC        900

ACTGAAACGA AGGCTACCAA CTCCCTCATC ACTGCTCCGG GTGAATTCTC AGACGCCAGC        960

ATGTCTCCGG ACGCCACCAA GCCGAGCCAC TGGTGCAGCG TGGCGTACTG GGAGCACCGG       1020

ACGCGCGTGG GCCGCCTCTA TGCGGTGTAC GACCAGGCCG TCAGCATCTT CTACGACCTA       1080

CCTCAGGGCA GCGGCTTCTG CCTGGGCCAG CTCAACCTGG AGCAGCGCAG CGAGTCGGTG       1140

CGGCGAACGC GCAGCAAGAT CGGCTTCGGC ATCCTGCTCA GCAAGGAGCC CGACGGCGTG       1200

TGGGCCTACA ACCGCGGCGA GCACCCCATC TTCGTCAACT CCCCGACGCT GGACGCGCCC       1260

GGCGGCCGCG CCCTGGTCGT GCGCAAGGTG CCCCCCGGCT ACTCCATCAA GGTGTTCGAC       1320

TTCGAGCGCT CGGGCCTGCA GCACGCGCCC GAGCCCGACG CCGCCGACGG CCCCTACGAC       1380
```

```
CCCAACAGCG TCCGCATCAG CTTCGCCAAG GGCTGGGGGC CCTGCTACTC CCGGCAGTTC    1440

ATCACCTCCT GCCCCTGCTG GCTGGAGATC CTCCTCAACA ACCCCAGATA G            1491
```

(2) INFORMATION FOR SEQ ID NO:10:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Phe Arg Ser Lys Arg Ser Gly Leu Val Arg Arg Leu Trp Arg Ser
 1               5                  10                  15

Arg Val Val Pro Asp Arg Glu Glu Gly Ser Gly Gly Gly Gly Gly Gly
                20                  25                  30

Gly Asp Glu Asp Gly Ser Leu Gly Ser Arg Ala Glu Pro Ala Pro Arg
            35                  40                  45

Ala Arg Glu Gly Gly Gly Cys Gly Arg Ser Glu Val Arg Pro Val Ala
50                  55                  60

Pro Arg Arg Pro Arg Asp Ala Val Gly Gln Arg Gly Ala Gln Gly Ala
65                  70                  75                  80

Gly Arg Arg Arg Arg Ala Gly Gly Pro Pro Arg Pro Met Ser Glu Pro
                85                  90                  95

Gly Ala Gly Ala Gly Ser Ser Leu Leu Asp Val Ala Glu Pro Gly Gly
            100                 105                 110

Pro Gly Trp Leu Pro Glu Ser Asp Cys Glu Thr Val Thr Cys Cys Leu
        115                 120                 125

Phe Ser Glu Arg Asp Ala Ala Gly Ala Pro Arg Asp Ala Ser Asp Pro
130                 135                 140

Leu Ala Gly Ala Ala Leu Glu Pro Ala Gly Gly Arg Ser Arg Glu
145                 150                 155                 160

Ala Arg Ser Arg Leu Leu Leu Leu Glu Gln Glu Leu Lys Thr Val Thr
                165                 170                 175

Tyr Ser Leu Leu Lys Arg Leu Lys Glu Arg Ser Leu Asp Thr Leu Leu
            180                 185                 190

Glu Ala Val Glu Ser Arg Gly Gly Val Pro Gly Gly Cys Val Leu Val
        195                 200                 205

Pro Arg Ala Asp Leu Arg Leu Gly Gly Gln Pro Ala Pro Pro Gln Leu
210                 215                 220

Leu Leu Gly Arg Leu Phe Arg Trp Pro Asp Leu Gln His Ala Val Glu
225                 230                 235                 240

Leu Lys Pro Leu Cys Gly Cys His Ser Phe Ala Ala Ala Ala Asp Gly
                245                 250                 255

Pro Thr Val Cys Cys Asn Pro Tyr His Phe Ser Arg Leu Cys Gly Pro
            260                 265                 270

Glu Ser Pro Pro Pro Tyr Ser Arg Leu Ser Pro Arg Asp Glu Tyr
        275                 280                 285

Lys Pro Leu Asp Leu Ser Asp Ser Thr Leu Ser Tyr Thr Glu Thr Glu
290                 295                 300

Ala Thr Asn Ser Leu Ile Thr Ala Pro Gly Glu Phe Ser Asp Ala Ser
305                 310                 315                 320

Met Ser Pro Asp Ala Thr Lys Pro Ser His Trp Cys Ser Val Ala Tyr
                325                 330                 335
```

```
Trp Glu His Arg Thr Arg Val Gly Arg Leu Tyr Ala Val Tyr Asp Gln
            340                 345                 350

Ala Val Ser Ile Phe Tyr Asp Leu Pro Gln Gly Ser Gly Phe Cys Leu
            355                 360                 365

Gly Gln Leu Asn Leu Glu Gln Arg Ser Glu Ser Val Arg Arg Thr Arg
            370                 375                 380

Ser Lys Ile Gly Phe Gly Ile Leu Leu Ser Lys Glu Pro Asp Gly Val
385                 390                 395                 400

Trp Ala Tyr Asn Arg Gly Glu His Pro Ile Phe Val Asn Ser Pro Thr
            405                 410                 415

Leu Asp Ala Pro Gly Gly Arg Ala Leu Val Val Arg Lys Val Pro Pro
            420                 425                 430

Gly Tyr Ser Ile Lys Val Phe Asp Phe Glu Arg Ser Gly Leu Gln His
            435                 440                 445

Ala Pro Glu Pro Asp Ala Ala Asp Gly Pro Tyr Asp Pro Asn Ser Val
            450                 455                 460

Arg Ile Ser Phe Ala Lys Gly Trp Gly Pro Cys Tyr Ser Arg Gln Phe
465                 470                 475                 480

Ile Thr Ser Cys Pro Cys Trp Leu Glu Ile Leu Leu Asn Asn Pro Arg
            485                 490                 495
```

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Glu Ser Pro Pro Pro Pro Tyr Ser Arg Leu Ser Pro Arg Asp Glu Tyr
1               5                   10                  15

Lys Pro Leu Asp
            20
```

(2) INFORMATION FOR SEQ ID NO:12:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Ser Arg Gln Phe Ile Thr Ser Cys Pro Cys Trp Leu Glu Ile Leu Asn
1               5                   10                  15

Pro Arg
```

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide -continued (xi) SEQUENCE DESCRIPTION: SEQ ID NO:13:

Lys Glu Arg Gln Leu Glu Leu Leu Leu Gln Ala Val Glu Ser Arg Gly
1               5                   10                  15

Gly Thr Arg Thr Ala
            20

(2) INFORMATION FOR SEQ ID NO:14:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Lys Ala Val Arg Gly Ala Lys Gly His His His Pro His Pro Pro
1               5                   10                  15

(2) INFORMATION FOR SEQ ID NO:15:

(i) SEQUENCE CHARACTERISTICS:
        (A) LENGTH: 733 base pairs
        (B) TYPE: nucleic acid
        (C) STRANDEDNESS: single
        (D) TOPOLOGY: linear (xi) SEQUENCE DESCRIPTION: SEQ ID NO:15:

```
CTCGAGATCC GCCGCCAGGG CCTTAAAACA AAACGAATGA ATGAAGCGCC CGGGCGAGCT      60

CTGCTGGTCT AAATCGGGCC ACTAACCGGC TCATTCCGCT CCAAACTCGC CCGCTCCATG     120

CCCCCAGCTC TTCCGATTTC CCCCTGCTCC CGCTGGGTCT CCGCCAGACC CCCGGGGCCG     180

TCTCGGCCTC CCACCTCCCT CCACCGTGGG TACCCCTCTC TAGACCTGGG AGAGGGTGGC     240

AGTAACTGGG AGGGGGGTTG AAATAGCTTT TAGAAACCCG ATCTGTTGTT TGCGAAACAC     300

AATCGCTTTT TTTTTTTTTA AAGCGACAGG GTGTCTAGAC GGCCACGTGA CGAGGCCGGA     360

GCCGGGCGCG CCACTGCGCA GTGGAACCAG CCGAGCAGAG GGACGGGTGG GGGGGGCGGG     420

AAGGAGGCGG CGGCGGCTGG GGGCGGGGGA GGGAGGGGTA GAGGGGGGAG GGAAGGGGGC     480

GGAGGCGGGA GGCCTTGCGG GAGGCGGCGA GCCCTGGGCA CATTCGCTCG CTGATCGGCG     540

CACAGAGGAT CTTGTCCCCG AGCTGCGCCA GCAGAGCCAG CCGGGCGCCT CGCTCGGTCC     600

GCTCGCCGCG CCGGAGAGAG CTGCCTGAGA CGCAGCCAGC CAGCCAGCCG GCGCCACGCC     660

GCCGAGCGCT CGGCCCCGGA GTCCCTGAGT GCGGCGCGGC GAGCCCCCAG CGGCGGCAGA     720

AGGACTCGAG ATC                                                        733
```